(12) United States Patent
Chen et al.

(10) Patent No.: US 11,759,454 B2
(45) Date of Patent: *Sep. 19, 2023

(54) DIAZOLE LACTAMS

(71) Applicant: CHEMOCENTRYX, INC., Mountain View, CA (US)

(72) Inventors: Xi Chen, East Palo Alto, CA (US); Pingchen Fan, Fremont, CA (US); Yandong Li, San Diego, CA (US); Jay P. Powers, Pacifica, CA (US); Viengkham Malathong, Mountain View, CA (US); Sreenivas Punna, Sunnyvale, CA (US); Hiroko Tanaka, Mountain View, CA (US); Penglie Zhang, Foster City, CA (US); Dean Dragoli, Los Altos, CA (US)

(73) Assignee: CHEMOCENTRYX, INC., Thousand Oaks, CA (US)

( * ) Notice: Subject to any disclaimer, the term of this patent is extended or adjusted under 35 U.S.C. 154(b) by 74 days.

This patent is subject to a terminal disclaimer.

(21) Appl. No.: 16/923,197

(22) Filed: Jul. 8, 2020

(65) Prior Publication Data

US 2021/0093613 A1   Apr. 1, 2021

Related U.S. Application Data

(60) Continuation of application No. 15/074,976, filed on Mar. 18, 2016, now Pat. No. 10,744,118, which is a division of application No. 14/099,541, filed on Dec. 6, 2013, now Pat. No. 9,328,116.

(60) Provisional application No. 61/831,700, filed on Jun. 6, 2013, provisional application No. 61/734,705, filed on Dec. 7, 2012.

(51) Int. Cl.
| | |
|---|---|
| *A61K 31/4178* | (2006.01) |
| *A61K 31/4192* | (2006.01) |
| *A61K 31/4196* | (2006.01) |
| *A61K 45/06* | (2006.01) |
| *C07D 401/14* | (2006.01) |
| *C07D 403/14* | (2006.01) |
| *C07D 405/14* | (2006.01) |
| *C07D 471/04* | (2006.01) |
| *C07D 487/04* | (2006.01) |
| *A61K 31/4155* | (2006.01) |

(52) U.S. Cl.
CPC ...... *A61K 31/4178* (2013.01); *A61K 31/4155* (2013.01); *A61K 31/4192* (2013.01); *A61K 31/4196* (2013.01); *A61K 45/06* (2013.01); *C07D 401/14* (2013.01); *C07D 403/14* (2013.01); *C07D 405/14* (2013.01); *C07D 471/04* (2013.01); *C07D 487/04* (2013.01)

(58) Field of Classification Search
CPC .......... A61P 43/00; A61P 37/08; A61P 37/06; A61P 37/00; A61P 35/00; A61P 29/00; A61P 25/28; A61P 25/16; A61P 25/00; A61P 19/10; A61P 19/02; A61P 17/06; A61P 17/04; A61P 17/02; A61P 11/06; A61P 1/04; C07D 403/14; C07D 405/14; C07D 71/04; C07D 87/04

See application file for complete search history.

(56) References Cited

U.S. PATENT DOCUMENTS

| | | |
|---|---|---|
| 5,817,677 A | 10/1998 | Linz et al. |
| 7,524,845 B2 | 4/2009 | Zhang et al. |
| 7,576,106 B2 | 8/2009 | Zhang et al. |
| 7,629,344 B2 | 12/2009 | Li et al. |
| 7,842,693 B2 | 11/2010 | Pennell et al. |
| 7,888,354 B2 | 2/2011 | Nakamura et al. |
| 8,168,757 B2 | 5/2012 | Finnefrock et al. |
| 8,343,975 B2 | 1/2013 | Zhang et al. |
| 8,354,509 B2 | 1/2013 | Carven et al. |
| 8,552,154 B2 | 10/2013 | Freeman et al. |
| 8,741,295 B2 | 6/2014 | Olive |
| 8,907,053 B2 | 12/2014 | Sasikumar et al. |
| 9,044,442 B2 | 6/2015 | Sasikumar et al. |
| 9,096,642 B2 | 8/2015 | Sasikumar et al. |
| 9,169,248 B2 | 10/2015 | Chen et al. |
| 9,212,224 B2 | 12/2015 | Cogswell et al. |
| 9,233,940 B2 | 1/2016 | Sasikumar et al. |
| 9,328,116 B2 | 5/2016 | Chen et al. |
| 9,750,722 B2 | 9/2017 | Chen et al. |
| 10,568,870 B2 | 2/2020 | Charo et al. |
| 10,744,118 B2 | 8/2020 | Chen et al. |
| 2004/0192750 A1 | 9/2004 | Sanner et al. |

(Continued)

FOREIGN PATENT DOCUMENTS

| | | |
|---|---|---|
| DE | 19539091 A1 | 4/1997 |
| EP | 1 319 657 A1 | 6/2003 |

(Continued)

OTHER PUBLICATIONS

International Search Report and Written Opinion, PCT Application No. PCT/US2013/073692, dated Apr. 8, 2014, 9 pages.
International Search Report and Written Opinion corresponding to PCT/US2013/077257 dated Jun. 25, 2014; 10 pages.
International Search Report dated Aug. 28, 2017 corresponding to PCT/US2017/026290 filed Apr. 6, 2017; 4 pages.
Written Opinion of the ISA dated Aug. 28, 2017 corresponding to PCT/US2017/026290 filed Apr. 6, 2017; 7 pages.

(Continued)

*Primary Examiner* — Savitha M Rao
*Assistant Examiner* — Andrew P Lee
(74) *Attorney, Agent, or Firm* — Mintz Levin Cohn Ferris Glovsky and Popeo PC

(57) ABSTRACT

Compounds are provided that act as potent antagonists of the CCR1 receptor, and have in vivo anti-inflammatory activity. The compounds are diazole lactam derivatives and are useful in pharmaceutical compositions, methods for the treatment of CCR1-mediated disease, and as controls in assays for the identification of competitive CCR1 antagonists.

16 Claims, No Drawings

(56) References Cited

U.S. PATENT DOCUMENTS

| | | |
|---|---|---|
| 2006/0276428 A1 | 12/2006 | Elzein et al. |
| 2007/0088036 A1 | 4/2007 | Zhang et al. |
| 2007/0093467 A1 | 4/2007 | Zhang et al. |
| 2008/0004278 A1 | 1/2008 | Dyckman et al. |
| 2008/0058341 A1 | 3/2008 | Zhang et al. |
| 2008/0269280 A1 | 10/2008 | Zhang et al. |
| 2008/0300257 A1 | 12/2008 | Li et al. |
| 2009/0143377 A1 | 6/2009 | Ng et al. |
| 2009/0252779 A1 | 10/2009 | Zhang et al. |
| 2010/0069396 A1 | 3/2010 | Zhang et al. |
| 2010/0113776 A1 | 5/2010 | Nakamura et al. |
| 2010/0173911 A1 | 7/2010 | Li et al. |
| 2010/0240618 A1 | 9/2010 | Pennell et al. |
| 2011/0098308 A1 | 4/2011 | Zhang et al. |
| 2011/0230521 A1 | 9/2011 | Cook et al. |
| 2012/0010214 A1 | 1/2012 | Li et al. |
| 2012/0108614 A1 | 5/2012 | Chong |
| 2014/0099254 A1 | 4/2014 | Chang |
| 2014/0171420 A1 | 6/2014 | Chen et al. |
| 2014/0179733 A1 | 6/2014 | Chen et al. |
| 2014/0294898 A1 | 10/2014 | Miller et al. |
| 2014/0341917 A1 | 11/2014 | Nastri et al. |
| 2015/0073024 A1 | 3/2015 | Sasikumar et al. |
| 2015/0125463 A1 | 5/2015 | Cogswell et al. |
| 2015/0203580 A1 | 7/2015 | Papadopoulos et al. |
| 2015/0216970 A1 | 8/2015 | Grogan et al. |
| 2015/0291549 A1 | 10/2015 | Chupak et al. |
| 2015/0320859 A1 | 11/2015 | Maecker et al. |
| 2015/0344544 A1 | 12/2015 | Wong et al. |
| 2016/0194295 A1 | 7/2016 | Sasikumar et al. |
| 2016/0194307 A1 | 7/2016 | Chupak et al. |
| 2016/0222060 A1 | 8/2016 | Miller et al. |
| 2018/0071257 A1 | 3/2018 | Chen et al. |
| 2020/0289472 A1 | 9/2020 | Charo et al. |

FOREIGN PATENT DOCUMENTS

| | | | |
|---|---|---|---|
| EP | 2 221 298 A1 | 8/2010 | |
| JP | 2007-513969 A | 5/2007 | |
| JP | 2008-546749 A | 12/2008 | |
| JP | 2010-528038 A | 8/2010 | |
| JP | 2012-502107 A | 1/2012 | |
| WO | 02/10141 A1 | 2/2002 | |
| WO | 2005/056015 A1 | 6/2005 | |
| WO | 2007/002293 A2 | 1/2007 | |
| WO | 2007/026834 A1 | 3/2007 | |
| WO | 2008/045484 A1 | 4/2008 | |
| WO | 2010/030815 A1 | 3/2010 | |
| WO | 2010/053861 A2 | 5/2010 | |
| WO | 2009/063953 A1 | 3/2011 | |
| WO | 2011/029855 A1 | 3/2011 | |
| WO | 2011/161699 A2 | 12/2011 | |
| WO | 2011/161699 A3 | 12/2011 | |
| WO | 2012/168944 A1 | 12/2012 | |
| WO | 2013/132317 A9 | 9/2013 | |
| WO | 2013/144704 A1 | 10/2013 | |
| WO | 2013/0173223 A1 | 11/2013 | |
| WO | 2014/089498 A1 | 6/2014 | |
| WO | 2014/151634 A1 | 9/2014 | |
| WO | 2015/026634 A1 | 2/2015 | |
| WO | 2015/033299 A1 | 3/2015 | |
| WO | 2015/033301 A1 | 3/2015 | |
| WO | 2015/033303 A1 | 3/2015 | |
| WO | 2015/036927 A1 | 3/2015 | |
| WO | 2015/044900 A1 | 4/2015 | |
| WO | 2015/160641 A2 | 10/2015 | |
| WO | 2015/160641 A3 | 10/2015 | |
| WO | 2016/039749 A1 | 3/2016 | |
| WO | 2016/057624 A1 | 4/2016 | |
| WO | 2016/077518 A1 | 5/2016 | |
| WO | 2016/100285 A1 | 6/2016 | |
| WO | 2016/100608 A1 | 6/2016 | |
| WO | 2016/142833 A1 | 9/2016 | |
| WO | 2016/142835 A1 | 9/2016 | |
| WO | 2016/142852 A1 | 9/2016 | |
| WO | 2016/142886 A2 | 9/2016 | |
| WO | 2016/142886 A3 | 9/2016 | |
| WO | 2016/142894 A1 | 9/2016 | |
| WO | 2016/149351 A1 | 9/2016 | |

OTHER PUBLICATIONS

Extended European Search Report corresponding to EP 13866291.1 dated Apr. 18, 2016; 13 pages.

Extended European Search Report corresponding to EP 13859762 dated Sep. 29, 2016, 7 pages.

Extended European Search Report corresponding to EP 17779801.4 dated Nov. 5, 2019; 15 pages.

Ajuebor, Maureen N. et al., "Role of chemokines and chemokine receptors in the gastrointestinal tract," *Immunology*(2002; accepted Jul. 17, 2001); 105:137-143.

Amin, Kawa et al., CC Chemokine Receptors CCR1 and CCR4 are Expressed on Airway Mast Cells in Alelrgic Asthma, *J. Allergy, Clin. Immunol.* (Dec. 2005); 116(6):1383-1385.

Anderson, Matthew W. et al., "C-C Chemokine Receptor 1 Expression in Human Hematolymphoid Nepolasia," *Am. J. Clin. Pathol.* (Mar. 1, 2010); 133(3):473-483.

Borregaard, Jeanett et al., "Evaluation of the effect of the specific CCR1 antagonist CP-481715 on the clinical and cellular responses observed following epicutaneous nickel challenge in human subjects," *Contact Dermatitis*(Feb. 18, 2008); 59:212-219.

Brand, Francois-Xavier et al., Prospect for Anti-HER2 Receptor Therapy in Breast Cancer, *Anticancer Research*(2006; Accepted Sep. 26, 2005) 26:463-470.

Chen, Lieping et al., "Anti-PD-1/PD-L1 therapy of human cancer: past, present, and future," *J Clin Invest.* (Sep. 2015) 125(9):3384-3391.

Chemical Abstracts STN Record for CAS RN 1355557-26-4, entered Feb. 2, 2012.

Chemical Abstracts STN Record for CAS RN 1385289-59-7, entered Aug. 2, 2012.

Chemical Abstracts STN Record for CAS RN 1376355-87-1, entered Jun. 7, 2012.

Dairaghi, Daniel J. et al., "CCR1 blockade reduces tumor burden and osteolysis in vivo in a mouse model of myeloma bone disease," *Blood*(Aug. 16, 2012); 120(7):1449-1457.

Danziger, D. J. et al., "Automated Site-Directed Drug Design: A General Algorithm for Knowledge Acquisition about Hydrogen-Bonding Regions at Protein Surfaces," *Proceedings of the Royal Society of London. Series B, Biological Sciences*(Mar. 22, 1989); 236(1283):101-113.

Dorwald, Florencio Zaragoza "Side Reactions in Organic Synthesis: A Guide to Successful Synthesis Design," 2005 Wiley-VCH Verlag GmbH & Co. KGaA, Wienheim, prface and chapter 1, pp. 1-16.

Gao, Wei et al., "Targeting of the chemokine receptor CCR1 suppresses development of acute and chronic cardiac allograft rejection," *J. Clin. Invest.* (2000; accepted Nov. 23, 1999); 105(1):35-44.

Garcia-Teijido, Paula et al., "Tumor-Infiltrating Lymphocytes in Triple Negative Breast Cancer: The Future of Immune Targeting," *Clinical Medicine Insights: Oncology*(Apr. 5, 2016) 10(supple1):31-39.

Gladue, Ronald P., "Current status of CCR1 antagonists in clinical trials," *Chemokine Biology—Basic Research and Clinical Application*, vol. II(C 2007 Birkhäuser Verlag Basel/Switzerland); pp. 103-113.

Gladue, Ronald P. et al., "CCR1 Antagonists: What Have We Learned From Clinical Trials," *Current Topics in Medicinal Chemistry*(revised Jan. 7, 2010); 10(13):1268-1277.

Hamanishi, Junzo et al., "PD-1/PD-L1 blockade in cancer treatment: perspectives and issues," *Int J Clin Oncol*(published online Feb. 22, 2016) 21:462-473.

Helal, Christopher J. et al., "Potent and cellularly active 4-aminoimidazole inhibitors of cyclin-dependent kinase 5/p25 for the treatment of Alzheimer's disease," *Bioorg. Med. Chem. Lett.* (Aug. 4, 2009); 19:5703-5707.

(56) References Cited

OTHER PUBLICATIONS

Hesselgesser, Joseph et al., "Identification and Characterization of Small Molecule Functional Antagonists of the CCR1 Chemokine Receptor," *J. Biol. Chem.* (Apr. 1, 1998); 273(25):15687-15692.

Joubert, Philippe et al., "Expression and Regulation of CCR1 by Airway Smooth Muscle Cells in Asthma," *J. Immunol.* (Feb. 1, 2008); 180:1268-1275.

Jung, Heiyoun et al., "Combination therapy of chemokine receptor inhibition plus PDL-1 blockade potentiates anti-tumor effects in a murine model of breast cancer," *Journal for Immuno Therapy of Cancer*(Nov. 4, 2015) 3(Suppl2):P227; 1 page.

Jung, Heiyoun et al., "Abstract 564: Combination therapy of chemokine receptor inhibition plus PD-L1 blockade potentiates antitumor effects in a murine model of breast cancer," *Cancer Research*(Jul. 2016); 76(14):564 and 107th Annual Meeting of the American Association for Cancer Research (AACR); New Orleans, LA, USA; Apr. 16-20, 2016; 4 pages.

Klinke, David J., II, "Is immune checkpoint modulation a potential therapeutic option in triple negative breast cancer?" *Breast Cancer Research*(Nov. 7, 2014) 16:457; 2 pages.

Liang, Meina et al., "Species selectivity of a small molecule antagonist for the CCR1 chemokine receptor," *Eur. J. Pharmacol.* (2000; accepted Nov. 30, 1999); 389(1):41-49.

Liang, Meina et al., "Identification and Characterization of a Potent, Selective, and Orally Active Antagonist of the CC Chemokine Receptor-1," *J. Biol. Chem.* (Mar. 29, 2000); 275(25):19000-19008.

Ng, Howard P. et al., "Discovery of Novel Non-Peptide CCR1 Receptor Antagonists," *J. Med. Chem.* (Jun. 21, 1999); 42(22):4680-4694.

Pease, James et al., "Chemokine Receptor Antagonists," *J. Med. Chem.* (Aug. 29, 2012); 55:9363-9392.

Rottman, James B. et al., "Leukocyte recruitment during onsent of experimental allergic encephalomyelitis is CCR1 dependent," *Eur. J. Immunol.* (May 15, 2000); 30:2372-2377.

Strome, Scott E. et al., "A Mechanistic Perspective of Monoclonal Antibodies in Cancer Therapy Beyond Target-Related Effects," *The Oncologist*(accepted for publication Jun. 27, 2007) 12:1084-1095.

Vallet S. et al., "CCR1 as a target for multiple myeloma," (*Abstract, only*) *Expert Opin. Ther. Targets*(Sep. 2011; Epub May 24, 2011); 15(9):1037-47.

Goodman, Alice, "Anti-PD-L1 Agent Shows Activity in Early Study of Triple-Negative Breast Cancer," *The ASCO Post*(Jun. 10, 2015); 4 pages.

Jung, Heiyoun, "Abstract A90: Combination therapy of chemokine receptor inhibition plus PDL-1 blockade potentiates anti-tumor effects in a murine model of breast cancer," *Molecular Cancer Therapeutics*(Dec. 2015) 14(12 Suppl 2);Proceedings of the AACR-NCI-EORTC International Conference: Molecular Targets and Cancer Therapeutics (Nov. 5-9, 2015; Boston, MA; Philadelphia PA): AACR; 3 pages.

Gilchrist, Annette et al., "Targeting Chemokine Receptor CCR1 as a Potential Therapeutic Approach for Multiple Myeloma," *Frontiers in Endocrinology*(Mar. 2, 2022) vol. 13; 16 pages.

DIAZOLE LACTAMS

CROSS-REFERENCES TO RELATED APPLICATIONS

This application is a continuation of U.S. patent application Ser. No. 15/074,976, filed Mar. 18, 2016, which is a divisional of U.S. patent application Ser. No. 14/099,541, filed Dec. 6, 2013 (now U.S. Letters Pat. No. 9,328,116), which claims the benefit of priority to U.S. Provisional Application Ser. No. 61/831,700 filed Jun. 6, 2013 and U.S. Provisional Application Ser. No. 61/734,705 filed Dec. 7, 2012, the disclosures of which are herein incorporated by reference in their entirety.

STATEMENT AS TO RIGHTS TO INVENTIONS MADE UNDER FEDERALLY SPONSORED RESEARCH AND DEVELOPMENT

NOT APPLICABLE

BACKGROUND OF THE INVENTION

The present invention provides compounds, pharmaceutical compositions containing one or more of those compounds or their pharmaceutically acceptable salts, which are effective in inhibiting the binding of various chemokines, such as MIP-1α, leukotactin, MPIF-1 and RANTES, to the CCR1 receptor. As antagonists or modulators for the CCR1 receptor, the compounds and compositions have utility in treating inflammatory and immune disorder conditions and diseases.

Human health depends on the body's ability to detect and destroy foreign pathogens that might otherwise take valuable resources from the individual and/or induce illness. The immune system, which comprises leukocytes (white blood cells (WBCs): T and B lymphocytes, monocytes, macrophages granulocytes, NK cell, mast cells, dendritic cell, and immune derived cells (for example, osteoclasts)), lymphoid tissues and lymphoid vessels, is the body's defense system. To combat infection, white blood cells circulate throughout the body to detect pathogens. Once a pathogen is detected, innate immune cells and cytotoxic T cells in particular are recruited to the infection site to destroy the pathogen. Chemokines act as molecular beacons for the recruitment and activation of immune cells, such as lymphocytes, monocytes and granulocytes, identifying sites where pathogens exist.

Despite the immune system's regulation of pathogens, certain inappropriate chemokine signaling can develop and has been attributed to triggering or sustaining inflammatory disorders, such as rheumatoid arthritis, multiple sclerosis and others. For example, in rheumatoid arthritis, unregulated chemokine accumulation in bone joints attracts and activates infiltrating macrophages and T-cells. The activities of these cells induce synovial cell proliferation that leads, at least in part, to inflammation and eventual bone and cartilage loss (see, DeVries, M. E., et al., *Semin Immunol* 11(2):95-104 (1999)). A hallmark of some demyelinating diseases such as multiple sclerosis is the chemokine-mediated monocyte/macrophage and T cell recruitment to the central nervous system (see, Kennedy, et al., *J Clin. Immunol.* 19(5):273-279 (1999)). Chemokine recruitment of destructive WBCs to transplants has been implicated in their subsequent rejection. See, DeVries, M. E., et al., ibid. Because chemokines play pivotal roles in inflammation and lymphocyte development, the ability to specifically manipulate their activity has enormous impact on ameliorating and halting diseases that currently have no satisfactory treatment. In addition, transplant rejection may be minimized without the generalized and complicating effects of costly immunosuppressive pharmaceuticals.

Chemokines, a group of greater than 40 small peptides (7-10 kD), ligate receptors expressed primarily on WBCs or immune derived cells, and signal through G-protein-coupled signaling cascades to mediate their chemoattractant and chemostimulant functions. Receptors may bind more than one ligand; for example, the receptor CCR1 ligates RANTES (regulated on activation normal T cell expressed), MIP-1α (macrophage inflammatory protein), MPIF-1/CKβ8, and Leukotactin chemokines (among others with lesser affinities). To date, 24 chemokine receptors are known. The sheer number of chemokines, multiple ligand binding receptors, and different receptor profiles on immune cells allow for tightly controlled and specific immune responses. See, Rossi, et al., *Ann. Rev. Immunol.* 18(1):217-242 (2000). Chemokine activity can be controlled through the modulation of their corresponding receptors, treating related inflammatory and immunological diseases and enabling organ and tissue transplants.

The receptor CCR1 and its chemokine ligands, including, for example MIP-1α, MPIF-1/CKβ8, leukotactin and RANTES, represent significant therapeutic targets (see Saeki, et al., *Current Pharmaceutical Design* 9:1201-1208 (2003)) since they have been implicated in rheumatoid arthritis, transplant rejection (see, DeVries, M. E., et al., ibid.), and multiple sclerosis (see, Fischer, et al., *J Neuroimmunol.* 110(1-2):195-208 (2000); Izikson, et al., *J. Exp. Med.* 192(7):1075-1080 (2000); and Rollmnan, et al., *Eur. J. Immunol.* 30(8):2372-2377 (2000). In fact, function-blocking antibodies, modified chemokine receptor ligands and small organic compounds have been discovered, some of which have been successfully demonstrated to prevent or treat some chemokine-mediated diseases (reviewed in Rossi, et al., ibid.). Notably, in an experimental model of rheumatoid arthritis, disease development is diminished when a signaling-blocking, modified-RANTES ligand is administered (see Plater-Zyberk, et al., *Immunol Lett.* 57(1-3):117-120 (1997)). While function-blocking antibody and small peptide therapies are promising, they suffer from the perils of degradation, extremely short half-lives once administered, and prohibitive expense to develop and manufacture, characteristic of most proteins. Small organic compounds are preferable since they often have longer half lives in vivo, require fewer doses to be effective, can often be administered orally, and are consequently less expensive. Some organic antagonists of CCR1 have been previously described (see, Hesselgesser, et al., *J. Biol. Chem.* 273(25): 15687-15692 (1998); Ng, et al., J. Med. Chem. 42(22):4680-4694 (1999); Liang, et al., *J. Biol. Chem.* 275(25):19000-19008 (2000); and Liang, et al., *Eur. J. Pharmacol.* 389(1): 41-49 (2000)). In view of the effectiveness demonstrated for treatment of disease in animal models (see, Liang, et al., *J. Biol. Chem.* 275(25):19000-19008 (2000)), the search has continued to identify additional compounds that can be used in the treatment of diseases mediated by CCR1 signaling.

BRIEF SUMMARY OF THE INVENTION

The present invention relates to compounds having formula I:

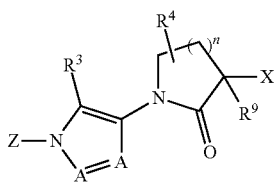

or pharmaceutically acceptable salt, hydrate, solvate, N-oxide or rotamer thereof. In Formula I, the letter n is an integer of from 0 to 3;
each A is independently selected from the group consisting of N and CH;
X and Z are each independently selected from the group consisting
(i) monocyclic or fused-bicyclic aryl and heteroaryl, wherein the heteroaryl group has from 1-4 heteroatoms as ring members selected from N, O and S;
monocyclic four-, five-, six- or seven-membered ring selected from the group consisting of cycloalkane, and heterocycloalkane, wherein the heterocycloalkane rings have from 1-3 heteroatoms as ring members selected from N, O and S;
wherein each of the rings in (i) and (ii) are optionally substituted with from 1 to 5 substituents selected from halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —$OR^a$, —$CO_2R^a$, —$SO_2R^a$, —$NR^aR^b$, —$CONR^aR^b$, aryl, 5- or 6-membered heteroaryl, and 3-, 4-, 5- or 6-membered heterocycloalkane wherein the heteroatoms present as ring vertices of the heteroaryl and heterocycloalkane rings are selected from N, O and S, and wherein the alkyl, cycloalkyl, aryl, heteroaryl and hetereocycloalkane portions of the substituents are optionally further substituted with 1-3 $R^a$; and optionally, two substituents on adjacent ring vertices are connected to form an additional 5- or 6-membered ring which is saturated, unsaturated or aromatic having ring vertices selected from C, O, N and S;
$R^3$ is a member selected from the group consisting of H, halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —$OR^a$, —$CO_2R^a$, —$NR^aR^b$, —$CONR^aR^b$, aryl, 5- or 6-membered heteroaryl, and 3-, 4-, 5- or 6-membered heterocyclic wherein the heteroatoms present as ring vertices of the heteroaryl and heterocyclic rings are selected from N, O and S, and wherein the alkyl, cycloalkyl, aryl, heteroaryl and hetereocyclic portions of $R^3$ are optionally further substituted with 1-3 $R^a$;
$R^4$ is a member selected from the group consisting of H, —$OR^a$ and $C_{1-8}$ alkyl optionally substituted with —$OR^a$;
$R^9$ is a member selected from the group consisting of H and $C_{1-8}$ alkyl optionally substituted with —$OR^a$;
each $R^a$ and $R^b$ is independently selected from the group consisting of hydrogen, hydroxyl, halogen, cyano, $C_{1-8}$ alkyl, $C_{1-8}$ alkoxy, $C_{1-8}$ haloalkyl, $C_{3-6}$ cycloalkyl, $C_{3-6}$ cycloalkylalkyl, amino, $C_{1-8}$ alkylamino, di $C_{1-8}$ alkylamino, carboxamide, carboxy $C_{1-4}$ alkyl ester, carboxylic acid, and —$SO_2$—$C_{1-8}$ alkyl.
In addition to the compounds provided herein, the present invention further provides pharmaceutical compositions containing one or more of these compounds, as well as methods for the use of these compounds primarily to treat diseases associated with CCR1 signalling activity.

BRIEF DESCRIPTION OF THE DRAWINGS

NONE

DETAILED DESCRIPTION OF THE INVENTION

I. Abbreviation and Definitions

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkane" or "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkane may be a monocyclic, a bicyclic or a polycyclic ring system. Non limiting examples of heterocycloalkane groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkane group can be attached to the remainder of the molecule through a ring carbon or a heteroatom.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

As used herein, a wavy line, "⌇", that intersects a single, double or triple bond in any chemical structure depicted herein, represent the point attachment of the single, double, or triple bond to the remainder of the molecule.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as dialkylamino or —NR$^a$R$^b$ is meant to include piperidinyl, pyrrolidinyl, morpholinyl, azetidinyl and the like.

The term "di-(C$_{1-4}$ alkyl)amino-C$_{1-4}$ alkyl" refers to an amino group bearing two C$_{1-4}$ alkyl groups that can be the same or different (e.g., methyl, ethyl, propyl, isopropyl, n-butyl, sec-butyl, isobutyl and tert-butyl) and which is attached to the remainder of the molecule through a C$_{1-4}$ alkyl group (a one to four carbon alkylene linking group). Examples of di-(C$_{1-4}$alkyl)amino-C$_{1-4}$ alkyl groups include dimethylaminomethyl, 2-(ethyl(methyl)amino)ethyl, 3-(dimethylamino)butyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "C$_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, is oindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

The term "arylalkyl" is meant to include those radicals in which an aryl group is attached to an alkyl group (e.g., benzyl, phenethyl, and the like). Similarly, the term "heteroaryl-alkyl" is meant to include those radicals in which a heteroaryl group is attached to an alkyl group (e.g., pyridylmethyl, thiazolylethyl, and the like).

The above terms (e.g., "alkyl," "aryl" and "heteroaryl"), in some embodiments, will include both substituted and unsubstituted forms of the indicated radical. Preferred substituents for each type of radical are provided below.

Substituents for the alkyl radicals (including those groups often referred to as alkylene, alkenyl, alkynyl and cycloalkyl) can be a variety of groups selected from: -halogen, —OR', —NR'R", —SR', —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R''' each independently refer to hydrogen, unsubstituted C$_{1-8}$ alkyl, unsubstituted aryl, aryl substituted with 1-3 halogens, unsubstituted C$_{1-8}$ alkyl, C$_{1-8}$ alkoxy or C$_{1-8}$ thioalkoxy groups, or unsubstituted aryl-C$_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro(C$_1$-C$_4$)alkoxy, and perfluoro(C$_1$-C$_4$)alkyl, in a number ranging from zero to the total number of open valences on the aromatic ring system; and where R', R" and R''' are independently selected from hydrogen, C$_{1-8}$ alkyl, C$_{1-8}$ haloalkyl, C$_{3-6}$ cycloalkyl, C$_{2-8}$ alkenyl, C$_{2-8}$ alkynyl, unsubstituted aryl and heteroaryl, (unsubstituted aryl)-C$_{1-4}$ alkyl, and unsubstituted aryloxy-C$_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula-A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Saks", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3H$), iodine-125 ($^{125}I$) or carbon-14 ($^{14}C$), or non-radioactive isotopes, such as deuterium ($^2H$) or carbon-13 ($^{13}C$). Such isotopic variations can provide additional utilities to those described elsewhere with this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The term "and acid isosteres" means, unless otherwise stated, a group which can replace a carboxylic acid, having an acidic functionality and steric and electronic characteristics that provide a level of activity (or other compound characteristic such as solubility) similar to a carboxylic acid. Representative acid isosteres include, hydroxamic acids, sulfonic acids, sulfonic acids, sulfonamides, acyl-sulfonamides, phosphonic acids, phosphinic acids, phosphoric acids, tetrazole, and oxo-oxadiazoles.

Compounds of the invention having formula I can exist in different isomeric forms. As used herein, the terms cis or trans are used in their conventional sense in the chemical arts, i.e., referring to the position of the substituents to one another relative to a reference plane, e.g., a double bond, or a ring system, such as a decalin-type ring system or a hydroquinolone ring system: in the cis isomer, the substituents are on the same side of the reference plane, in the trans isomer the substituents are on opposite sides. Additionally, different conformers are contemplated by the present invention, as well as distinct rotamers. Conformers are conformational isomers that can differ by rotations about one or more a bonds. Rotamers are conformers that differ by rotation about only a single a bond.

II. General

The present invention derives from the discovery that compounds of formula I act as potent antagonists of the CCR1 receptor. The compounds have in vivo anti-inflammatory activity and have superior pharmacokinetic properties. Accordingly, the compounds provided herein are useful in pharmaceutical compositions, methods for the treatment of CCR1-mediated diseases, and as controls in assays for the identification of competitive CCR1 antagonists.

III. Compounds

In one aspect, the present invention provides for a compound of Formula I:

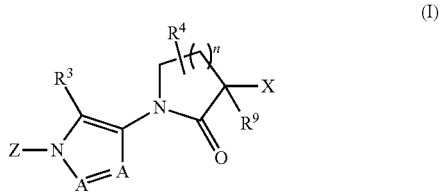

(I)

or pharmaceutically acceptable salt, hydrate, solvate, N-oxide or rotamer thereof. In Formula I, the letter n is an integer of from 0 to 3;

each A is independently selected from the group consisting of N and CH;

X and Z are each independently selected from the group consisting
  (i) monocyclic or fused-bicyclic aryl and heteroaryl, wherein the heteroaryl group has from 1-4 heteroatoms as ring members selected from N, O and S;
  (ii) monocyclic four-, five-, six- or seven-membered ring selected from the group consisting of cycloalkane, and heterocycloalkane, wherein the heterocycloalkane rings have from 1-3 heteroatoms as ring members selected from N, O and S;
  wherein each of the rings in (i) and (ii) are optionally substituted with from 1 to 5 substituents selected from halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —$OR^a$, —$CO_2R^a$, —$SO_2R^a$, —$NR^aR^b$, —$CONR^aR^b$, aryl, 5- or 6-membered heteroaryl, and 3-, 4-, 5- or 6-membered heterocycloalkane wherein the heteroatoms present as ring vertices of the heteroaryl and heterocycloalkane rings are selected from N, O and S, and wherein the alkyl, cycloalkyl, aryl, heteroaryl and hetereocycloalkane portions of the substituents are optionally further substituted with 1-3 $R^a$; and optionally, two substituents on adjacent ring vertices are connected to form an additional 5- or 6-membered ring which is saturated, unsaturated or aromatic having ring vertices selected from C, O, N and S;

$R^3$ is a member selected from the group consisting of H, halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —$OR^a$, —$CO_2R^a$, —$NR^aR^b$, —$CONR^aR^b$, aryl, 5- or 6-membered heteroaryl, and 3-, 4-, 5- or 6-membered heterocyclic wherein the heteroatoms present as ring vertices of the heteroaryl and heterocyclic rings are selected from N, O and S, and wherein the alkyl, cycloalkyl, aryl, heteroaryl and hetereocyclic portions of $R^3$ are optionally further substituted with 1-3 $R^a$;

$R^4$ is a member selected from the group consisting of H, —$OR^a$ and $C_{1-8}$ alkyl optionally substituted with —$OR^a$;

$R^9$ is a member selected from the group consisting of H and $C_{1-8}$ alkyl optionally substituted with —$OR^a$;

each $R^a$ and $R^b$ is independently selected from the group consisting of hydrogen, hydroxyl, halogen, cyano, $C_{1-8}$ alkyl, $C_{1-8}$ alkoxy, $C_{1-8}$ haloalkyl, $C_{3-6}$ cycloalkyl, $C_{3-6}$ cycloalkylalkyl, amino, $C_{1-8}$ alkylamino, di $C_{1-8}$ alkylamino, carboxamide, carboxy $C_{1-4}$ alkyl ester, carboxylic acid, and —$SO_2$—$C_{1-8}$ alkyl.

In some selected embodiments, the compounds of Formula I are represented by Formula Ia:

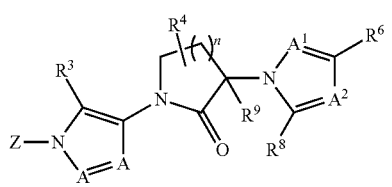

(Ia)

wherein $A^1$ is N or $C(R^5)$; $A^2$ is N or $C(R^7)$; and $R^5$, $R^6$, $R^7$ and $R^8$ are each independently selected from H, halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —$OR^a$, —$CO_2R^a$, —$NR^aR^b$, —$CONR^aR^b$, aryl, 5- or 6-membered heteroaryl, and 3-, 4-, 5- or 6-membered heterocycloalkane wherein the heteroatoms present as ring vertices of the heteroaryl and heterocycloalkane rings are selected from N, O and S, and wherein the alkyl, cycloalkyl, aryl, heteroaryl and hetereocycloalkane portions of $R^5$, $R^6$, $R^7$ and $R^8$ are optionally further substituted with 1-3 $R^a$; and optionally, adjacent members of $R^5$, $R^6$, $R^7$ and $R^8$ are connected to form an additional 5- or 6-membered ring which is saturated, unsaturated or aromatic having ring vertices selected from C, O, N and S; or a pharmaceutically acceptable salt, hydrate, solvate, rotamer or N-oxide thereof.

In other selected embodiments, the compounds of Formula Ia are those wherein $R^8$ is other than H.

In other selected embodiments, the compounds of Formula Ia are represented by Formula Ib:

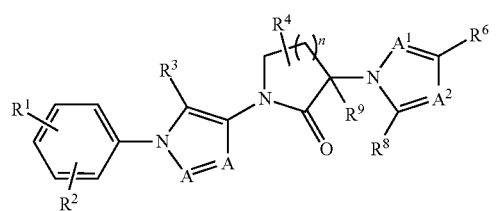

(Ib)

wherein $R^1$ and $R^2$ are each independently selected from H, halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —$OR^a$, —$CO_2R^a$, —$SO_2R^a$, —$NR^aR^b$, —$CONR^aR^b$, and 3-, 4-, 5- or 6-membered heterocycloalkane wherein the heteroatoms present as ring vertices of the heterocycloalkane ring are selected from N, O and S, and wherein the alkyl, cycloalkyl and hetereocycloalkane portions of $R^1$ and $R^2$ are optionally further substituted with 1-3 $R^a$.

In selected embodiments of Formula Ib, each $R^1$ and $R^2$ is independently selected from H, halogen, CN, $C_{1-8}$ alkyl, $C_{1-8}$ haloalkyl, —$CO_2R^a$ and —$SO_2R^a$.

In other selected embodiments for the compounds of Formula Ib, the ring portion having N, $A^1$ and $A^2$ as ring vertices is selected from:

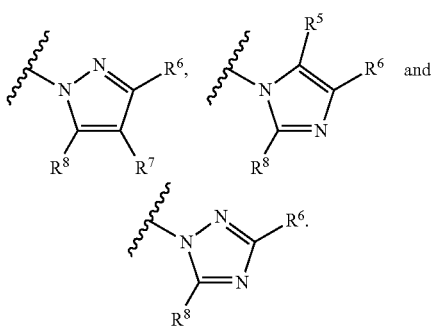

In still other selected embodiments for the compounds of Formula Ib, the ring portion having N, $A^1$ and $A^2$ as ring vertices is selected from:

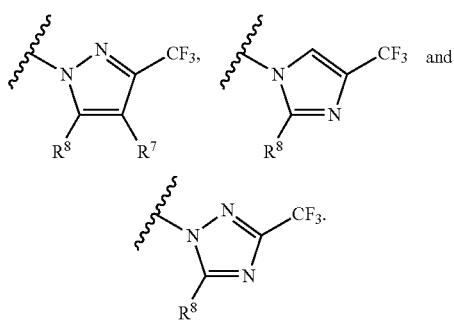

wherein $R^7$ is H or Cl, and $R^8$ is $C_{1-8}$ alkyl optionally substituted with 1 or 2 $R^a$.

In still other selected embodiments of Formula Ib, $R^9$ is H or $CH_3$.

Returning to Formula I, some selected embodiments are those compounds represented by Formula Ic:

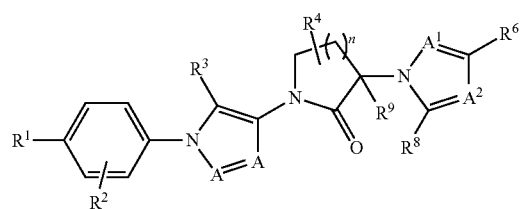
(Ic)

wherein the letter n is 1, 2 or 3. Other selected embodiments are those wherein n is 1.

In still other selected embodiments, the compounds of Formula Ib are those represented by Formula Ib1:

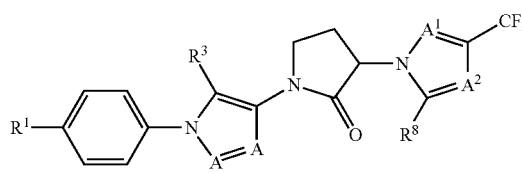
(Ib1)

wherein $R^1$ is Cl or F.

In still other selected embodiments, the compounds of Formula Ib1 are represented by Formulae Ib1a, Ib1b and Ib1c.

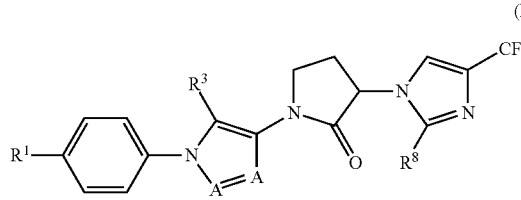
(Ib1a)

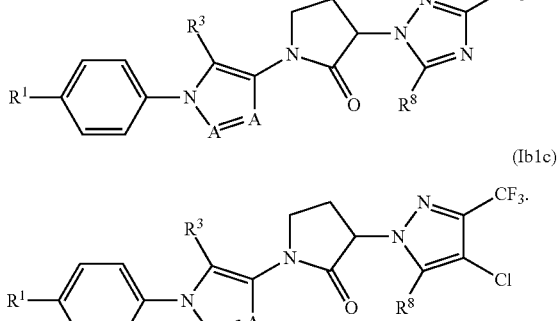
(Ib1b)
(Ib1c)

In some selected embodiments of Formula Ib, the compounds are represented by Formula Ib2:

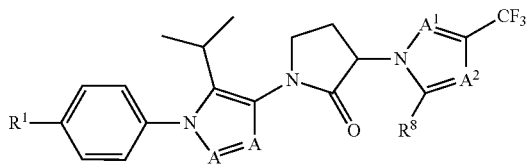
(Ib2)

wherein $R^1$ is Cl or F.

In some selected embodiments of Formula Ib, the compounds are represented by Formulae Ib3a, Ib3b and Ib3c.

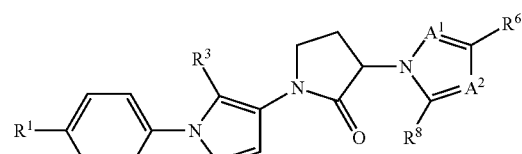
(Ib3a)

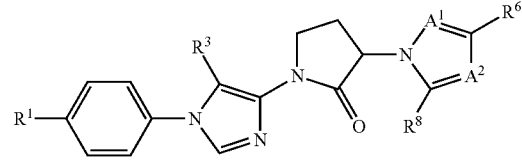
(Ib3c)

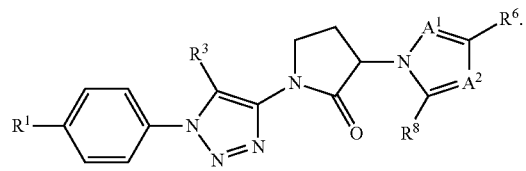
(Ib3c)

In selected embodiments of any of Formulae I, Ia, Ib, Ic, Ib1, Ib1a, Ib1b, Ib1c, Ib2, Ib3a, Ib3b and Ib3c, $R^3$ is selected from H, $C_{1-8}$ alkyl, $C_{3-8}$ cycloalkyl and $C_{2-8}$ alkenyl.

Preparation of Compounds

The schemes in the Examples below provide certain synthetic routes that can be followed to access certain compounds of the present invention. Other routes or modification of the routes presented below would be readily apparent to a skilled artisan and are within the scope of the present invention.

IV. Pharmaceutical Compositions

In addition the compounds provided above, the compositions for modulating CCR1, CCR2 and CCR3 activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsification as described in U.S. Pat. No. 6,451,339, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of the invention may be formulated for depositing into a medical device, which may include any of variety of conventional grafts, stents, including stent grafts, catheters, balloons, baskets or other device that can be deployed or permanently implanted within a body lumen. As a particular example, it would be desirable to have devices and methods which can deliver compounds of the invention to the region of a body which has been treated by interventional technique.

In exemplary embodiment, the inhibitory agent of this invention may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No. 4,886,062 (Wiktor). Such designs include both metal and polymeric stents, as well as self-expanding and balloon-expandable stents. Stents may also used to deliver a drug at the site of contact with the vasculature, as disclosed in U.S. Pat. No. 5,102,417 (Palmaz) and in International Patent Application Nos. WO 91/12779 (Medtronic, Inc.) and WO 90/13332 (Cedars-Sanai Medical Center), U.S. Pat. No. 5,419,760 (Narciso, Jr.) and U.S. Pat. No. 5,429,634 (Narciso, Jr.), for example. Stents have also been used to deliver viruses to the wall of a lumen for gene delivery, as disclosed in U.S. Pat. No. 5,833,651 (Donovan et al).

The term "deposited" means that the inhibitory agent is coated, adsorbed, placed, or otherwise incorporated into the device by methods known in the art. For example, the inhibitory agent may be embedded and released from within ("matrix type") or surrounded by and released through ("reservoir type") polymer materials that coat or span the medical device. In the later example, the inhibitory agent may be entrapped within the polymer materials or coupled to the polymer materials using one or more the techniques for generating such materials known in the art. In other formulations, the inhibitory agent may be linked to the surface of the medical device without the need for a coating by means of detachable bonds and release with time, can be removed by active mechanical or chemical processes, or are in a permanently immobilized form that presents the inhibitory agent at the implantation site.

In one embodiment, the inhibitory agent may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D, L-lactic acid), poly(D,L-lactide) (PLA), poly (L-lactide) (PLLA), poly(glycolic acid-co-trimethylene carbonate) (PGA/PTMC), polyethylene oxide (PEO), polydioxanone (PDS), polyphosphoester, polyphosphoester urethane, poly (amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable poplymers known in the art. Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In one embodiment of the invention, the inhibitory agent of the invention is coupled to a polymer or semipermeable polymer matrix that is formed as a stent or stent-graft device.

Typically, polymers are applied to the surface of an implantable device by spin coating, dipping or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In preferred embodiments of the invention, the inhibitory agent is formulated for release from the polymer coating into the environment in which the medical device is placed.

Preferably, the inhibitory agent is released in a controlled manner over an extended time frame (e.g., months) using at least one of several well-known techniques involving polymer carriers or layers to control elution. Some of these techniques were previously described in U.S. Patent Application 20040243225A1.

Moreover, as described for example in U.S. Pat. No. 6,770,729, the reagents and reaction conditions of the polymer compositions can be manipulated so that the release of the inhibitory agent from the polymer coating can be controlled. For example, the diffusion coefficient of the one or more polymer coatings can be modulated to control the release of the inhibitory agent from the polymer coating. In a variation on this theme, the diffusion coefficient of the one or more polymer coatings can be controlled to modulate the ability of an analyte that is present in the environment in which the medical device is placed (e.g. an analyte that facilitates the breakdown or hydrolysis of some portion of the polymer) to access one or more components within the polymer composition (and for example, thereby modulate the release of the inhibitory agent from the polymer coating). Yet another embodiment of the invention includes a device having a plurality of polymer coatings, each having a plurality of diffusion coefficients. In such embodiments of the invention, the release of the inhibitory agent from the polymer coating can be modulated by the plurality of polymer coatings.

In yet another embodiment of the invention, the release of the inhibitory agent from the polymer coating is controlled by modulating one or more of the properties of the polymer composition, such as the presence of one or more endogenous or exogenous compounds, or alternatively, the pH of the polymer composition. For example, certain polymer compositions can be designed to release a inhibitory agent in response to a decrease in the pH of the polymer composition. Alternatively, certain polymer compositions can be designed to release the inhibitory agent in response to the presence of hydrogen peroxide.

III. Methods of Treating Diseases Modulated by CCR1

In yet another aspect, the present invention provides methods of treating CCR1-mediated conditions or diseases by administering to a subject having such a disease or condition, a therapeutically effective amount of a compound of formula I above. The "subject" is defined herein to include animals such as mammals, including, but not limited to, primates (e.g., humans), cows, sheep, goats, horses, dogs, cats, rabbits, rats, mice and the like.

CCR1 provides a target for interfering with or promoting specific aspects of immune cell functions, or more generally, with functions associated with CCR1 expression on a wide range of cell types in a mammal, such as a human. Compounds that inhibit CCR1, are particularly useful for modulating monocyte, macrophage, lymphocyte, granulocyte, NK cell, mast cells, dendritic cell, and certain immune derived cell (for example, osteoclasts) function for therapeutic purposes. Accordingly, the present invention is directed to compounds which are useful in the prevention and/or treatment of a wide variety of inflammatory and immunoregulatory disorders and diseases (see Saeki, et al., *Current Pharmaceutical Design* 9:1201-1208 (2003)).

For example, an instant compound that inhibits one or more functions of CCR1 may be administered to inhibit (i.e., reduce or prevent) inflammation or cellular infiltration associated with an immune disorder. As a result, one or more inflammatory processes, such as leukocyte emigration or infiltration, chemotaxis, exocytosis (e.g., of enzymes, histamine) or inflammatory mediator release, can be inhibited. For example, monocyte infiltration to an inflammatory site (e.g., an affected joint in arthritis, or into the CNS in MS) can be inhibited according to the present method.

Similarly, an instant compound that promotes one or more functions of CCR1 is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, monocytes can be recruited to combat bacterial infections.

Diseases and conditions associated with inflammation, immune disorders and infection can be treated using the method of the present invention. In a preferred embodiment, the disease or condition is one in which the actions of immune cells such monocyte, macrophage, lymphocyte, granulocyte, NK cell, mast cell, dendritic cell, or certain immune derived cell (for example, osteoclasts) are to be inhibited or promoted, in order to modulate the inflammatory or autoimmune response.

In one group of embodiments, diseases or conditions, including chronic diseases, of humans or other species can treated with modulators of CCR1 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as asthma, allergic asthma, allergic rhinitis, hypersensitivity lung diseases and the like, (9) autoimmune diseases, such as fibromyalagia, scleroderma, ankylosing spondylitis, juvenile RA, Still's disease, polyarticular juvenile RA, pauciarticular juvenile RA, polymyalgia rheumatica, Takuyasu arthritis, rheumatoid arthritis, psoriatic arthritis, osteoarthritis, polyarticular arthritis, multiple sclerosis, systemic lupus erythematosus, type I diabetes, type II diabetes, type I diabetes (recent onset), optic neuritis, glomerulonephritis, and the like, (10) graft rejection including allograft rejection and acute and chronic graft-vs-host disease, (11) fibrosis (e.g. pulmonary fibrosis (i.e. idiopathic pulmonary fibrosis, interstitial pulmonary fibrosis), fibrosis associated with end-stage renal disease, fibrosis caused by radiation, tubulointerstitial fibrosis, subepithelieal fibrosis, scleroderma (progressive systemic sclerosis), hepatic fibrosis (including that caused by alcoholic or viral hepatitis), primary and secondary cirrhosis), (12) acute and chronic lung inflammation (chronic obstructive pulmonary disease, chronic bronchitis, adult respiratory distress syndrome, respiratory distress syndrome of infancy, immune complex alveolitis) and (13) other diseases in which undesired inflammatory responses or immune disorders are to be inhibited, such as cardiovascular disease including atherosclerosis, vascular inflammation resulting from tissue transplant or during restenosis (including, but not limited to restenosis following angioplasty and/or stent insertion), other acute and chronic inflammatory conditions such as myositis, neurodegenerative diseases (e.g., Alzheimer's disease), encephalitis, meningitis, hepatitis, nephritis, sepsis, sarcoidosis, allergic conjunctivitis, otitis, sinusitis, synovial inflammation caused by arthroscopy, hyperuremia, trauma, ischaemia reperfusion injury, nasal polyosis, preeclampsia, oral lichen planus, Guillina-Barre syndrome, granulomatous diseases, conditions associated with leptin production, Behcet's syndrome and gout and in wound healing applications (14) immune mediated food allergies such as Celiac disease (15) diseases of osteoclast dysregulation including osteoporosis and osteolytic bone diseases associated with cancers such as multiple myeloma.

In another group of embodiments, diseases or conditions can be treated with modulators of CCR1 function. Examples of diseases to be treated with modulators of CCR1 function include cancers (both primary and metastatic) (e.g., multiple myeloma; Hata, H., Leukemia & Lymphoma, 2005, 46(7); 967-972), cardiovascular diseases, diseases in which angiogenesis or neovascularization play a role (neoplastic diseases, retinopathy and macular degeneration), infectious diseases (viral infections, e.g., HIV infection, and bacterial infections) and immunosuppressive diseases such as organ transplant conditions and skin transplant conditions. The term "organ transplant conditions" is meant to include bone marrow transplant conditions and solid organ (e.g., kidney, liver, lung, heart, pancreas or combination thereof) transplant conditions.

Pharmaceutical compositions of this invention can also inhibit the production of metalloproteinases and cytokines at inflammatory sites, either directly or indirectly (as a consequence of decreasing cell infiltration) thus providing benefit for diseases or conditions linked to these cytokines.

The compounds of the present invention are accordingly useful in the prevention and treatment of a wide variety of inflammatory and immunoregulatory disorders and diseases.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

Those of skill in the art will understand that agents that modulate CCR1 activity can be combined in treatment regimens with other therapeutic agents and/or with chemotherapeutic agents or radiation. In some cases, the amount of chemotherapeutic agent or radiation is an amount which would be sub-therapeutic if provided without combination with a composition of the invention. Those of skill in the art will appreciate that "combinations" can involve combinations in treatments (i.e., two or more drugs can be administered as a mixture, or at least concurrently or at least introduced into a subject at different times but such that both are in the bloodstream of a subject at the same time). Additionally, compositions of the current invention may be administered prior to or subsequent to a second therapeutic regimen, for instance prior to or subsequent to a dose of chemotherapy or irradiation.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

Diseases and conditions associated with inflammation, immune disorder, infection and cancer can be treated or prevented with the present compounds, compositions, and methods.

The compounds and compositions of the present invention can be combined with other compounds and compositions having related utilities to prevent and treat the condition or disease of interest, such as inflammatory or autoimmune disorders, conditions and diseases, including inflammatory bowel disease, rheumatoid arthritis, osteoarthritis, psoriatic arthritis, polyarticular arthritis, multiple sclerosis, allergic diseases, psoriasis, atopic dermatitis and asthma, and those pathologies noted above.

For example, in the treatment or prevention of inflammation or autimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non sedating antihistamine.

Likewise, compounds and compositions of the present invention may be used in combination with other drugs that are used in the treatment, prevention, suppression or amelioration of the diseases or conditions for which compounds and compositions of the present invention are useful. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolimus (FK-506, Prograf®), rapamycin (sirolimus, Rapamune®), Tofacitinib (Xeljanz®) and other FK-506 type immunosuppressants, and mycophenolate, e.g., mycophenolate mofetil (CellCept®); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophyline, cromolyn sodium, atropine, ipratropium bromide, leukotriene antagonists (e.g., zafmlukast, montelukast, pranlukast, iralukast, pobilukast and SKB-106, 203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, niroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbrel®), (k) antibody therapies such as orthoclone (OKT3), daclizumab (Zenapax®), basiliximab (Simulect®) and infliximab (Remicade®), adalimumab (Humira®), golimumab (Simponi®), rituximab (Rituxan®), tocilizumab (Actemra®), (l) other antagonists of the chemokine receptors, especially CCR5, CXCR2, CXCR3, CCR2, CCR3, CCR4, CCR7, $CX_3CR1$ and CXCR6; (m) lubricants or emollients such as petrolatum and lanolin, (n) keratolytic agents (e.g., tazarotene), (o) vitamin $D_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon (β-1α (Avonex®), azathioprine (Imurek®, Imuran®), glatiramer acetate (Capoxone®), a glucocorticoid (e.g., prednisolone) and cyclophosphamide (t) DMARDS such as methotrexate and leflunomide (u) other compounds such as 5-aminosalicylic acid and prodrugs thereof; hydroxychloroquine; D-penicillamine; antimetabolites such as azathioprine, 6-mercaptopurine and methotrexate; DNA synthesis inhibitors such as hydroxyurea and microtubule disrupters such as colchicine and proteasome inhibitors such as bortezomib (Velcade®). The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

IV. Examples

The following examples are offered to illustrate, but not to limit the claimed invention.

Reagents and solvents used below can be obtained from commercial sources such as Aldrich Chemical Co. (Milwaukee, Wis., USA). $^1$H-NMR were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parentheses). In tables, a single m/e value is reported for the M+H (or, as noted, M–H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC equipped with an Agilent Zorbax SB-C18, 2.1×50 mm, 5μ column for sample delivery. Normally the analyte was dissolved in methanol at 0.1 mg/mL and 1 microlitre was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM NH$_4$OAc in acetonitrile/water as delivery system.

The following abbreviations are used in the Examples and throughout the description of the invention:

HPLC, High Pressure Liquid Chromatography; DMF, Dimethyl formamide; TFA, Trifluoroacetic Acid; THF, Tetrahydrofuran; EtOAc, Ethyl acetate; BOC$_2$O, di-tertbutyl dicarbonate or BOC anhydride; HPLC, High Pressure Liquid Chromatography; DIPEA, Diisopropyl ethylamine; HBTU, O-(benzotriazol-1-yl)-N,N,N',N'-tetramethyluronium hexafluorophosphate; dppf, 1,1'-Bis(diphenylphosphino)ferrocene; Pd$_2$(dba)$_3$, Tris(dibenzylideneacetone)dipalladium(O); DIPEA, diisopropylethylamine; DMP, dimethylphthalate; Me, methyl; Et, ethyl; DCM, dichloromethane.

Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1

Synthesis of 1-[1-(4-fluorophenyl)-5-methylpyrazol-4-yl]-3-[5-methyl-3-(trifluoromethyl)-1,2,4-triazol-1-yl]pyrrolidin-2-one

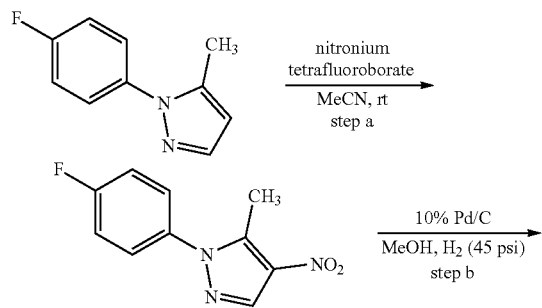

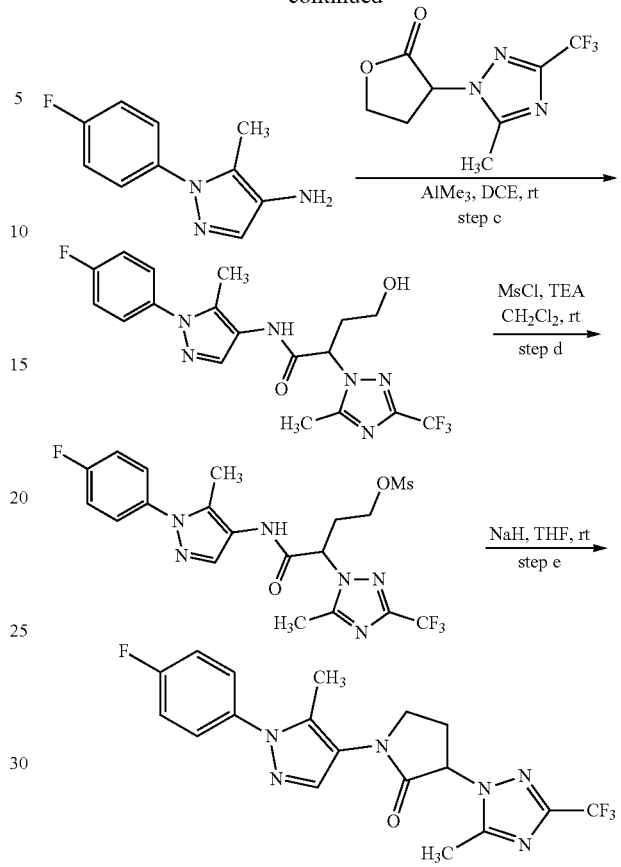

a) Nitronium tetrafluoroborate (110 mg, 0.84 mmol) was added to a solution of 1-(4-fluorophenyl)-5-methyl-1H-pyrazole (120 mg, 0.70 mmol) in anhydrous acetonitrile (5.0 mL) under nitrogen at room temperature. After stirring for 12 h, the mixture was concentrated in vacuo and purified by flash chromatography (SiO$_2$, 20% EtOAc/hexanes) to give the product (53 mg, 0.24 mmol, 34%) as a colorless oil.

b) A heavy-walled glass flask containing 1-(4-fluorophenyl)-5-methyl-4-nitro-pyrazole (50 mg, 0.23 mmol) from step a and 10% Pd/C (10 mg, 20 wt %) in MeOH (5 mL) was fitted onto a Parr apparatus and agitated under H$_2$ at 45 psi. After 1 h, the reaction mixture was filtered through a pad of Celite and the filtrate was concentrated in vacuo to afford the product (240 mg, 1.2 mmol, 99%) as an orange oil. The crude material was carried to the next step without further purification.

c) Trimethylaluminum (0.25 mL, 2 M in toluene, 0.50 mmol) was slowly added to a solution of 1-(4-fluorophenyl)-5-methylpyrazol-4-amine (47 mg, 0.25 mmol) from step b and 3-[5-methyl-3-(trifluoromethyl)-1,2,4-triazol-1-yl]tetrahydrofuran-2-one (58 mg, 0.25 mmol) in 1,2-dichloroethane (5 mL) under nitrogen. The mixture was allowed to stir at room temperature for 20 min before the reaction was carefully quenched by adding 1-2 drops of 1 N HCl. After bubbling subsided, the thick mixture was diluted with additional 1 N HCl and extracted with CH$_2$Cl$_2$ (3×20 mL). The combined organic extracts were dried over MgSO$_4$, filtered, and concentrated in vacuo. The crude material was carried to the next step without further purification.

d) To a solution of the crude alcohol intermediate (assumed 0.25 mmol) from step c and triethylamine (0.14 mL, 1.0 mmol) in CH$_2$Cl$_2$ (3 mL) was slowly added methanesulfonyl chloride (0.040 mL, 0.50 mmol). The reaction mixture was allowed to stir at room temperature for 15 min before it was diluted with $CH_2Cl_2$ and washed with water. The organic layer was separated, dried over $MgSO_4$, filtered, and concentrated in vacuo. The crude yellow oil was carried to the next step without further purification.

e) To the crude mesylate intermediate (assumed 0.25 mmol) from step d in tetrahydrofuran (2 mL) was added sodium hydride (40 mg, 60% in mineral oil, 1.0 mmol) in one portion at room temperature. After stirring for 30 min, the reaction was quenched by the addition of saturated aqueous $NH_4Cl$ and extracted with $CH_2Cl_2$ (2×20 mL). The organic layers were combined, dried over $MgSO_4$, filtered and concentrated in vacuo. The crude residue was purified by reverse phase HPLC (C18 column, acetonitrile $H_2O$ with 0.1% TFA as eluent) to afford the titled compound (35 mg, 0.086 mmol, 34% over three steps) as a white solid. $^1H$ NMR (400 MHz, $CDCl_3$) δ 7.65 (s, 1H), 7.42 (dd, J=9.0, 5.1 Hz, 2H), 7.18 (dd, J=8.8, 8.0 Hz, 2H), 5.11 (dd, J=8.6, 6.4 Hz, 1H), 4.07 (ddd, J=9.8, 8.6, 5.8 Hz, 1H), 3.92 (ddd, J=9.8, 7.8, 5.8 Hz, 1H), 2.80-2.88 (m, 2H), 2.66 (s, 3H), 2.22 (s, 3H); MS: (ES) m/z calculated for $C_{18}H_{16}F_4N_6O$ $[M+H]^+$ 409.1, found 409.1.

Example 2

Synthesis of 3-[4-chloro-5-methyl-3-(trifluoromethyl)pyrazol-1-yl]-1-[1-(4-fluorophenyl)-5-methylpyrazol-4-yl]pyrrolidin-2-one

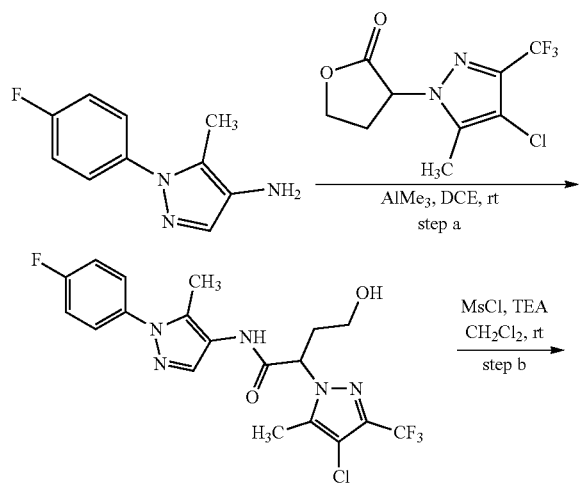

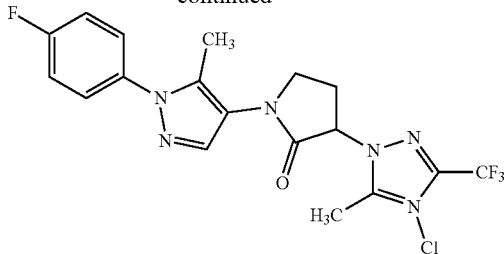

a) Trimethylaluminum (0.16 mL, 2 M in toluene, 0.32 mmol) was slowly added under nitrogen to a solution of the 1-(4-fluorophenyl)-5-methylpyrazol-4-amine (40 mg, 0.21 mmol) and 3-[5-methyl-3-(trifluoromethyl)-1,2,4-triazol-1-yl]tetrahydrofuran-2-one (58 mg, 0.25 mmol) in 1,2-dichloroethane (2 mL) at room temperature. The mixture was allowed to stir for 30 min before the reaction was carefully quenched by adding a few drops of 1 N HCl. After bubbling subsided, the thick mixture was diluted with additional 1 N HCl and extracted with $CH_2Cl_2$ (2×20 mL). The combined organic extracts were dried over $MgSO_4$, filtered, and concentrated in vacuo. The crude material was carried to the next step without further purification.

b) To a solution of the crude alcohol intermediate (assumed 0.21 mmol) from step a and triethylamine (0.10 mL, 0.63 mmol) in $CH_2Cl_2$ (3 mL) was slowly added methanesulfonyl chloride (0.025 mL, 0.32 mmol). The reaction mixture was allowed to stir at room temperature for 15 min before it was diluted with $CH_2Cl_2$ and washed with water. The organic layer was separated, dried over $MgSO_4$, filtered, and concentrated in vacuo. The crude material was carried to the next step without further purification.

c) To the crude mesylate intermediate (assumed 0.21 mmol) from step b in tetrahydrofuran (2 mL) was added sodium hydride (40 mg, 60% in mineral oil, 1.0 mmol) in one portion at room temperature. After stirring for 30 min, the reaction was quenched by the addition of saturated aqueous $NH_4Cl$ and extracted with $CH_2Cl_2$ (2×20 mL). The organic layers were combined, dried over $MgSO_4$, filtered, and concentrated in vacuo. The crude residue was purified by reverse phase HPLC (C18 column, acetonitrile $H_2O$ with 0.1% TFA as eluent) to afford the titled compound (20 mg, 0.045 mmol, 22% over three steps) as a white solid. $^1H$ NMR (400 MHz, $CDCl_3$) δ 7.66 (s, 1H), 7.42 (dd, J=8.8, 4.8 Hz, 2H), 7.18 (dd, J=8.4, 8.4 Hz, 2H), 5.06 (dd, J=9.1, 6.0 Hz, 1H), 4.05 (ddd, J=9.6, 8.4, 5.3 Hz, 1H), 3.90 (ddd, J=9.6, 8.0, 5.5 Hz, 1H), 2.85 (dddd, J=13.6, 8.0, 5.6, 5.6 Hz, 1H), 2.75 (dddd, J=13.6, 8.0, 8.0, 5.2 Hz, 1H), 2.42 (s, 3H), 2.21 (s, 3H); MS: (ES) m/z calculated for $C_{19}H_{16}ClF_4N_5O$ $[M+H]^+$ 442.1, found 442.1.

Example 3

Synthesis of 1-[1-(4-fluorophenyl)-5-methylpyrazol-4-yl]-3-[2-methyl-4-(trifluoromethyl)imidazol-1-yl]pyrrolidin-2-one

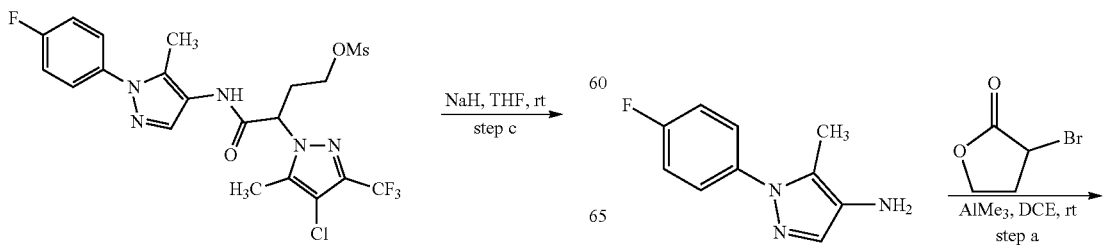

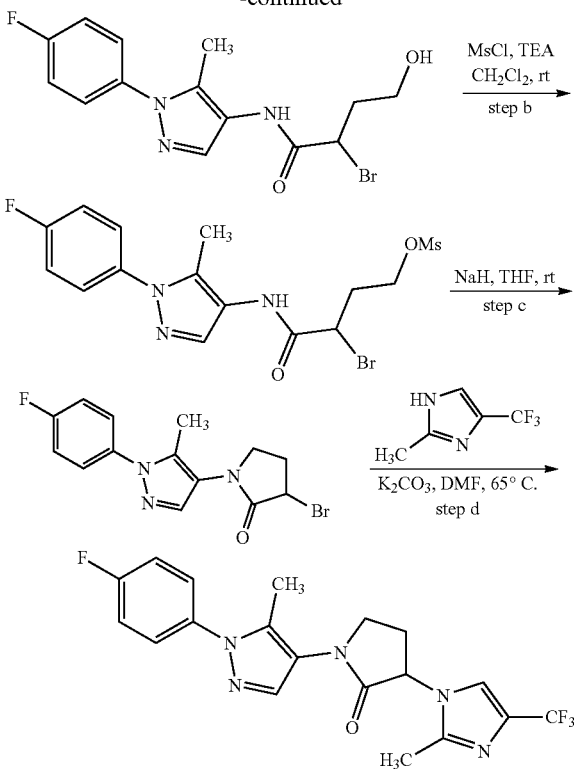

a) Trimethylaluminum (0.26 mL, 2 M in toluene, 0.52 mmol) was slowly added under nitrogen to a solution of the 1-(4-fluorophenyl)-5-methylpyrazol-4-amine (50 mg, 0.26 mmol) and α-bromo-γ-butyrolactone (85 mg, 0.52 mmol) in 1,2-dichloroethane (2 mL) at room temperature. The mixture was allowed to stir for 1 h before the reaction was carefully quenched by adding a few drops of 1 N HCl. After bubbling subsided, the thick mixture was diluted with additional 1 N HCl and extracted with CH$_2$Cl$_2$ (2×20 mL). The combined organic extracts were dried over MgSO$_4$, filtered, and concentrated in vacuo. The crude material was carried to the next step without further purification.

b) To a solution of the crude alcohol intermediate (assumed 0.26 mmol) from step a and triethylamine (0.11 mL, 0.78 mmol) in CH$_2$Cl$_2$ (3 mL) was slowly added methanesulfonyl chloride (0.030 mL, 0.39 mmol). The reaction mixture was allowed to stir at room temperature for 15 min before it was diluted with CH$_2$Cl$_2$ and washed with water. The organic layer was separated, dried over MgSO$_4$, filtered, and concentrated in vacuo. The crude material was carried to the next step without further purification.

c) To the crude mesylate intermediate (assumed 0.61 mmol) from step b in tetrahydrofuran (2 mL) was added sodium hydride (40 mg, 60% in mineral oil, 1.0 mmol) in one portion at room temperature. After stirring for 30 min, the reaction was quenched by the addition of saturated aqueous NH$_4$Cl and extracted with CH$_2$Cl$_2$ (2×20 mL). The organic layers were combined, dried over MgSO$_4$, filtered, and concentrated in vacuo. The crude material was carried to the next step without further purification.

d) A mixture of the crude bromide intermediate (assumed 0.26 mmol) from step c, 2-methyl-4-trifluoromethylimidazole (40 mg, 0.26 mmol), and potassium carbonate (40 mg, 0.29 mmol) in DMF (2 mL) was stirred at 65° C. for 12 h. The mixture was cooled to room temperature, diluted with EtOAc (20 mL) and washed with water. The aqueous layer was back-extracted with EtOAc (1×10 mL) and CH$_2$Cl$_2$ (1×10 mL). The organic layers were combined, dried over MgSO$_4$, filtered, and concentrated in vacuo. Purification of the crude material by reverse phase HPLC (C18 column, acetonitrile H$_2$O with 0.1% TFA as eluent) afforded the trifluoroacetate salt of the titled compound (28 mg, 0.0054 mmol, 21% over four steps) as a white solid. $^1$H NMR (400 MHz, CDCl$_3$) δ 7.69 (s, 1H), 7.43 (dd, J=8.8, 4.8 Hz, 2H), 7.30-7.28 (m, 1H), 7.21 (dd, J=8.0, 8.0 Hz, 2H), 5.07 (dd, J=10.4, 8.8 Hz, 1H), 3.98 (ddd, J=10.0, 10.0, 6.8 Hz, 1H), 3.89 (ddd, J=10.8, 9.2, 2.0 Hz, 1H), 2.94-2.88 (m, 1H), 2.61 (s, 3H), 2.48-2.39 (m, 1H), 2.27 (s, 3H); MS: (ES) m/z calculated for C$_{19}$H$_{17}$F$_4$N$_5$O [M+H]$^+$408.1, found 408.1.

Example 4

Synthesis of 1-[1-(4-fluorophenyl)-5-methylpyrazol-4-yl]-3-[2-methyl-4-(trifluoromethyl)imidazol-1-yl] piperidin-2-one

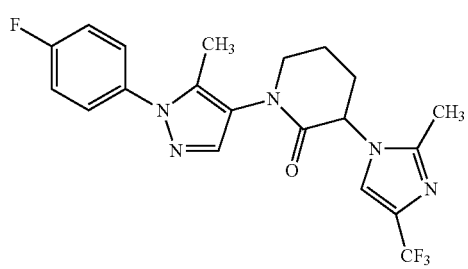 [SMILES: Cc1nc(C(F)(F)F)cn1C1CCCN(c2cnn(-c3ccc(F)cc3)c2C)C1=O]

The titled compound was prepared using the procedure as described for Example 3, substituting α-bromo-γ-butyrolactone for 3-bromotetrahydropyran-2-one in step 3a. $^1$H NMR (400 MHz, CDCl$_3$) δ 7.66 (s, 1H), 7.40 (dd, J=9.2, 4.8 Hz, 2H), 7.29-7.26 (m, 1H), 7.19 (t, J=8.0 Hz, 2H), 4.89 (dd, J=11.2, 5.6 Hz, 1H), 3.88 (J=12.4, 10.4, 4.8 Hz, 1H), 3.80-3.73 (m, 1H), 2.60 (s, 3H). 2.60-2.53 (m, 1H), 2.40-2.23 (m, 3H), 2.15 (s, 3H); MS: (ES) m/z calculated for C$_{20}$H$_{19}$F$_4$N$_5$O [M+H]$^+$422.2, found 422.1.

Example 5

Synthesis of 3-[4-chloro-5-methyl-3-(trifluoromethyl)pyrazol-1-yl]-1-[1-(4-fluorophenyl)pyrazol-4-yl]pyrrolidin-2-one

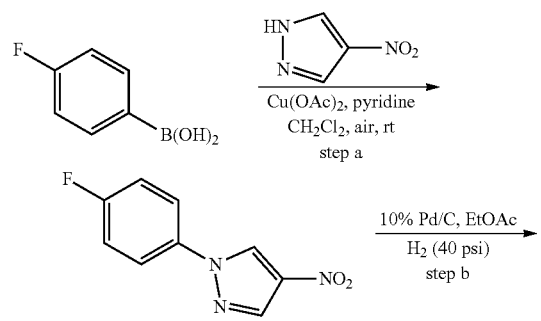

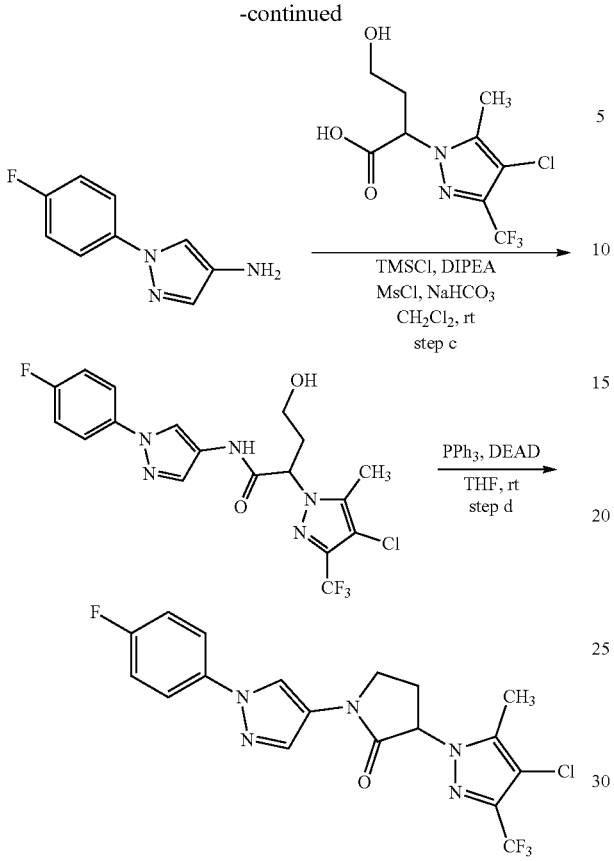

a) A solution of 4-fluorophenylboronic acid (5.02 g, 35.4 mmol), 4-nitro-1H-pyrazole (2.00 g, 17.7 mmol), copper acetate (3.50 g, 19.5 mmol), and pyridine (7.00 mL, 88.5 mmol) in CH$_2$Cl$_2$ (100 mL) was allowed to stir under air at room temperature for 12 h. The mixture was then filtered through a pad of Celite and the filtrate was concentrated in vacuo. The crude residue was purified by flash chromatography (SiO$_2$, 30% EtOAc/hexanes) to afford the product as a white solid.

b) A heavy-walled glass flask containing 1-(4-fluorophenyl)-4-nitro-pyrazole (assumed 17.7 mmol) from step a and 10% Pd/C (0.30 g) in EtOH (50 mL) and EtOAc (10 mL) was fitted onto a Parr apparatus and agitated under H$_2$ at 40 psi. After 1 h, the reaction mixture was filtered through a pad of Celite and the filtrate was concentrated in vacuo to afford the product as a red solid (4.0 g, 22.6 mmol, 63% over two steps). The product was used without further purification.

c) To a solution of 2-[4-chloro-5-methyl-3-(trifluoromethyl)pyrazol-1-yl]-4-hydroxy-butanoic acid (0.77 g, 2.7 mmol) and N,N-diisopropylethylamine (1.9 mL, 11 mmol) in CH$_2$Cl$_2$ (30 mL) was added trimethylsilylchloride (0.85 mL, 6.8 mmol) at room temperature. The mixture was allowed to stir for 5 min before the addition of methanesulfonyl chloride (0.52 mL, 6.8 mL). After stirring for an additional 10 min, sodium bicarbonate (0.45 g, 5.4 mmol) and 1-(4-fluorophenyl)pyrazol-4-amine (0.32 g, 1.8 mmol) from step a were each added as solids. The mixture was left to stir at room temperature for 12 h. The reaction was quenched by the addition of 1 N HCl (30 mL) and extracted with CH$_2$Cl$_2$ (1×50 mL). The organic layers were combined, dried over MgSO$_4$, filtered, and concentrated in vacuo. Purification of the crude material by flash chromatography (SiO$_2$, 20%-50% EtOAc/hexanes) afforded the product as an orange oil (140 mg, 0.31 mmol, 18%).

d) Diethyl azodicarboxylate (75 μL, 0.47 mmol) was slowly added to a solution of triphenylphosphine (124 mg, 0.47 mmol) in tetrahydrofuran (2 mL) under nitrogen. The yellow solution was allowed to stir for 20 min at room temperature before the alcohol intermediate (140 mg, 0.30 mmol) from step c was added as a solution in tetrahydrofuran (3 mL). After stirring overnight at room temperature, the reaction was quenched by the addition of saturated aqueous NaHCO$_3$ and the mixture was extracted with CH$_2$Cl$_2$ (2×20 mL). The organic layers were combined, dried over MgSO$_4$, filtered, and concentrated in vacuo. The crude material was purified by flash chromatography (SiO$_2$, 20-50% EtOAc/hexanes) and reverse phase HPLC (C18 column, acetonitrile-H$_2$O with 0.1% TFA as eluent) to afford the titled compound (10 mg, 0.023 mmol, 8%) as a white solid. $^1$H NMR (400 MHz, CDCl$_3$) δ 8.46 (s, 1H), 7.74 (s, 1H), 7.64 (dd, J=9.2, 4.8 Hz, 2H), 7.15 (dd, J=8.8, 8.0 Hz, 2H), 5.12 (dd, J=9.3, 7.5 Hz, 1H), 4.12 (ddd, J=9.2, 9.2, 3.9 Hz, 1H), 3.97-3.86 (m, 1H), 3.10 (dddd, J=14.0, 8.8, 6.8, 0.4 Hz, 1H), 2.77 (dddd, J=13.2, 9.6, 7.6, 3.6 Hz, 1H), 2.44 (s, 3H); MS: (ES) m/z calculated for C$_{18}$H$_{14}$ClF$_4$N$_5$O [M+H]$^+$ 428.1, found 428.1.

Example 6

Synthesis of 1-[1-(4-fluorophenyl)pyrazol-4-yl]-3-[2-methyl-4-(trifluoromethyl)imidazol-1-yl]pyrrolidin-2-one

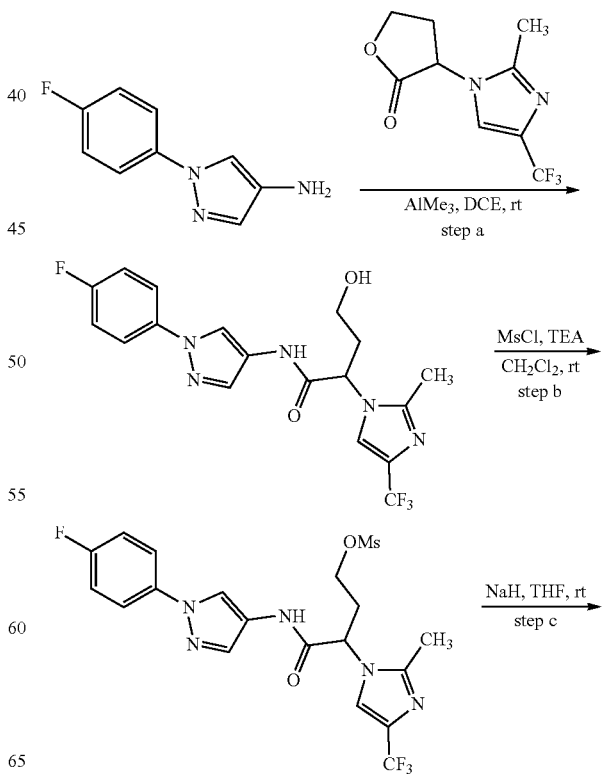

-continued

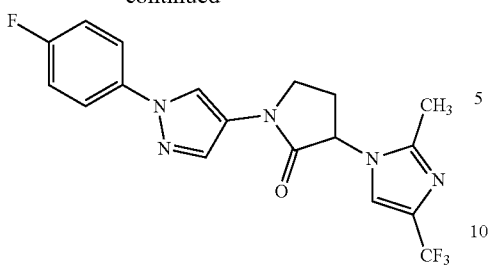

a) Trimethylaluminum (1.4 mL, 2 M in toluene, 2.8 mmol) was slowly added under nitrogen to a solution of 1-(4-fluorophenyl)pyrazol-4-amine (0.24 g, 1.4 mmol) and 3-[2-methyl-4-(trifluoromethyl)imidazol-1-yl]tetrahydrofuran-2-one (0.32 g, 1.4 mmol) in 1,2-dichloroethane (2 mL) at room temperature. The mixture was allowed to stir for 30 min before the reaction was carefully quenched by adding a few drops of 1 N HCl. After bubbling subsided, the thick mixture was diluted with additional 1 N HCl and extracted with $CH_2Cl_2$ (3×20 mL). The combined organic extracts were dried over $MgSO_4$, filtered, and concentrated in vacuo. The crude material was carried to the next step without further purification.

b) To a solution of the crude alcohol intermediate (89 mg 0.21 mmol) from step a and triethylamine (90 µL, 0.65 mmol) in $CH_2Cl_2$ (2 mL) was slowly added methanesulfonyl chloride (25 µL, 0.31 mmol). The reaction mixture was allowed to stir at room temperature for 1 h before it was diluted with $CH_2Cl_2$ and washed with water. The organic layer was separated, dried over $MgSO_4$, filtered, and concentrated in vacuo. The crude material was carried to the next step without further purification.

c) To the crude mesylate intermediate (assumed 0.21 mmol) from step b in tetrahydrofuran (2 mL) was added sodium hydride (30 mg, 60% in mineral oil, 0.65 mmol) in one portion at room temperature. After stirring for 30 min, the reaction was quenched by the addition of saturated aqueous $NH_4Cl$ and extracted with $CH_2Cl_2$ (2×20 mL). The organic layers were combined, dried over $MgSO_4$, filtered, and concentrated in vacuo. The crude material was purified by reverse phase HPLC (C18 column, acetonitrile-$H_2O$ with 0.1% TFA as eluent) to afford the trifluroacetate salt of the titled compound (24 mg, 0.047 mmol, 20% over two steps) as a white solid. $^1$H NMR (400 MHz, $CDCl_3$) δ 8.53 (s, 1H), 7.76 (s, 1H), 7.66 (dd, J=9.0, 4.5 Hz, 2H), 7.27-7.25 (m, 2H), 7.15 (dd, J=9.2, 8.4 Hz, 2H), 5.07 (dd, J=9.5, 9.5 Hz, 1H), 4.05-3.91 (m, 1H), 2.97 (dddd, J=13.6, 8.4, 6.8, 2.0 Hz, 1H), 2.59 (s, 3H), 2.42 (dddd, J=13.6, 9.6, 3.6, 3.6 Hz, 1H); MS: (ES) m/z calculated for $C_{18}H_{15}ClF_4N_5O$ [M+H]$^+$394.1, found 394.1.

Example 7

Synthesis of 1-[1-(4-fluorophenyl)pyrazol-4-yl]-3-[5-methyl-3-(trifluoromethyl)pyrazol-1-yl]pyrrolidin-2-one

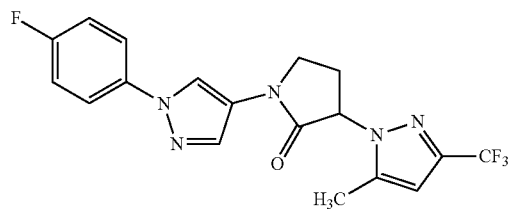 [SMILES: Cc1cc(C(F)(F)F)nn1C1CCN(c2cnn(-c3ccc(F)cc3)c2)C1=O]

The titled compound was prepared using the procedure as described for Example 6, substituting 3-[2-methyl-4-(trifluoromethyl)imidazol-1-yl]tetrahydrofuran-2-one for 3-[5-methyl-3-(trifluoromethyl)pyrazol-1-yl]tetrahydrofuran-2-one in step 6a. $^1$H NMR (400 MHz, $CDCl_3$) δ 8.46 (s, 1H), 7.74 (s, 1H), 7.64 (dd, J=8.8, 4.4 Hz, 2H), 7.14 (dd, J=9.2, 8.4 Hz, 2H), 6.35 (s, 1H), 5.11 9 (dd, J=8.8, 4.4 Hz, 1H), 4.13 (ddd, J=9.2, 9.2, 4.0 Hz, 1H), 3.90 (ddd, J=9.6, 8.0, 6.8 Hz, 1H), 3.10 (dddd, J=13.2, 8.8, 7.2, 7.2 Hz, 1H), 2.78 (dddd, J=13.2, 9.2, 8.0, 3.6 Hz, 1H), 2.46 (s, 3H); MS: (ES) m/z calculated for $C_{19}H_{15}F_4N_5O$ [M+H]$^+$394.1, found 394.1.

Example 8

Synthesis of 3-[4-chloro-5-methyl-3-(trifluoromethyl)pyrazol-1-yl]-1-[1-(4-fluorophenyl)pyrazol-4-yl]piperidin-2-one

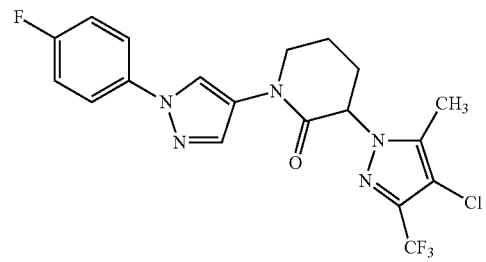 [SMILES: Cc1c(Cl)c(C(F)(F)F)nn1C1CCCN(c2cnn(-c3ccc(F)cc3)c2)C1=O]

The titled compound was prepared using the procedure as described for Example 6, substituting 3-[2-methyl-4-(trifluoromethyl)imidazol-1-yl]tetrahydrofuran-2-one for 3-[4-chloro-5-methyl-3-(trifluoromethyl)pyrazol-1-yl]tetrahydropyran-2-one in step 6a. $^1$H NMR (400 MHz, $CDCl_3$) δ 8.40 (s, 1H), 7.75 (s, 1H), 7.61 (dd, J=9.0, 4.5 Hz, 2H), 7.12 (dd, J=8.0, 8.0 Hz, 2H), 4.92 (dd, J=11.2, 5.8 Hz, 1H), 3.98-3.85 (m, 2H), 2.88-2.72 (m, 1H), 2.46-2.35 (m, 1H), 2.38 (s, 3H), 2.23-2.10 (m, 2H); MS: (ES) m/z calculated for $C_{19}H_{16}ClF_4N_5O$ [M+H]$^+$442.1, found 442.1.

Example 9

Synthesis of 1-[1-(4-fluorophenyl)pyrazol-4-yl]-3-[2-methyl-4-(trifluoromethyl)imidazol-1-yl]piperidin-2-one

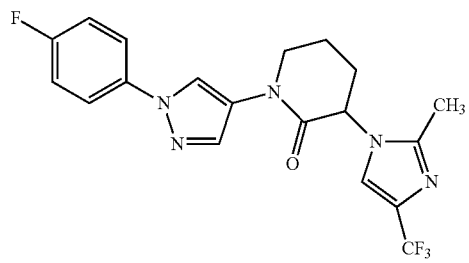 [SMILES: Cc1nc(C(F)(F)F)cn1C1CCCN(c2cnn(-c3ccc(F)cc3)c2)C1=O]

The titled compound was prepared using the procedure as described for Example 6, substituting 3-[2-methyl-4-(trifluoromethyl)imidazol-1-yl]tetrahydrofuran-2-one for 3-[2-methyl-4-(trifluoromethyl)imidazol-1-yl]tetrahydropyran-2-one for in step 6a. $^1$H NMR (400 MHz, CDCl$_3$) δ 8.54 (s, 1H), 7.76 (s, 1H), 7.63 (dd, J=8.8, 4.8 Hz, 2H), 7.25-7.22 (m, 1H), 7.15 (dd, J=8.0, 8.0 Hz, 2H), 4.87 (dd, J=11.5, 5.7 Hz, 1H), 4.00-3.88 (m, 2H), 2.61 (s, 3H), 2.56-2.50 (m, 1H), 2.46-2.37 (m, 1H), 2.37-2.20 (m, 2H); MS: (ES) m/z calculated for C$_{19}$H$_{17}$F$_4$N$_5$O [M+H]$^+$408.1, found 408.1.

Example 10

Synthesis of 1-[1-(4-fluorophenyl)pyrazol-4-yl]-3-[5-methyl-3-(trifluoromethyl)pyrazol-1-yl]piperidin-2-one

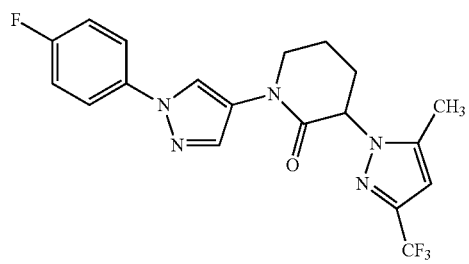 [SMILES: Cc1cc(C(F)(F)F)nn1C1CCCN(c2cnn(-c3ccc(F)cc3)c2)C1=O]

The titled compound was prepared using the procedure as described for Example 6, substituting 3-[2-methyl-4-(trifluoromethyl)imidazol-1-yl]tetrahydrofuran-2-one for 3-[5-methyl-3-(trifluoromethyl)pyrazol-1-yl]tetrahydropyran-2-one in step 6a. $^1$H NMR (400 MHz, CDCl$_3$) δ 8.55 (s, 1H), 7.74 (s, 1H), 7.61 (ddd, J=9.2, 4.8, 2.0 Hz, 2H), 7.12 (dd, J=9.2, 8.0 Hz, 2H), 6.34 (s, 1H), 4.93 (dd, J=11.2, 5.7 Hz, 1H), 3.99-3.84 (m, 2H), 2.81 (dddd, J=13.6, 11.6, 10.4, 2.8 Hz, 1H), 2.46-2.35 (m, 2H), 2.42 (s, 3H), 2.17 (dddd, J=13.6, 10.4, 6.8, 2.8 Hz, 1H); MS: (ES) m/z calculated for C$_{19}$H$_{17}$F$_4$N$_5$O [M]$^+$408.1, found 408.1.

Example 11

Synthesis of 3-[4-chloro-5-methyl-3-(trifluoromethyl)pyrazol-1-yl]-1-[5-ethyl-1-(4-fluorophenyl)pyrazol-4-yl]pyrrolidin-2-one

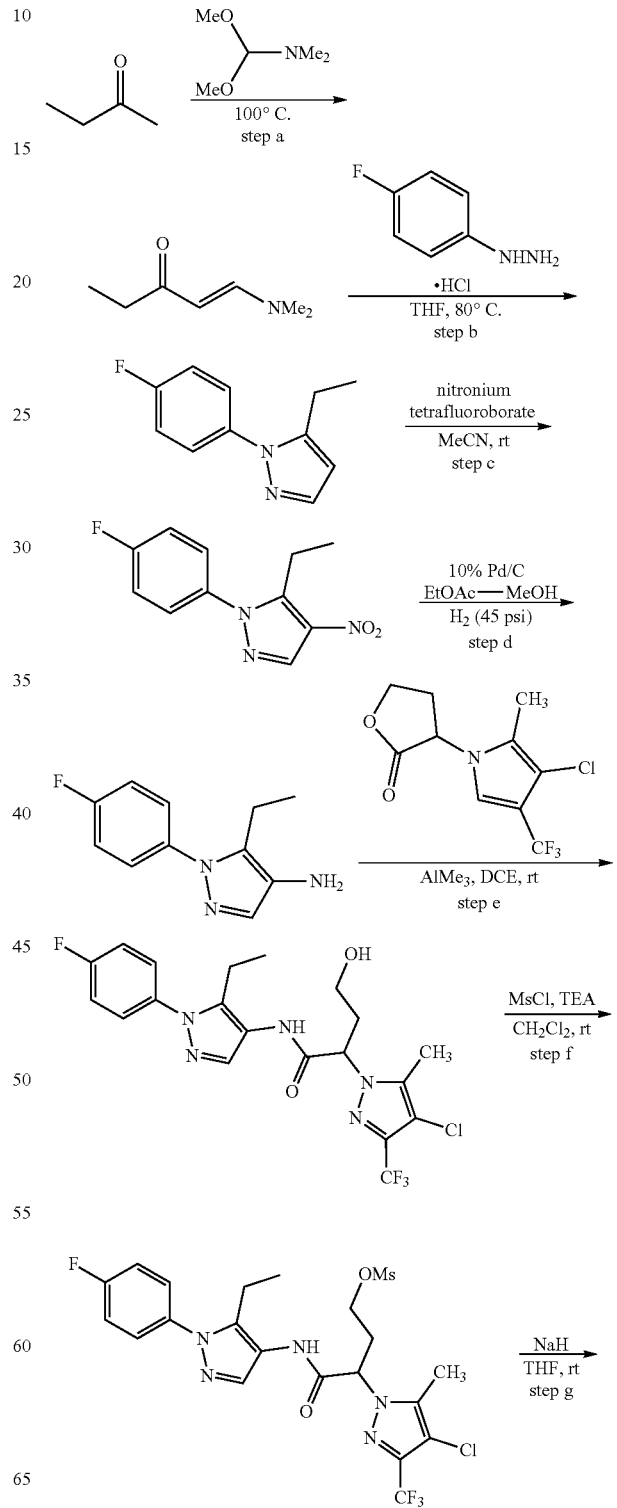

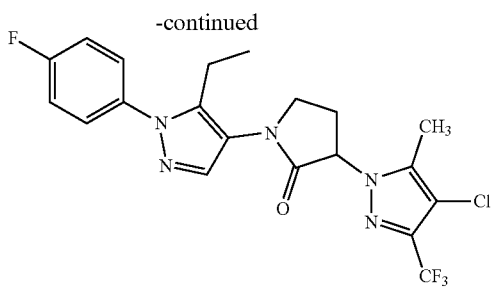

a) A mixture of 2-butanone (1.10 g, 15.3 mmol) and N,N-dimethylformamide dimethyl acetal (2.20 g, 18.3 mmol) was heated at 110° C. for 1 d. After cooling, the crude reaction mixture was carried directly to the next step.

b) A solution of 4-fluorophenylhydrazine hydrochloride (2.50 g, 15.3 mmol) and 1-(dimethylamino)pent-1-en-3-one (assumed 15.3 mmol) from step a in tetrahydrofuran (5 mL) was heated at 85° C. for 1 d. After cooling to room temperature, the mixture was diluted with $CH_2Cl_2$ (50 mL) and washed with water. The organic layer was dried over $MgSO_4$, filtered, and concentrated in vacuo. Purification of the crude material by flash chromatography ($SiO_2$, 0-20% EtOAc/hexanes) afforded the product (1.1 g, 5.8 mmol, 37%) as a red oil.

c) Nitronium tetrafluoroborate (500 mg, 2.3 mmol) was added to a solution of 5-ethyl-1-(4-fluorophenyl)pyrazole (420 mg, 3.2 mmol) from step b in anhydrous acetonitrile (10 mL) under nitrogen at room temperature. After stirring for 12 h, the mixture was concentrated in vacuo and purified by flash chromatography ($SiO_2$, 50% EtOAc/hexanes) to give the product (53 mg, 0.023 mmol, 9%) as a yellow oil.

d) A heavy-walled glass flask containing the product (53 mg, 0.023 mmol) from step c and 10% Pd/C (11 mg, 20 wt %) in MeOH (1 mL) and EtOAc (2 mL) was fitted onto a Parr apparatus and agitated under $H_2$ at 45 psi. After 1.5 h, the reaction mixture was filtered through a pad of Celite and the filtrate was concentrated in vacuo to afford the product (45 mg, 0.023 mmol, 99%) as a yellow solid. The crude material was carried to the next step without further purification.

e) Trimethylaluminum (0.2 mL, 2 M in toluene, 0.39 mmol) was slowly added under nitrogen to a solution of 5-ethyl-1-(4-fluorophenyl)pyrazol-4-amine (45 mg, 0.023 mmol) from step d and 3-[4-chloro-5-methyl-3-(trifluoromethyl)pyrazol-1-yl]tetrahydrofuran-2-one (76 mg, 0.28 mmol) in 1,2-dichloroethane (3 mL) at room temperature. The mixture was allowed to stir for 30 min before the reaction was carefully quenched by adding a few drops of 1 N HCl. After bubbling subsided, the thick mixture was diluted with more 1 N HCl and extracted with $CH_2Cl_2$ (3×10 mL). The combined organic extracts were dried over $MgSO_4$, filtered, and concentrated in vacuo. The crude material was carried to the next step without further purification.

(g) To a solution of the crude alcohol intermediate (assumed 0.23 mmol) from step e and triethylamine (110 µL, 0.78 mmol) in $CH_2Cl_2$ (2 mL) was slowly added methanesulfonyl chloride (25 µL, 0.31 mmol). The reaction mixture was allowed to stir at room temperature for 1 h before it was diluted with $CH_2Cl_2$ and washed with water. The organic layer was separated, dried over $MgSO_4$, filtered, and concentrated in vacuo. The crude material was carried to the next step without further purification.

g) To the crude mesylate intermediate (assumed 0.23 mmol) from step f in tetrahydrofuran (2 mL) was added sodium hydride (30 mg, 60% in mineral oil, 0.65 mmol) in one portion at room temperature. After stirring for 30 min, the reaction was quenched by the addition of saturated aqueous $NH_4Cl$ and extracted with $CH_2Cl_2$ (2×20 mL). The organic layers were combined, dried over $MgSO_4$, filtered, and concentrated in vacuo. The crude material was purified by reverse phase HPLC (C18 column, acetonitrile-$H_2O$ with 0.1% TFA as eluent) to afford the titled compound (51 mg, 0.11 mmol, 48% over three steps) as a white solid. $^1$H NMR (400 MHz, $CDCl_3$) δ 7.60 (s, 1H), 7.40 (dd, J=8.9, 4.8 Hz, 2H), 7.17 (dd, J=8.4, 8.4 Hz, 2H), 5.04 (dd, J=9.1, 5.8 Hz, 1H), 4.06 (ddd, J=9.8, 8.4, 5.4 Hz, 1H), 3.87 (ddd, J=9.7, 8.2, 5.3 Hz, 1H), 2.86 (dddd, J=14.0, 84, 8.4, 6.0 Hz, 1H), 2.74 (dddd, J=14.4, 9.2, 8.8, 5.6 Hz, 1H), 2.65 (dddd, J=15.2, 7.6, 7.6, 1.2 Hz, 2H), 2.43 (s, 3H). 0.97 (t, J=7.6 Hz, 3H); MS: (ES) m/z calculated for $C_{20}H_{18}ClF_4N_5O$ [M+H]$^+$ 456.1, found 456.1.

Example 12

Synthesis of 3-[4-chloro-5-methyl-3-(trifluoromethyl)pyrazol-1-yl]-1-[1-(4-fluorophenyl)-5-isopropyl-pyrazol-4-yl]pyrrolidin-2-one

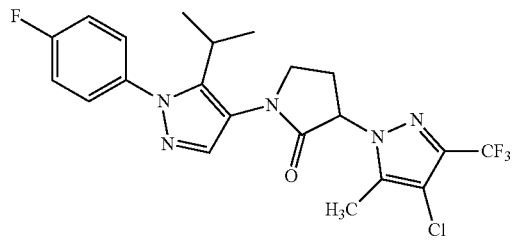 [SMILES: Cc1c(Cl)c(C(F)(F)F)nn1C1CCN(c2cnn(-c3ccc(F)cc3)c2C(C)C)C1=O]

The titled compound was prepared using the procedure as described for Example 2, substituting 1-(4-fluorophenyl)-5-methyl-pyrazol-4-amine for 1-(4-fluorophenyl)-5-isopropyl-pyrazol-4-amine in step 2a. $^1$H NMR (400 MHz, $CDCl_3$) δ 7.55 (s, 1H), 7.38 (dd, J=8.9, 4.8 Hz, 2H), 7.18 (dd, J=8.5, 8.5 Hz, 2H), 5.04 (dd, J=9.3, 5.9 Hz, 1H), 4.04 (ddd, J=10.0, 8.8, 5.2 Hz, 1H), 3.82 (ddd, J=10.0, 8.4, 5.6 Hz, 1H), 3.01-2.92 (m, 1H), 2.92-2.84 (m, 1H), 2.80-2.69 (m, 1H), 2.42 (s, 3H), 1.21 (d, J=6.8, 3H), 1.11 (d, J=6.8, 3H); MS: (ES) m/z calculated for $C_{21}H_{20}ClF_4N_5O$ [M+H]$^+$ 470.1, found 470.1.

Example 13

Synthesis of 1-[5-tert-butyl-1-(4-fluorophenyl)pyrazol-4-yl]-3-[4-chloro-5-methyl-3-(trifluoromethyl)pyrazol-1-yl]pyrrolidin-2-one

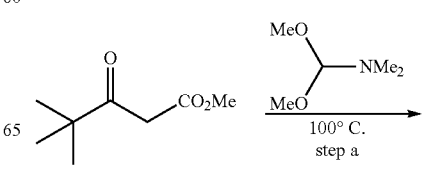

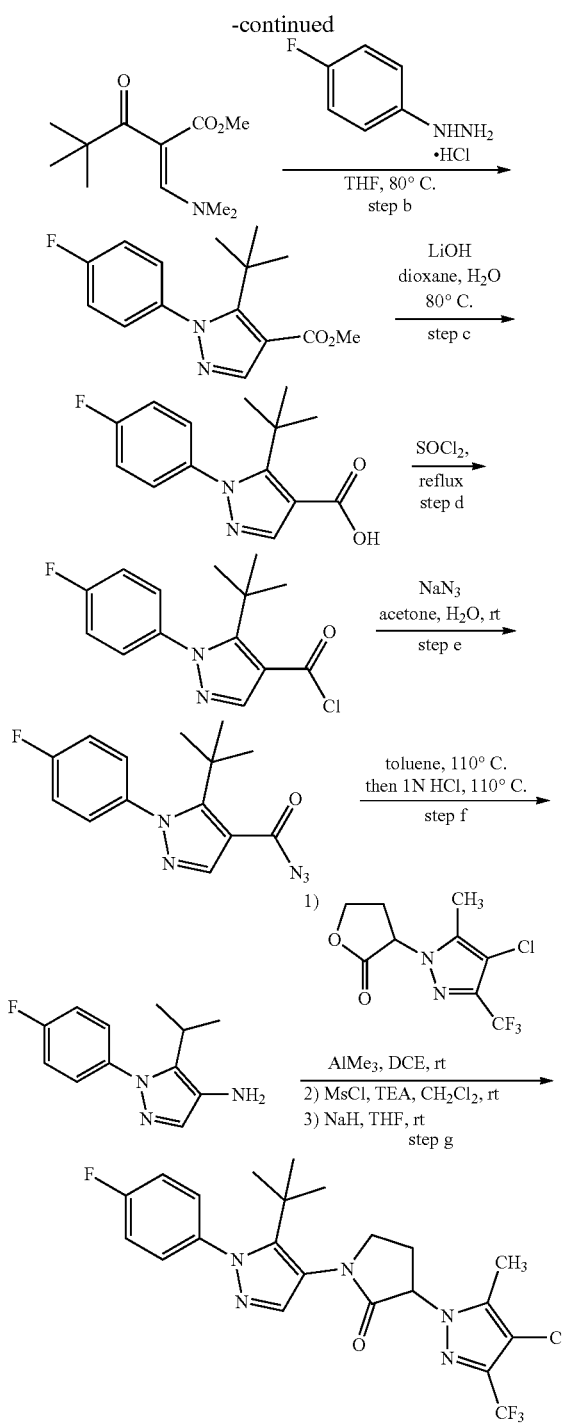

a) A mixture of pivaloylacetic acid methyl ester (5.80 g, 36.7 mmol) and N,N-dimethylformamide dimethyl acetal (5.24 g, 44.0 mmol) was heated at 110° C. for 1 d. After cooling, the reaction mixture was concentrated in vacuo to remove any volatiles and the crude material was carried directly on to the next step.

b) A solution of 4-fluorophenylhydrazine hydrochloride (5.97 g, 36.7 mmol) and methyl-2-(dimethylaminomethylene)-4,4-dimethyl-3-oxopentanoate (assumed 36.7 mmol) from step a in tetrahydrofuran (15 mL) was heated at 85° C. for 1 h. After cooling to room temperature, the mixture was diluted with CH$_2$Cl$_2$ (50 mL) and washed with water. The organic layer was dried over MgSO$_4$, filtered, and concentrated in vacuo. Purification of the crude material by flash chromatography (SiO$_2$, 0-20% EtOAc/hexanes) afforded the product (5.0 g, 18.1 mmol, 50% over two steps) as a red oil.

c) A biphasic solution of methyl 5-tert-butyl-1-(4-fluorophenyl)pyrazole-4-carboxylate (5.00 g, 18.1 mmol) from step b, lithium hydroxide monohydrate (2.77 g, 66.0 mmol) in dioxane (20 mL) and water (20 mL) was heated at 80° C. with stirring for 1.5 h. After cooling, the mixture was diluted with 1 N HCl and extracted with CH$_2$Cl$_2$ (1×100 mL). The organic layer was dried over MgSO$_4$, filtered, and concentrated in vacuo. The crude brown solid was used without further purification d) A solution of 5-tert-butyl-1-(4-fluorophenyl)pyrazole-4-carboxylic acid (0.67 g, 2.6 mmol) from step c in thionyl choride (2.0 mL) was heated to reflux with stirring for 20 min. The reaction mixture was cooled to room temperature and concentrated in vacuo. The crude material was azeotroped with toluene (2×10 mL) and placed under high vacuum for several hours before it was used in the next step.

e) To a solution of 5-tert-butyl-1-(4-fluorophenyl)pyrazole-4-carbonyl chloride (assumed 2.6 mmol) from step d in acetone (15 mL) was rapidly added a solution of sodium azide (0.50 g, 7.7 mmol) in water (2 mL). The mixture was stirred rigorously for 5 min at room temperature, whereby precipitation appeared. Filtration of the mixture afforded the product (0.49 g, 1.7 mmol) as a gray solid.

f) A solution of the acyl azide intermediate (86 mg, 0.030 mmol) from step e in toluene (0.5 mL) was heated at 110° C. for 10 min before 1 N HCl (0.7 mL) was added and the biphasic mixture was heated at 110° C. overnight. After cooling, the mixture was extracted with chloroform (2×10 mL). The combined organic layers were dried over MgSO$_4$, filtered, and concentrated in vacuo. Purification of the crude material by flash chromatography (SiO$_2$, 5% MeOH/CH$_2$Cl$_2$) afforded the product (40 mg, 0.017 mmol, 57%) as a brown semisolid.

g) The material from step f was used in a procedure analogous to Example 2, substituting 1-(4-fluorophenyl)-5-methylpyrazol-4-amine for 5-tert-butyl-1-(4-fluorophenyl) pyrazol-4-amine in step 2a to afford the titled compound. $^1$H NMR (400 MHz, CDCl$_3$) δ 7.54 (s, 1H), 7.38 (dd, J=9.2, 4.8 Hz, 2H), 7.16 (dd, J=8.4, 8.4 Hz, 2H), 5.09-5.00 (m, 1H), 4.08-3.99 (m, 1H), 3.83 (dq, J=8.0, 8.0, 6.0 Hz, 1H), 3.04-2.87 (m, 1H), 2.80-2.67 (m, 1H), 2.42 (s, 3H), 1.17 (s, 9H); MS: (ES) m/z calculated for C$_{22}$H$_{22}$ClF$_4$N$_5$O [M+H]$^+$ 484.1, found 484.1.

Example 14

Synthesis of 3-[4-chloro-5-methyl-3-(trifluoromethyl)pyrazol-1-yl]-1-[1-(4-fluorophenyl)-5-[(E)-1-methylprop-1-enyl]pyrazol-4-yl]pyrrolidin-2-one

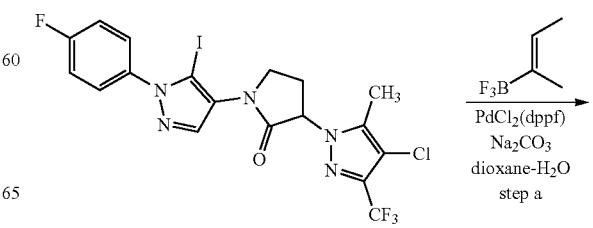

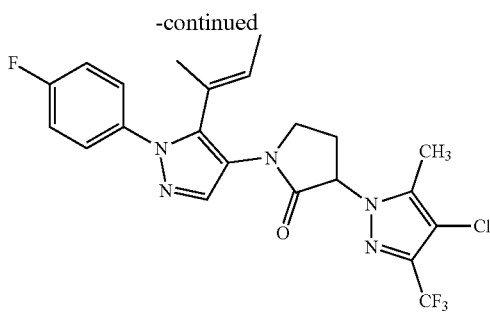

a) The starting material 3-[4-chloro-5-methyl-3-(trifluoromethyl)pyrazol-1-yl]-1-[1-(4-fluorophenyl)-5-iodo-pyrazol-4-yl]pyrrolidin-2-one was prepared from a procedure analogous to Example 2, substituting 1-(4-fluorophenyl)-5-methyl-pyrazol-4-amine for 1-(4-fluorophenyl)-5-iodo-pyrazol-4-amine in step 2a. A solution containing 3-[4-chloro-5-methyl-3-(trifluoromethyl)pyrazol-1-yl]-1-[1-(4-fluorophenyl)-5-iodo-pyrazol-4-yl]pyrrolidin-2-one (90 mg, 0.16 mmol), potassium (2Z)-2-butene-2-yltrifluoroborate (32 mg, 0.20 mmol), PdCl$_2$(dppf) (6.0 mg, 0.0080 mmol), and aqueous 2 M sodium carbonate (0.25 mL, 0.49 mmol) in dioxane (5 mL) was heated to 80° C. for 2 h. After cooling to room temperature, the reaction mixture was diluted with water and extracted with CH$_2$Cl$_2$ (2×10 mL). The combined organic layers were dried over MgSO$_4$, filtered, and concentrated in vacuo. Purification of the crude material by flash chromatography (SiO$_2$, 20-50% EtOAc/hexanes) afforded the titled compound (33 mg, 0.070 mmol) as an off-white solid. $^1$H NMR (400 MHz, CDCl$_3$) δ 7.69 (s, 1H), 7.45 (dd, J=8.9, 4.8 Hz, 2H), 7.11 (dd, J=8.0, 8.0 Hz, 2H), 5.73 (dddd, J=8.4, 6.8, 6.8, 1.6 Hz, 1H), 5.02 (dd, J=9.2, 6.9 Hz, 1H), 3.94 (ddd, J=9.6, 8.8, 4.8 Hz, 1H), 3.76 (ddd, J=9.6, 7.9, 6.2 Hz, 1H), 2.92 (dddd, J=13.6, 13.6, 8.8, 6.4 Hz, 1H), 2.67 (dddd, J=13.6, 9.2, 8.0, 4.4 Hz, 1H), 2.41 (s, 3H), 1.69 (dd J=6.8, 1.2 Hz, 3H), 1.60 (dd, J=1.2, 1.2 Hz, 3H); MS: (ES) m/z calculated for C$_{22}$H$_{20}$ClF$_4$N$_5$O [M+H]$^+$482.1, found 482.1.

Example 15

Synthesis of 3-[4-chloro-5-methyl-3-(trifluoromethyl)pyrazol-1-yl]-1-[5-cyclopropyl-1-(4-fluorophenyl)pyrazol-4-yl]pyrrolidin-2-one

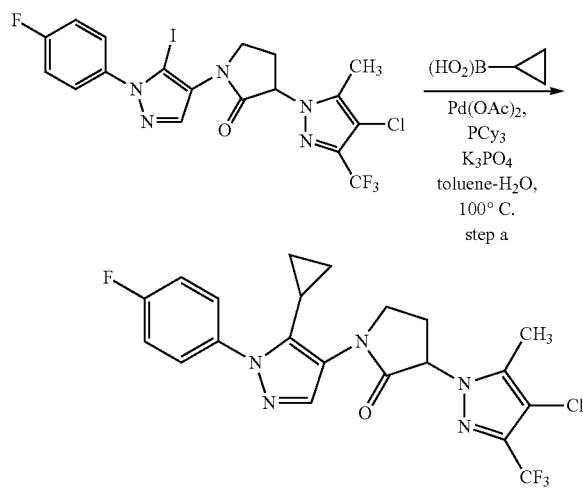

a) A solution containing 3-[4-chloro-5-methyl-3-(trifluoromethyl)pyrazol-1-yl]-1-[1-(4-fluorophenyl)-5-iodo-pyrazol-4-yl]pyrrolidin-2-one (34 mg, 0.061 mmol), cyclopropylboronic acid (7 mg, 0.08 mmol), palladium acetate (1.0 mg, 0.003 mmol), tricyclohexylphosphine (2.0 mg, 0.006 mmol) and potassium phosphate (45 mg, 0.21 mmol) in toluene (1.5 mL) and water (100 μL) was heated to 100° C. for 1 d. After cooling to room temperature, the reaction mixture was diluted with water and extracted with CH$_2$Cl$_2$ (2×10 mL). The combined organic layers were dried over MgSO$_4$, filtered, and concentrated in vacuo. The crude material was purified by reverse phase HPLC (C18 column, acetonitrile-H$_2$O with 0.1% TFA as eluent) to afford the titled compound (1.0 mg, 0.002 mmol, 3%) as a colorless residue. $^1$H NMR (400 MHz, CDCl$_3$) δ 7.61 (s, 1H), 7.54 (dd, J=9.0, 4.8 Hz, 2H), 7.16 (dd, J=9.0, 8.2 Hz, 2H), 5.06 (dd, J=9.2, 6.3 Hz, 1H), 4.11 (ddd, J=9.6, 8.4, 4.8 Hz, 1H), 3.91 (ddd, J=9.6, 8.0, 4.8 Hz, 1H), 2.98 (dddd, J=12.0, 9.6, 8.4, 6.4, 6.0 Hz, 1H), 2.74 (dddd, J=13.2, 9.2, 8.0, 4.8 Hz, 1H), 2.45 (s, 3H), 1.77 (dddd, J=8.4, 8.4, 5.6, 5.6 Hz, 1H), 0.78-0.64 (m, 2H), 0.43-0.30 (m, 2H); MS: (ES) m/z calculated for C$_{21}$H$_{18}$ClF$_4$N$_5$O [M+H]$^+$468.1, found 468.1.

Example 16

Synthesis of 3-[4-chloro-5-methyl-3-(trifluoromethyl)pyrazol-1-yl]-1-[1-(4-fluorophenyl)-5-sec-butyl-pyrazol-4-yl]pyrrolidin-2-one

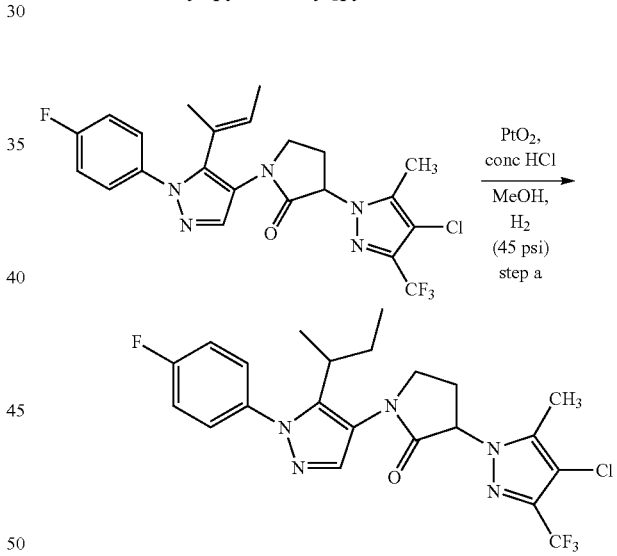

a) A heavy-walled glass flask containing the product (27 mg, 0.056 mmol) from Example 14, platinum oxide (25 mg, 0.11 mmol), and concentrated hydrochloric acid (3 drops) in MeOH (5 mL) was fitted onto a Parr apparatus and agitated under H$_2$ at 45 psi. After 2 h, the reaction mixture was filtered through a pad of Celite and the filtrate was concentrated in vacuo. Purification of the crude material by flash chromatography (SiO$_2$, 20-50% EtOAc/hexanes) afforded the titled compound (6 mg, 0.012 mmol, 22%) as a mixture of diastereomers. $^1$H NMR (400 MHz, CDCl$_3$) δ 7.53 (s, 1H), 7.35 (dd, J=8.9, 4.8 Hz, 2H), 7.17 (dd, J=8.8, 8.2 Hz, 2H), 5.02 (dd, J=9.2, 5.8 Hz, 1H), 4.02 (dddd, J=10.0, 9.2, 6.0, 5.6 Hz, 1H), 3.79 (dddd, J=10.0, 8.8, 5.6 Hz, 1H), 2.93-2.92 (m, 1H), 2.79-2.60 (m, 2H), 2.42 (s, 3H), 1.56-1.42 (m, 1H), 1.20 (d, J=7.2 Hz, 1H), 1.10 (d, J=7.2 Hz, 3H), 0.77 (t, J=7.2 Hz, 3H); MS: (ES) m/z calculated for $C_{22}H_{22}ClF_4N_5O$ [M+H]$^+$484.1, found 484.1.

Example 17

Synthesis of 3-[4-chloro-5-methyl-3-(trifluoromethyl)pyrazol-1-yl]-1-[1-(4-fluorophenyl)-5-propylpyrazol-4-yl]pyrrolidin-2-one

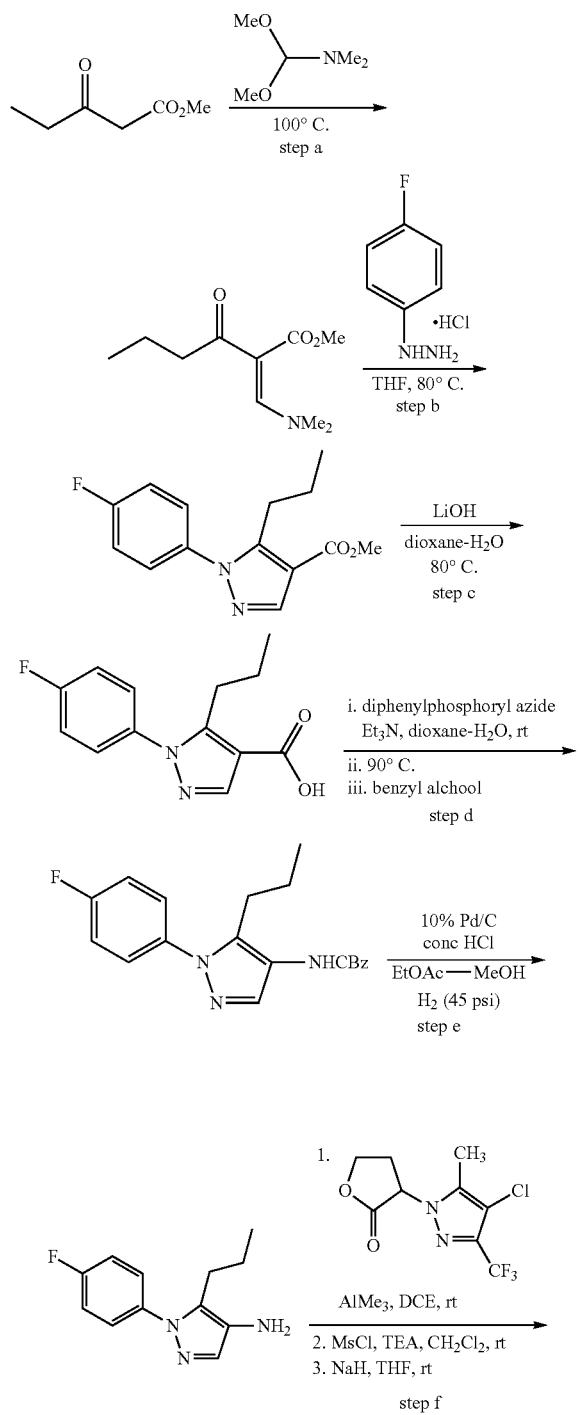

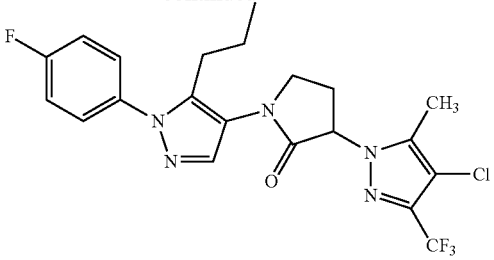

a) A mixture of methyl butyrylacetate (5.00 g, 34.7 mmol) and N,N-dimethylformamide dimethyl acetal (5.00 g, 41.6 mmol) was heated at 110° C. for 1 d. After cooling, the reaction mixture was concentrated in vacuo to remove any volatiles and the crude material carried directly to the next step.

b) A solution of 4-fluorophenylhydrazine hydrochloride (5.64 g, 34.7 mmol) and methyl-2-(dimethylaminomethylene)-4,4-dimethyl-3-oxo-hexanoate (assumed 34.7 mmol) from step a in tetrahydrofuran (25 mL) was heated at 85° C. for 1 h. After cooling to room temperature, the mixture was diluted with $CH_2Cl_2$ (50 mL) and washed with 1 N HCl (1×50 mL) and saturated aqueous $NaHCO_3$ (1×50 mL). The organic layer was dried over $MgSO_4$, filtered, and concentrated in vacuo. The crude material was carried directly to the next step.

c) A biphasic solution of methyl 1-(4-fluorophenyl)-5-propylpyrazole-4-carboxylate (assumed 34.7 mmol) from step b, and lithium hydroxide monohydrate (7.3 g, 173 mmol) in dioxane (40 mL) and water (20 mL) was heated at 80° C. with stirring for 3 h. After cooling, the mixture was acidified with 1 N HCl and extracted with $CH_2Cl_2$ (2×40 mL) and EtOAc (2×40 mL). The combined organic layers were dried over $MgSO_4$, filtered, and concentrated in vacuo. The crude material was purified by flash chromatography ($SiO_2$, 20-50% EtOAc/hexanes) to afford the product (6.65 g, 26.5 mmol, 76%) as a red oil.

d) To a solution of 1-(4-fluorophenyl)-5-propylpyrazole-4-carboxylic acid (0.76 g, 3.1 mmol) from step c in dioxane (8 mL) was added triethylamine (0.47 mmol, 3.4 mmol) and diphenylphosphoryl azide (0.65 mL, 3.1 mmol). The mixture was left to stir for 2 h at room temperature before it was heated to 90° C. and stirred for 30 min. The reaction was cooled to room temperature and benzyl alcohol (0.63 mL, 6.1 mmol) was added. The mixture was reheated to 90° C. and stirred at that temperature overnight. After cooling, the mixture was diluted with diethyl ether (50 mL) and washed with water. The organic layer was dried over $MgSO_4$, filtered, and concentrated in vacuo. Purification of the crude material by flash chromatography ($SiO_2$, 20-50% EtOAc/hexanes) afforded the product (0.91 g, 2.6 mmol, 84%) as a brown oil.

e) A heavy-walled glass flask containing the carbobenzyloxy-protected amine (0.91 g, 2.6 mmol) from step d, concentrated hydrochloric acid (5 drops), and 10% Pd/C (90 mg, 10 wt %) in MeOH (2 mL) and EtOAc (20 mL) was fitted onto a Parr apparatus and agitated under $H_2$ at 45 psi. After 3 h, the reaction mixture was filtered through a pad of Celite and the filtrate was concentrated in vacuo. The crude material was diluted with EtOAc (40 mL) and washed with saturated aqueous $NaHCO_3$ (1×30 mL) to afford the product as dark oil (0.34 g, 1.5 mmol, 60%).

f) The product from step e was used in a procedure analogous to Example 2, substituting 1-(4-fluorophenyl)-5- methylpyrazol-4-amine for 1-(4-fluorophenyl)-5-propylpyrazol-4-amine in step 2a to afford the titled compound. $^1$H NMR (400 MHz, CDCl$_3$) δ 7.61 (s, 1H), 7.39 (dd, J=8.9, 4.8 Hz, 2H), 7.18 (dd, J=8.5, 8.5 Hz, 2H), 5.05 (dd, J=9.2, 5.9 Hz, 1H), 4.04 (dddd, J=9.2, 8.8, 4.8 Hz, 1.2, 1H), 3.89 (ddd, J=9.6, 8.0, 5.2 Hz, 1H), 2.90 (dddd, J=11.6, 8.8, 6.0, 6.0 Hz, 1H), 2.76 (dddd, J=13.6, 9.6, 8.4, 5.2 Hz, 1H), 2.66-2.51 (m, 2H), 2.42 (s, 3H), 1.35 (dddd, J=14.8, 8.8, 6.8, 6.8 Hz, 2H), 0.75 (t, J=7.4 Hz, 3H); MS: (ES) m/z calculated for C$_{21}$H$_{20}$ClF$_4$N$_5$O [M+H]$^+$470.1, found 470.1.

Example 18

Synthesis of 3-[4-chloro-5-methyl-3-(trifluoromethyl)pyrazol-1-yl]oxepan-2-one

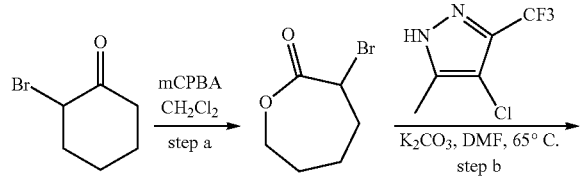

Example 19

Synthesis of 3-[4-chloro-5-methyl-3-(trifluoromethyl)pyrazol-1-yl]-1-[1-(4-fluorophenyl)-5-methylpyrazol-4-yl]azepan-2-one

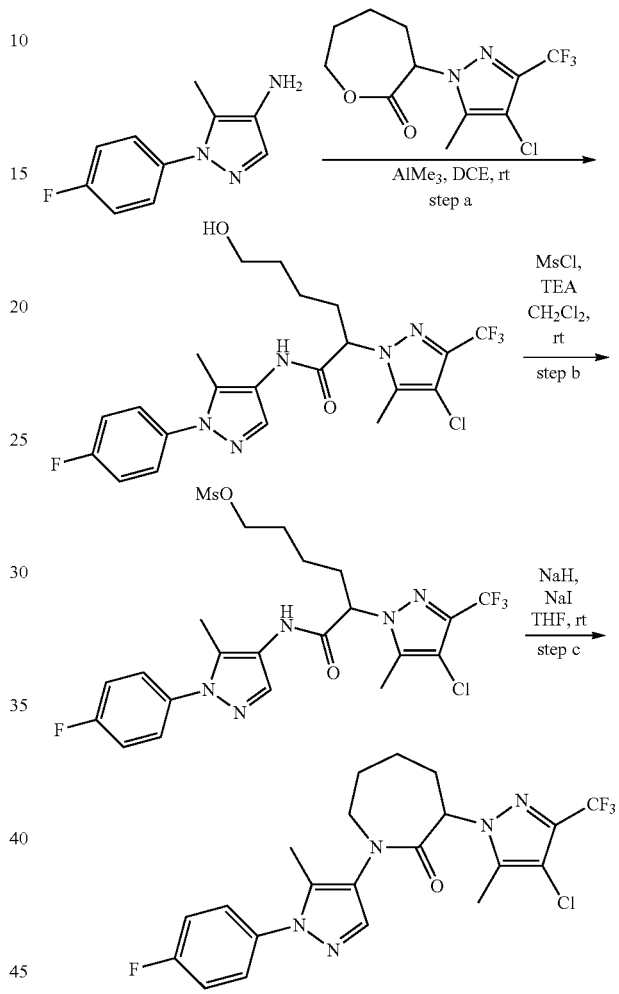

a) To a solution of 2-bromocyclohexanone (4 g, 22.6 mmol) in dichloromethane (38 mL) was added m-CPBA (5.10 g, 29.5 mmol). After stirring at room temperature for 14 h, the reaction was cooled in a freezer for 6 h. The solid was filtered off and rinsed with dichloromethane (15 mL) twice. The filtrate was then quenched with aqueous saturated sodium thiosulfate (40 mL). The organic layers were washed with water and brine, dried (Na$_2$SO$_4$), filtered, and concentrated in vacuo. Purification by flash chromatography (SiO$_2$, 20% EtOAc/hexanes) gave the product as a white solid (3 g, 15.5 mmol, 69%).

b) To a solution of 3-bromooxepan-2-one (1 g, 5.18 mmol) in DMF (10 mL) was added 4-chloro-5-methyl-3-(trifluoromethyl)-1H-pyrazole (0.956 g, 5.18 mmol), followed by potassium carbonate (1.07 g, 7.74 mmol). The reaction mixture was then heated at 65° C. for 8 h. After cooling to room temperature, the reaction mixture was partitioned between water (20 mL) and ethyl acetate (30 mL). The organic layers were washed with water and brine, dried (Na$_2$SO$_4$), filtered, and concentrated in vacuo. Purification by flash chromatography (SiO$_2$, 25% EtOAc/hexanes) gave the title product as a white solid (0.3 g, 1.01 mmol, 20%).

a) To a solution of 3-[4-chloro-5-methyl-3-(trifluoromethyl)pyrazol-1-yl]oxepan-2-one (0.05 g, 0.168 mmol) in dichloroethane (1.0 mL) was added trimethylaluminum (126 μL, 2.0 M, 0.25 mmol) under nitrogen, followed by 1-(4-fluorophenyl)-5-methylpyrazol-4-amine (0.032 g, 0.168 mmol) in dichloroethane (0.7 mL). The reaction mixture was allowed to stir for 1 h before it was carefully quenched with 1 N HCl (2 mL). The aqueous layer was basified with saturated aqueous sodium bicarbonate (2 mL) and extracted with dichloromethane (2×5 mL). The combined organic layers were washed with brine, dried over Na$_2$SO$_4$, filtered, and concentrated in vacuo. The crude material was used directly in the following step.

b) Methane sulfonyl chloride (0.029 g, 0.25 mmol) was added to a solution of the crude residue from step a and triethylamine (0.034 g, 0.34 mmol) in dichloromethane (1 mL) at room temperature. After stirring at room temperature for 1 h, the reaction was quenched with water. The aqueous layer was extracted with ethyl acetate (2×5 mL). The combined organic layers were washed with brine, dried ($Na_2SO_4$), filtered, and concentrated in vacuo. The crude material was used directly in the following step.

c) To a solution of the crude residue from step b in tetrahydrofuran (1 mL) was added sodium hydride (0.01 g, 60%, 0.25 mmol), followed by sodium iodide (0.003 g, 0.02 mmol) at room temperature. The reaction mixture was heated to 60° C. and allowed to stir at that temperature for 30 min. After cooling to room temperature, the reaction mixture was quenched with water and the aqueous layer was extracted with ethyl acetate (2×25 mL) and the combined organic layers were washed with brine, dried ($Na_2SO_4$), filtered, and concentrated in vacuo. The resulting crude product was purified by reverse phase HPLC (C18 column, acetonitrile $H_2O$ with 0.1% TFA as eluent) to give the title compound as a white solid (0.011 g, 0.025 mmol, 15% for 3 steps). $^1$H NMR (400 MHz, $CDCl_3$) δ 7.55 (s, 1H), 7.49-7.39 (m, 2H), 7.22-7.13 (m, 2H), 4.5-4.40 (m, 1H), 4.16-4.01 (m, 1H), 3.68-3.51 (m, 2H), 2.92-2.84 (m, 1H), 2.45-2.38 (m, 1H), 2.35 (s, 3H), 2.26-2.18 (m, 1H), 2.20 (s, 3H), 1.98-1.85 (m, 1H), 0.95-0.77 (m, 1H); MS: (ES) m/z calculated for for $C_{21}H_{20}ClF_4N_5O$ [M+H]$^+$470.1, found 470.1.

Example 20

Synthesis of 3-[4-chloro-5-methyl-3-(trifluoromethyl)pyrazol-1-yl]-1-[1-(4-fluorophenyl)-5-methylpyrazol-4-yl]piperidin-2-one

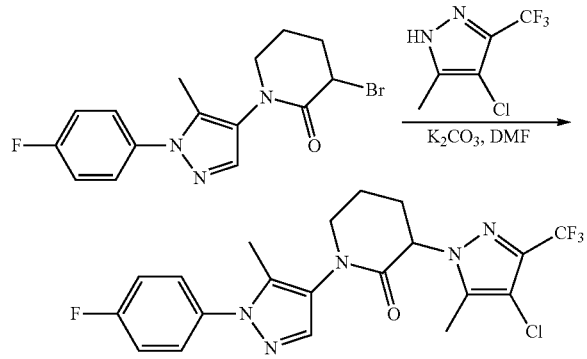

To a solution of 3-bromo-1-[1-(4-fluorophenyl)-5-methylpyrazol-4-yl]piperidin-2-one (0.05 g, 0.14 mmol) in DMF (1.0 mL) was added 4-chloro-5-methyl-3-(trifluoromethyl)-1H-pyrazole (0.031 g, 0.17 mmol), followed by potassium carbonate (0.029 g, 0.21 mmol). After stirring at room temperature for 1 h, the reaction was quenched with water. The aqueous layer was then extracted with ethyl acetate (2×25 mL). The combined organic layers were washed with brine, dried ($Na_2SO_4$), filtered, and concentrated in vacuo. The resulting crude product was purified by reverse phase HPLC (C18 column, acetonitrile $H_2O$ with 0.1% TFA as eluent) to give the title compound as a white solid (0.015 g, 0.025 mmol, 23%). $^1$H NMR (400 MHz, $CDCl_3$) δ 7.65 (s, 1H), 7.44-7.35 (m, 2H), 7.22-7.13 (m, 2H), 4.94 (dd, J=9.9, 6.3 Hz, 1H), 3.90-3.70 (m, 2H), 2.73 (dddd, J=13.2, 11.5, 9.8, 3.3 Hz, 1H), 2.47-2.38 (m, 1H), 2.36 (s, 3H), 2.31 (ddd, J=10.6, 5.4, 2.4 Hz, 1H), 2.17-2.12 (m, 1H), 2.13 (s, 3H); MS: (ES) m/z calculated for for $C_{20}H_{18}ClF_4N_5O$ [M+H]$^+$ 456.1, found 456.1.

Example 21

Synthesis of 3-[4-chloro-5-methyl-3-(trifluoromethyl)pyrazol-1-yl]-1-[1-(4-fluorophenyl)-5-phenylpyrazol-4-yl]pyrrolidin-2-one

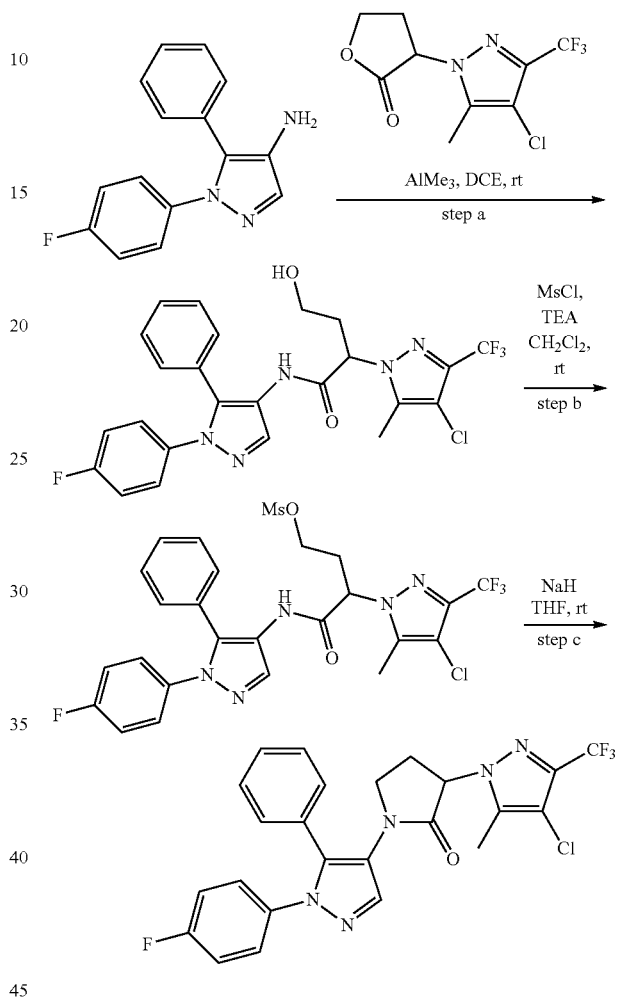

a) To a solution of 3-[4-chloro-5-methyl-3-(trifluoromethyl)pyrazol-1-yl]tetrahydrofuran-2-one (0.063 g, 0.236 mmol) in dichloroethane (1.0 mL) was added trimethylaluminum (177 μL, 2.0 M, 0.354 mmol) under nitrogen, followed by 1-(4-fluorophenyl)-5-phenyl-pyrazol-4-amine (0.06 g, 0.236 mmol) in dichloroethane (0.7 mL). The reaction mixture was allowed to stir for 1 h before it was carefully quenched with 1 N HCl (2 mL). The aqueous layer was then basified with saturated aqueous sodium bicarbonate (2 mL) and extracted with dichloromethane (5 mL×2). The combined organic layers was washed with brine, dried over $Na_2SO_4$, filtered, and concentrated in vacuo. The crude material was used directly in the following step.

b) Methanesulfonyl chloride (0.041 g, 0.36 mmol) was added to a solution of the crude residue from step a and triethylamine (0.049 g, 0.49 mmol) in dichloromethane (1 mL) at room temperature. After stirring at room temperature for 1 h, the reaction was quenched with water. The aqueous layer was extracted with ethyl acetate (2×5 mL). The combined organic layers were washed with brine, dried ($Na_2SO_4$), filtered, and concentrated in vacuo. The crude material was used directly in the following step.

c) Sodium hydride (0.014 g, 60%, 0.35 mmol) was added to a solution of the crude residue from step b in tetrahydrofuran (1 mL) at room temperature. The reaction mixture was heated to 60° C. and allowed to stir at that temperature for 30 min. After cooling to room temperature, the reaction mixture was quenched with water and the aqueous layer was extracted with ethyl acetate (2×5 mL) and the combined organic layers were washed with brine, dried (Na$_2$SO$_4$), filtered, and concentrated in vacuo. The resulting crude product was purified by reverse phase HPLC (C18 column, acetonitrile-H$_2$O with 0.1% TFA as eluent) to give the title compound as a white solid (0.025 g, 0.050 mmol, 21% for 3 steps). $^1$H NMR (400 MHz, CDCl$_3$) δ 7.89 (d, J=0.6 Hz, 1H), 7.42-7.28 (m, 3H), 7.25-7.14 (m, 4H), 7.04-6.94 (m, 2H), 4.99 (dd, J=9.2, 6.8 Hz, 1H), 3.74-3.63 (m, 1H), 3.56-3.45 (m, 1H), 2.78 (ddt, J=13.2, 8.7, 6.6 Hz, 1H), 2.55 (tq, J=13.4, 4.5 Hz, 1H), 2.38 (d, J=0.7 Hz, 3H); MS: (ES) m/z calculated for for C$_{24}$H$_{18}$ClF$_4$N$_5$O [M+H]$^+$504.1, found 503.9.

Example 22

1-[1-(4-Chlorophenyl)-5-isopropylpyrazol-4-yl]-3-methyl-3-[2-methyl-4-(trifluoromethyl)imidazol-1-yl]pyrrolidin-2-one

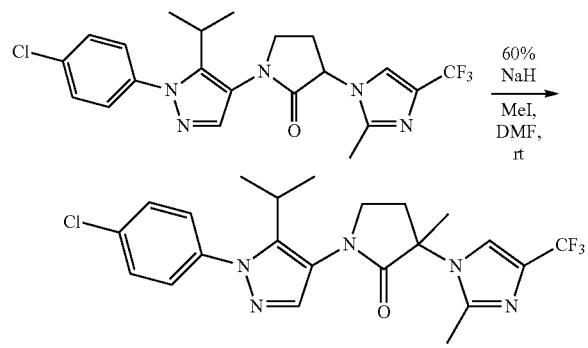

To a solution of 1-[1-(4-chlorophenyl)-5-isopropylpyrazol-4-yl]-3-[2-methyl-4-(trifluoromethyl)imidazol-1-yl]pyrrolidin-2-one (50 mg, 0.11 mmol) was added DMF (2 mL) and NaH (60% in mineral oil, 16 mg, 0.33 mmol) slowly at room temperature under nitrogen atmosphere. After stirring for 10 min at room temperature, MeI (34 µL, 0.55 mmol) was added and further stirred for 2 h. Saturated NH$_4$Cl solution (10 mL) was then added at 0° C. slowly to the reaction mixture followed by extraction with EtOAc (2×25 mL). The combined EtOAc layers were dried (MgSO$_4$), concentrated in vacuo, and purified by reverse phase HPLC (C18 column, acetonitrile-H$_2$O with 0.1% TFA as eluent) to give 1-[1-(4-chlorophenyl)-5-isopropyl-pyrazol-4-yl]-3-methyl-3-[2-methyl-4-(trifluoromethyl)imidazol-1-yl]pyrrolidin-2-one (17 mg, 0.029 mmol, 27% yield) as a TFA salt. $^1$H NMR (400 MHz, Methanol-d$_4$) δ 7.88 (s, 1H), 7.70 (s, 1H), 7.59 (d, J=11.76 Hz, 2H), 7.42 (d, J=11.76 Hz, 2H), 3.86-3.95 (m, 2H), 2.99-3.08 (m, 1H), 2.58-2.80 (m, 2H), 2.52 (s, 3H), 1.96 (s, 3H), 1.22 (d, J=23.4 Hz, 3H), 1.20 (d, J=23.4 Hz, 3H); MS: (ES) m/z calculated for C$_{22}$H$_{23}$ClF$_3$N$_5$O [M+H]$^+$466.9, found 466.1.

Example 23

Synthesis of 3-[4-chloro-5-methyl-3-(trifluoromethyl)-1H-pyrazol-1-yl]-1-[1-(3-fluorophenyl)-5-(furan-3-yl)-1H-pyrazol-4-yl]pyrrolidin-2-one

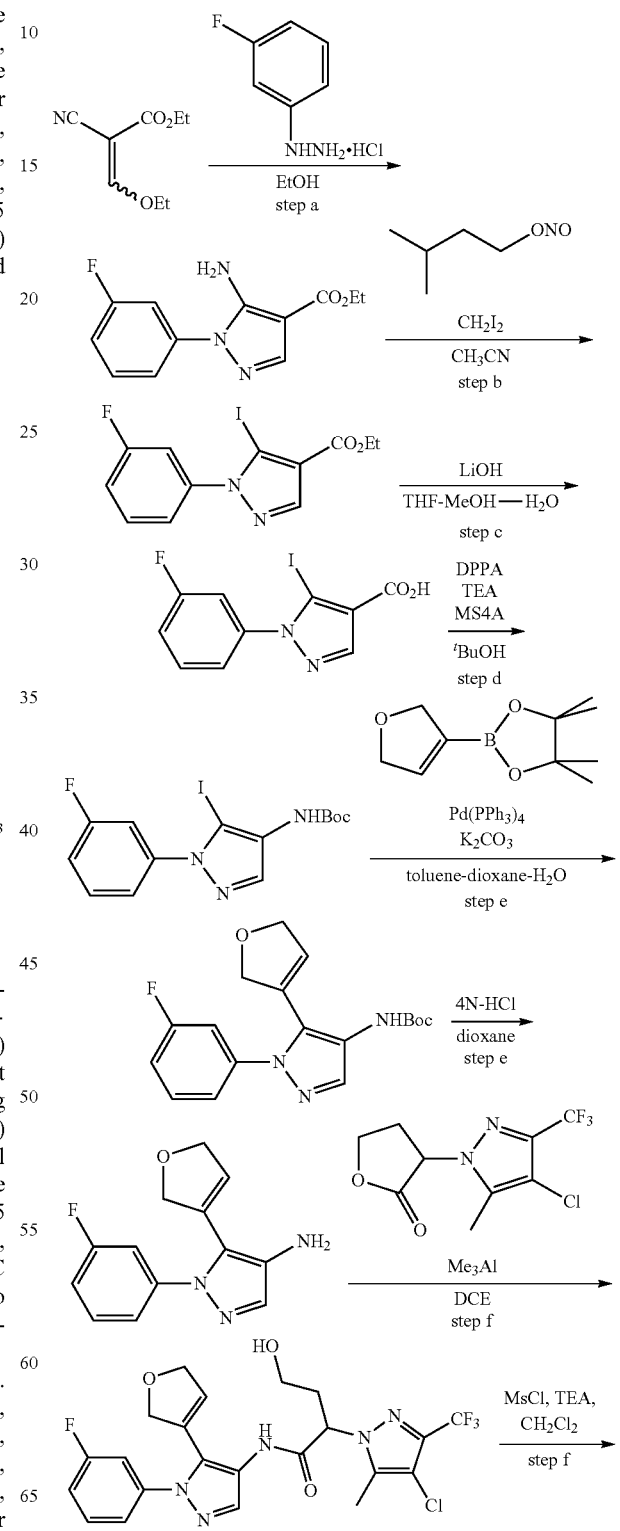

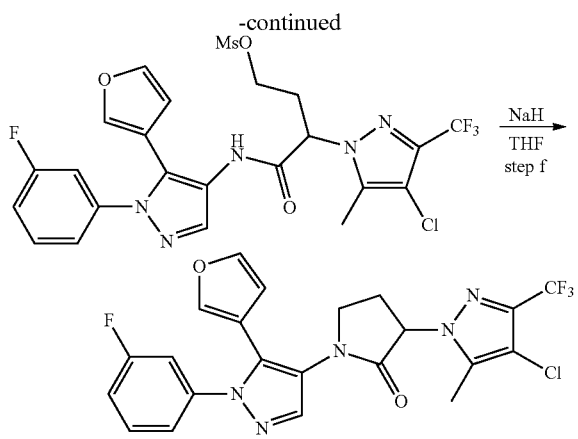

a) Ethyl (ethoxyethylene)cyanoacetate (2.37 g, 14.0 mmol) and 3-fluorophenylhydrazine hydrochloride (2.28 g, 14.0 mmol) were suspended in ethanol (50 mL). The reaction mixture was heated at 80° C. for three days, followed by the removal of EtOH under reduced pressure. The crude reaction mixture was suspended in dichloromethane and the insoluble materials were removed via filtration. The filtrate was concentrated under reduced pressure and purified via silica gel column chromatography (5-20% ethyl acetate in hexanes) to afford ethyl 5-amino-1-(3-fluorophenyl)-1H-pyrazole-4-carboxylate (930 mg, 3.73 mmol, 27% yield).

b) Ethyl 5-amino-1-(3-fluorophenyl)-1H-pyrazole-4-carboxylate (518 mg, 2.08 mmol) was suspended in acetonitrile (5 mL) at ambient temperature. Diiodomethane (675 μL, 8.38 mmol) was added followed by isopentyl nitrite (565 μL, 4.21 mmol). The reaction was heated at 50° C. for one hour and was then partitioned between water and ethyl acetate. The aqueous layer was extracted twice more with ethyl acetate. The combined organic layers were dried over anhydrous sodium sulfate. After removal of solvents under reduced pressure, the crude material was purified using silica gel column chromatography (10-25% ethyl acetate in hexanes) to afford ethyl 5-iodo-1-(3-fluorophenyl)-1H-pyrazole-4-carboxylate (589 mg, 1.64 mmol, 79% yield).

c) Ethyl 5-iodo-1-(3-fluorophenyl)-1H-pyrazole-4-carboxylate (589 mg, 1.64 mmol) was dissolved in a mixture of tetrahydrofuran (5 mL), 1.5 N LiOH (1.6 mL) and methanol (1.5 mL) and the mixture was stirred overnight. Most of the tetrahydrofuran was removed by gently blowing a stream of nitrogen over the reaction mixture. Water and 1 N HCl (2.4 mL) was added and the mixture was sonicated well to precipitate the carboxylic acid. The carboxylic acid was filtered and rinsed with water. After drying under vacuum, 5-iodo-1-(3-fluorophenyl)-1H-pyrazole-4-carboxylic acid was obtained (488 mg, 1.47 mmol, 90% yield). This material was used for the next step without further purification.

d) Tert-butyl alcohol (3.5 mL) was first dried by stirring overnight at 50° C. in the presence of 4A molecular sieves. To this solvent was added 5-iodo-1-(3-fluorophenyl)-1H-pyrazole-4-carboxylic acid (488 mg, 1.47 mmol), followed by triethylamine (204 μL, 1.46 mmol) and diphenylphosphoryl azide (334 μL, 1.54 mmol) at ambient temperature. The reaction mixture was heated to 60° C. and stirred overnight. The reaction was then diluted with ethyl acetate. Silica gel was added to the reaction mixture and the solvents were removed under reduced pressure to preabsorb the crude materials onto silica gel. The material was then purified using silica gel column chromatography (6-20% ethyl acetate in hexanes) to afford 5-iodo-1-(3-fluorophenyl)-1H-pyrazol-4-yl-carbamic acid 1,1-dimethylethyl ester (482 mg, 1.20 mmol, 81% yield).

e) To a vial containing 5-iodo-1-(3-fluorophenyl)-1H-pyrazol-4-yl-carbamic acid 1,1-dimethylethyl ester (150 mg, 0.372 mmol), was added 2-(2,5-dihydro-3-furanyl)-4,4,5,5-tetramethyl-1,3,2-dioxaborolane (100 mg, 0.512 mmol) in toluene (2.5 mL). Dioxane (0.56 mL) was added followed by aqueous potassium carbonate (2 M, 560 μL, 1.12 mmol). Nitrogen was flushed through the vial, followed by addition of tetrakistriphenylphosphine palladium (20.1 mg, 0.0174 mmol). The reaction was stirred at 100° C. overnight. After cooling to room temperature, the reaction was diluted with ethyl acetate and water. The layers were separated and the aqueous layer was extracted twice more with ethyl acetate. The combined organic layers were dried over anhydrous sodium sulfate. After removal of the solvent under reduced pressure, the crude material was purified using silica gel column chromatography (5-33% ethyl acetate in hexanes) to afford the Suzuki reaction product (55.4 mg, 0.160 mmol, 43% yield). This material was treated with hydrochloric acid in dioxane (4 N, 1 mL) at ambient temperature for two hours. After removal of excess hydrochloric acid and dioxane under reduced pressure, the crude material was dissolved in ethyl acetate and washed with saturated sodium bicarbonate solution. The aqueous layer was extracted twice more with ethyl acetate. The combined organic layers were dried over anhydrous sodium sulfate. The solvent was removed under reduced pressure to obtain the crude product whose major component was 5-(3-furanyl)-1-(3-fluorophenyl)-4-amino-1H-pyrazole (48.4 mg).

f) The crude material from the previous step (48.4 mg) and 3-(3-trifluoromethyl-4-chloro-5-methyl-1H-pyrazol-1-yl)dihydro-2(3H)-furanone (47 mg, 0.18 mmol) was dissolved in dichloroethane (0.5 mL). To this mixture was added trimethylaluminum (2 M in toluene, 0.12 mL, 0.24 mmol) at room temperature. The reaction was stirred at room temperature for two hours. Hydrochloric acid (1 N) and dichloromethane were added and the layers were separated. The aqueous layer was extracted with dichloromethane twice more. The combined organic layers were dried over anhydrous sodium sulfate. The solvent was removed under reduced pressure to afford the crude product (62.0 mg) which was dissolved in dichloromethane (1 mL). At ambient temperature, triethylamine (84 μL, 0.60 mmol) was added followed by dropwise addition of methanesulfonyl chloride (19 μL, 0.24 mmol). The reaction was stirred at the same temperature for thirty minutes. Saturated sodium bicarbonate solution was added and the product was extracted with dichloromethane three times. The combined organic layers were dried over anhydrous sodium sulfate. After removal of the solvent under reduced pressure, the crude product was dissolved in tetrahydrofuran (1 mL) at ambient temperature. Sodium hydride (60% dispersion in oil) was added in small portions until no more bubbling was observed. The reaction was stirred at this temperature overnight. Water and ethyl acetate were added to the reaction mixture and the layers were separated. The aqueous layer was extracted with ethyl acetate twice more. The combined organic layers were dried over anhydrous sodium sulfate. This solution was passed through a pad of silica gel and rinsed well with ethyl acetate to remove the baseline impurities. This material was then concentrated under reduced pressure and further purified using reverse phase HPLC (C18 column, 20-95% acetonitrile in water with 0.1% trifluoroacetic acid) to afford 3-[4-chloro-5-methyl-3-(trifluoromethyl)-1H-pyrazol-1-yl]-1-[1-(3-fluorophenyl)-5-(furan-3-yl)-1H-pyrazol-4-yl]pyrrolidin-2-one (2.7 mg, 0.0055 mmol, 3% yield over 4 steps). $^1$H NMR (400 MHz, CDCl$_3$) δ 7.80 (s, 1H), 7.31-7.47 (m, 3H), 7.33 (dd, J=8.0, 6.4 Hz, 1H), 7.14 (d, J=7.2 Hz, 1H), 7.04-7.10 (m, 1H), 6.45 (s, 1H), 5.03 (dd, J=9.6, 6.8 Hz, 1H), 3.88 (ddd, J=9.4, 9.4, 5.1 Hz, 1H), 3.67 (ddd, J=10.0, 8.4, 6.4 Hz, 1H), 2.78-2.87 (m, 1H), 2.66 (dddd, J=17.2, 8.2, 4.3, 4.3 Hz, 1H), 2.40 (s, 3H); MS: (ES) m/z calculated for C$_{22}$H$_{16}$N$_5$O$_2$ClF$_4$ [M+H]$^+$494.1, found 494.0.

Example 24

Synthesis of 3-[4-chloro-5-methyl-3-(trifluoromethyl)-1H-pyrazol-1-yl]-1-[5-cyclopropyl-1-(3-fluorophenyl)-1H-pyrazol-4-yl]pyrrolidin-2-one

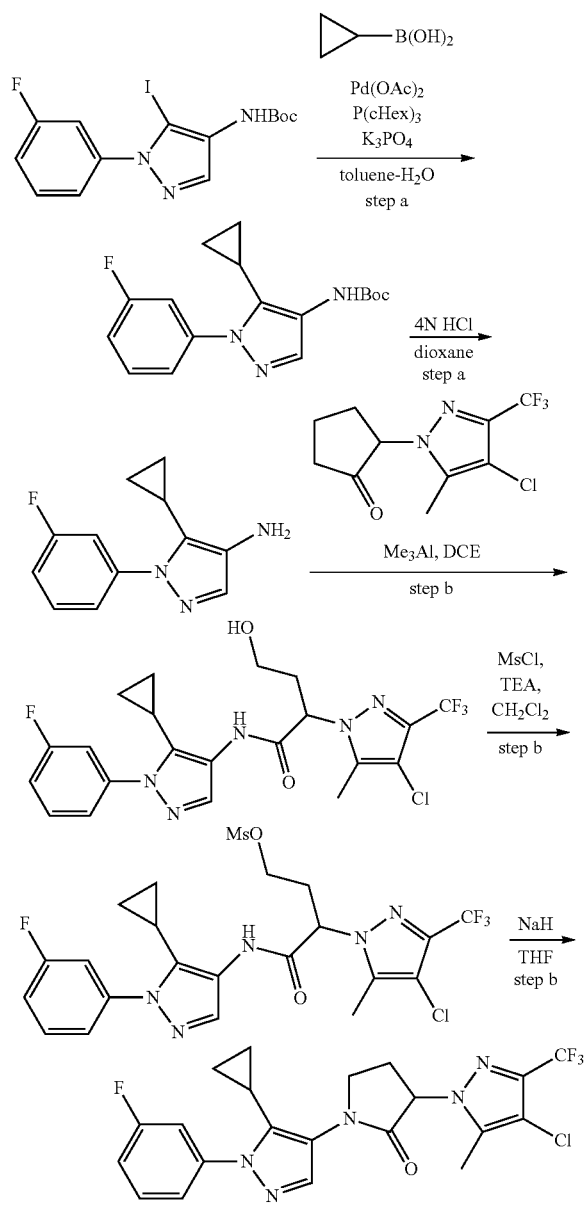

a) A reaction vial was charged with 5-iodo-1-(3-fluorophenyl)-1H-pyrazol-4-yl)-carbamic acid 1,1-dimethylethyl ester (150 mg, 0.372 mmol), cyclopropylboronic acid (43.0 mg, 0.504 mmol), tricyclohexylphosphine (10.0 mg, 0.0357 mmol), and potassium phosphate (276 mg, 1.30 mmol). Toluene (1.7 mL) and water (85 μL) were added. The reaction was flushed with nitrogen, followed by addition of palladium acetate (4.2 mg, 0.019 mmol). The reaction mixture was heated at 100° C. for two hours. More tricyclohexylphosphine (10.3 mg, 0.0367 mmol) and palladium acetate (4.5 mg, 0.020 mmol) were added and stirring was continued at 100° C. for five more hours. BrettPhos (2-(dicyclohexylphosphino)3,6-dimethoxy-2',4',6'-triisopropyl-1,1'-biphenyl, 10.7 mg, 0.0199 mmol) and palladium acetate (3.9 mg, 0.0174 mmol) were added and the reaction mixture was further stirred at 100° C. overnight. After cooling to room temperature, water and ethyl acetate were added and the layers were separated. The aqueous layer was extracted twice more with ethyl acetate and the combined organic layers were dried over anhydrous sodium sulfate. After removal of solvents under reduced pressure, the crude material was purified using silica gel column chromatography (7-80% ethyl acetate in hexanes) to give the Suzuki reaction product (41.4 mg, 0.130 mmol, 35% yield). To this product was added hydrochloric acid in dioxane (4 N, 1 mL) and the reaction was stirred at ambient temperature for four hours. After removal of solvent under reduced pressure, the reaction mixture was partitioned between ethyl acetate and saturated sodium bicarbonate solution. The layers were separated and the aqueous layer was extracted twice more with ethyl acetate. The combined organic layers were dried over anhydrous sodium sulfate. Removal of solvent under reduced pressure gave 5-(3-cyclopropyl)-1-(3-fluorophenyl)-4-amino-1H-pyrazole (25.6 mg, 0.118 mmol, 91% yield) which was used in the next step without further purification.

b) The product from the previous step (25.6 mg, 0.118 mmol) and 3-(3-trifluoromethyl-4-chloro-5-methyl-1H-pyrazol-1-yl)dihydro-2(3H)-furanone (49.0 mg, 0.182 mmol) was dissolved in dichloroethane (0.5 mL). To this mixture was added trimethylaluminum (2 M in toluene, 0.12 mL, 0.24 mmol) at room temperature. The reaction was stirred at room temperature for two hours. More trimethylaluminum (2 M in toluene, 0.7 mL, 1.4 mmol) was added and the reaction was further stirred at room temperature of another two hours. Hydrochloric acid (1 N) and dichloromethane were then added and the layers were separated. The aqueous layer was extracted with dichloromethane twice more. The combined organic layers were washed once with saturated sodium bicarbonate solution and dried over anhydrous sodium sulfate. The solvent was removed under reduced pressure to afford the crude product (73.2 mg) which was dissolved in dichloromethane (1 mL). At ambient temperature, methanesulfonyl chloride (23 μL, 0.30 mmol) and triethylamine (105 μL, 0.753 mmol) were added. The reaction was stirred at the same temperature for two hours. Saturated sodium bicarbonate solution was added and the product was extracted with dichloromethane three times. The combined organic layers were dried over anhydrous sodium sulfate. After removal of the solvent under reduced pressure, the crude product was dissolved in tetrahydrofuran (1 mL) at ambient temperature. Sodium hydride (60% dispersion in oil) was added in small portions until no more bubbling was observed. The reaction was stirred at this temperature for one hour. Saturated ammonium chloride solution and ethyl acetate were added to the reaction mixture and the layers were separated. The aqueous layer was then extracted with ethyl acetate twice more. The combined organic layers were dried over anhydrous sodium sulfate. After removal of solvent under reduced pressure, the crude product was treated with 2-methyl-4-trifluoromethyl-1H-imidazole (16.7 mg, 0.111 mmol) and potassium carbonate (90.2 mg, 0.653 mmol) in dimethylformamide (0.5 mL) at 55° C. for three hours. Ethyl acetate and water were then added to the reaction mixture. The layers were separated and the aqueous layer was extracted twice more with ethyl acetate. The combined organic layers were dried over anhydrous sodium sulfate. After removal of solvents under reduced pressure, the crude material was purified using silica gel column chromatography (50-60% ethyl acetate in hexanes) to afford 3-[4-chloro-5-methyl-3-(trifluoromethyl)-1H-pyrazol-1-yl]-1-[1-(3-fluorophenyl)-5-(cycloprop-3-yl)-1H-pyrazol-4-yl]pyrrolidin-2-one, which was further purified using reverse phase HPLC (C18 column, 20-95% acetonitrile in water with 0.1% trifluoroacetic acid) (15.0 mg, 0.0346 mmol, 29% yield over three steps). $^1$H NMR (400 MHz, CDCl$_3$) δ 7.61 (s, 1H), 7.37-7.44 (m, 2H), 7.33 (ddd, J=9.6, 2.0, 2.0 Hz, 1H), 7.04-7.09 (m, 1H), 5.04 (dd, J=9.6, 6.8 Hz, 1H), 4.10 (ddd, J=9.6, 9.6, 4.8 Hz, 1H), 3.89 (ddd, J=9.0, 8.0, 5.6 Hz, 1H), 2.97 (dddd, J=14.8, 8.4, 8.4, 5.6 Hz, 1H), 2.73 (dddd, J=17.2, 8.4, 5.2, 5.2 Hz, 1H), 2.42 (s, 3H), 1.79 (tt, J=10.4, 5.6 Hz, 1H), 0.71-0.82 (m, 2H), 0.36-0.40 (m, 2H); MS: (ES) m/z calculated for C$_{21}$H$_{18}$N$_5$OClF$_4$ [M+H]$^+$468.2, found 468.1.

Example 25

Synthesis of 3-[4-chloro-5-methyl-3-(trifluoromethyl)-1H-pyrazol-1-yl]-1-[1-(3-fluorophenyl)-5-iodo-1H-pyrazol-4-yl]pyrrolidin-2-one

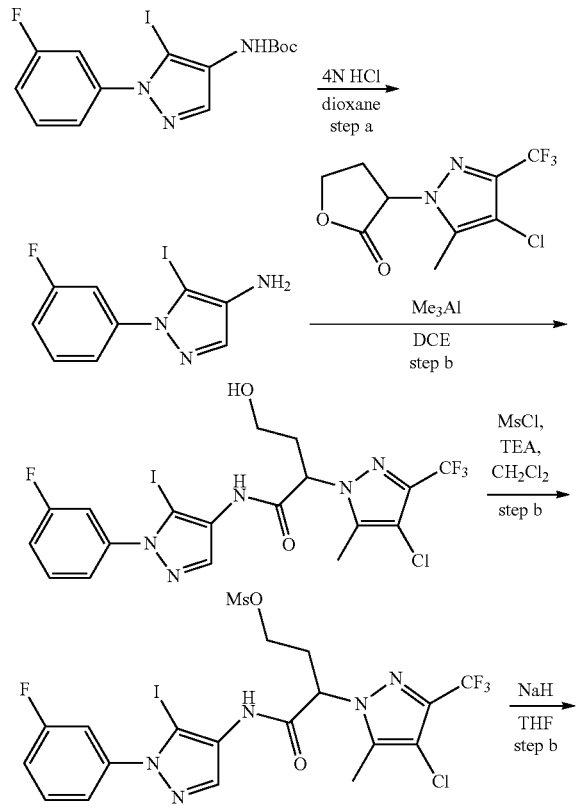

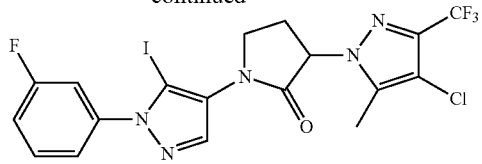

a) Hydrochloric acid in dioxane (4 N, 3 mL) was added to 5-iodo-1-(3-fluorophenyl)-1H-pyrazol-4-yl-carbamic acid 1,1-dimethylethyl ester (348 mg, 0.864 mmol) at ambient temperature. The reaction was stirred overnight at the same temperature. Solvent was removed under reduced pressure. The crude material was dissolved in ethyl acetate and saturated sodium bicarbonate solution. The layers were separated and the aqueous layer was extracted twice more with ethyl acetate. The combined organic layers were dried over anhydrous sodium sulfate. After removal of the solvent under reduced pressure, the crude material was purified using silica gel column chromatography (20-60% ethyl acetate in hexanes) to afford 5-iodo-1-(3-fluorophenyl)-1H-pyrazol (210 mg, 0.695 mmol, 80% yield).

b) The free amine from the previous step (211 mg, 0.695 mmol) and 3-(3-trifluoromethyl-4-chloro-5-methyl-1H-pyrazol-1-yl)dihydro-2(3H)-furanone (229 mg, 0.853 mmol) was dissolved in dichloroethane (2.3 mL). To this mixture was added trimethylaluminum (2 M in toluene, 0.7 mL, 1.4 mmol) at room temperature. The reaction was stirred at room temperature for two hours. More trimethylaluminum (2 M in toluene, 0.3 mL, 0.6 mmol) was added and the reaction was further stirred at room temperature for another two hours. Hydrochloric acid (1 N) and dichloromethane were added and the mixture was passed through a pad of celite. The layers were separated, and the aqueous layer was extracted with dichloromethane twice more. The combined organic layers were dried over anhydrous sodium sulfate. The solvent was removed under reduced pressure to afford the crude product which was dissolved in dichloromethane (2 mL). At ambient temperature, methanesulfonyl chloride (81 μL, 1.04 mmol) and triethylamine (483 μL, 3.47 mmol) were added. The reaction was stirred at the same temperature for thirty minutes. Saturated sodium bicarbonate solution was added and the product was extracted with dichloromethane three times. The combined organic layers were dried over anhydrous sodium sulfate. After removal of solvent under reduced pressure, the crude product was dissolved in tetrahydrofuran (7.5 mL) at ambient temperature. Sodium hydride (60% dispersion in oil) was added in small portions until no more bubbling was observed (approximately 54 mg, 1.4 mmol). The reaction was stirred at this temperature for one hour. Saturated ammonium chloride solution and ethyl acetate were added to the reaction mixture and the layers were separated. The aqueous layer was extracted with ethyl acetate twice more. The combined organic layers were dried over anhydrous sodium sulfate. After removal of the solvent under reduced pressure, the crude material was purified using silica gel column chromatography (20-40% ethyl acetate in hexanes) to afford 3-[4-chloro-5-methyl-3-(trifluoromethyl)-1H-pyrazol-1-yl]-1-[1-(3-fluorophenyl)-5-iodo-1H-pyrazol-4-yl]pyrrolidin-2-one (126 mg, 0.227 mmol, 33% yield over three steps). This material was triturated from methanol for further purification (yield 42.5 mg). $^1$H NMR (400 MHz, CDCl$_3$) δ 7.80 (s, 1H), 7.45 (ddd, J=8.2, 8.2, 5.9 Hz, 1H), 7.34 (dd, J=8.2, 2.0 Hz, 1H), 7.28 (ddd, J=9.4, 2.0, 2.0 Hz, 1H), 7.16 (ddd, J=8.2, 8.2, 2.4 Hz, 1H), 5.06 (dd, J=9.6, 6.8 Hz, 1H), 4.08 (ddd, J=9.6, 9.6, 4.8 Hz, 1H), 3.94 (ddd, J=9.6, 8.0, 6.4 Hz, 1H), 3.00 (dddd, J=15.6, 8.4, 8.4, 6.4 Hz, 1H), 2.73 (dddd, J=17.2, 8.0, 4.8, 4.8 Hz, 1H), 2.42 (s, 3H); MS: (ES) m/z calculated for $C_{18}H_{13}N_5OClF_4I$ [M+H]$^+$554.0, found 554.0.

Example 26

Synthesis of 3-[4-chloro-5-methyl-3-(trifluoromethyl)-1H-pyrazol-1-yl]-1-[5-propyl-1-(3-fluorophenyl)-1H-pyrazol-4-yl]pyrrolidin-2-one

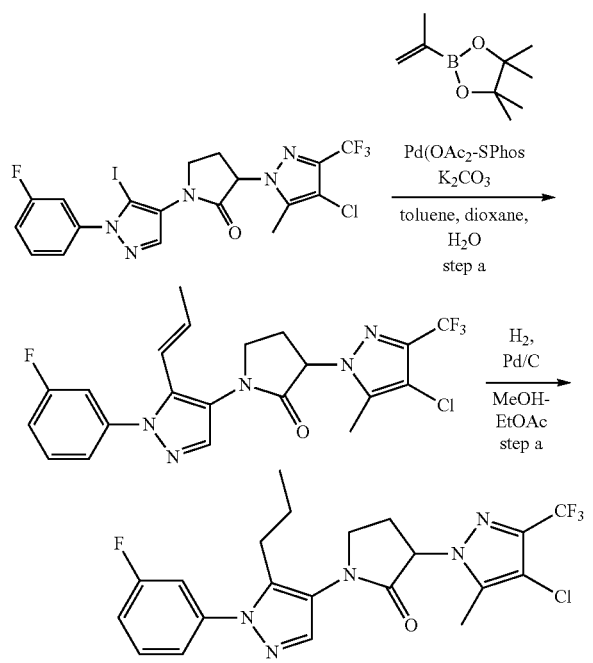

a) Potassium carbonate (43.1 mg, 0.312 mmol) was added to a flask containing 3-[4-chloro-5-methyl-3-(trifluoromethyl-1H-pyrazol-1-yl]-1-[1-(3-fluorophenyl)-5-iodo-1H-pyrazol-4-yl]pyrrolidin-2-one (83.0 mg, 0.150 mmol) followed by toluene (0.5 mL) and dioxane (0.1 mL). To this mixture was added 4,4,5,5-tetramethyl-2-(1-methylethenyl)-1,3-2-dioxaborolane (56 µL, 0.30 mmol) followed by water (25 µL), 2-dicyclohexylphophino-2',6'-dimethoxybiphenyl (SPhos, 6.2 mg, 0.015 mmol) and palladium acetate (3.3 mg, 0.015 mmol). The reaction mixture was flushed with nitrogen and stirred at 100° C. overnight. After cooling, water and ethyl acetate were added. The layers were separated and the aqueous layer was extracted twice more with ethyl acetate. The combined organic layers were dried over anhydrous sodium sulfate. After removal of the solvent under reduced pressure, the crude material was purified using silica gel column chromatography (30-100% ethyl acetate in hexanes) to afford the Suzuki product (24.4 mg, 0.0522 mmol, 35% yield). Some starting iodo compound was recovered as well as some des-iodo byproduct. The Suzuki product was dissolved in a mixture of ethyl acetate (5 mL) and methanol (5 mL). Palladium on carbon (10%, wet, 9.7 mg) was added. The mixture was hydrogenated using a Parr Apparatus at 35 psi hydrogen for one hour and then at 45 psi hydrogen for one hour. After purging the reaction mixture with nitrogen, more palladium on carbon (10%, wet, 10.3 mg) and solvents (ethyl acetate:methanol=1:1, 8 mL) were added and the reaction mixture was further hydrogenated at 45 psi for one hour. The reaction mixture was filtered through a pad of celite and thoroughly rinsed with ethyl acetate: methanol (1:1, 10 mL) mixture. After removal of the solvent under reduced pressure, the crude material was purified using a reverse phase HPLC (C18 column, 20-95% acetonitrile in water with 0.1% trifluoroacetic acid) to afford 3-[4-chloro-5-methyl-3-(trifluoromethyl)-1H-pyrazol-1-yl]-1-[5-propyl-1-(3-fluorophenyl)-1H-pyrazol-4-yl]pyrrolidin-2-one (14.4 mg, 0.0306 mmol, 59% yield). $^1$H NMR (400 MHz, CDCl$_3$) δ 7.60 (s, 1H), 7.43 (ddd, J=8.0, 8.0, 6.0 Hz, 1H), 7.14-7.22 (m, 3H), 5.02 (dd, J=9.2, 5.6 Hz, 1H), 4.02 (ddd, J=9.2, 5.2, 5.2 Hz, 1H), 3.86 (ddd, J=9.6, 8.0, 5.6 Hz, 1H), 2.88 (dddd, J=14.4, 8.8, 8.8, 6.0 Hz, 1H), 2.73 (dddd, J=17.2, 8.4, 5.6, 5.6 Hz, 1H), 2.57-2.68 (m, 2H), 2.41 (s, 3H), 1.35 (qt, J=9.6, 9.6 Hz, 2H), 0.74 (t, J=7.6 Hz, 3H); MS: (ES) m/z calculated for $C_{21}H_{20}N_5OClF_4$ [M+H]$^+$470.1, found 470.1.

Example 27

Synthesis of 3-(4-chloro-5-methyl-3-(trifluoromethyl)-1H-pyrazol-1-yl)-1-(1-(4-fluorophenyl)-5-isopropyl-1H-pyrazol-4-yl)-5-methylpyrrolidin-2-one

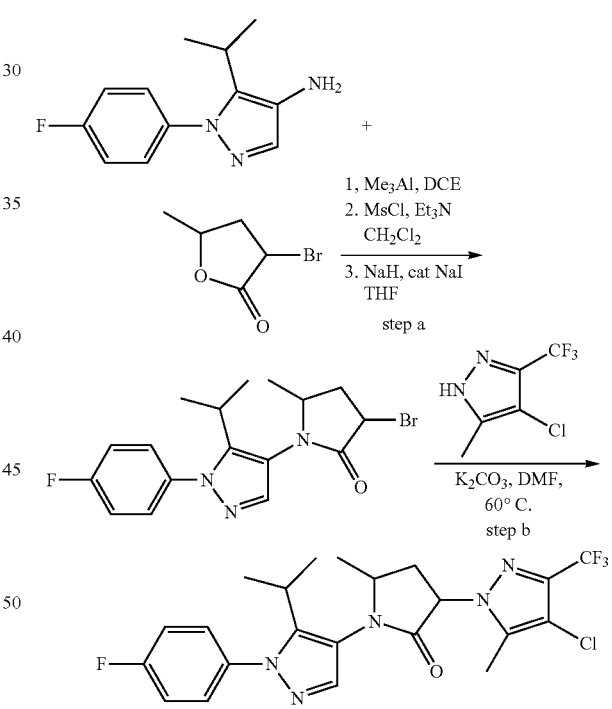

a) Trimethylaluminum (1.0 mL, 2 mmol, 2 M solution in toluene) was added portionwise to a solution of 1-(4-fluorophenyl)-5-isopropyl-1H-pyrazol-4-amine (219 mg, 1 mmol) and cis/trans-α-bromo-γ-valerolactone (358 mg, 2 mmol) in anhydrous dichloroethane (5 mL) under nitrogen at room temperature. After stirring for 2 h, the reaction was quenched with water and the mixture diluted with 10 mL of EtOAc and 0.5 mL of 6 N HCl. The organic layer was washed with water and brine, dried over MgSO$_4$, filtered, and concentrated in vacuo. The residue was dissolved in CH$_2$Cl$_2$ (6 mL) and Et$_3$N (0.25 mL, 1.8 mmol) and methanesulfonyl chloride (0.13 mL, 1.65 mmol) were added.

After stirring for 1 h, the reaction mixture was washed with 1 M NaHSO₄ and the organic layer was dried over MgSO₄, filtered, and concentrated in vacuo to give a yellow oil. The residue was dissolved in THF (10 mL) and NaI (30-40 mg) was added. Sodium hydride (90 mg, 2.3 mmol) was then added to the reaction slurry. After stirring for 16 h, the reaction was quenched with saturated NH₄Cl and concentrated under reduced pressure to remove THF. The mixture was diluted with water (10 mL) and extracted with EtOAc (3×5 mL). The organic layer was dried over MgSO₄, filtered, concentrated, and purified by flash chromatography (SiO₂, 5-90% EtOAc/hexanes) to give the product (219 mg, 0.38 mmol, 38%) as colorless oil.

b) To a solution of the product from step a (57 mg, 0.15 mmol) and 4-chloro-5-methyl-3-(trifluoromethyl)-1H-pyrazole (138 mg, 0.75 mmol) in DMF (1 mL) was added K₂CO₃ (104 mg, 0.75 mmol). The slurry was heated to 60° C. for 1 h and was then diluted with EtOAc (4 mL). The mixture was washed with water and brine and concentrated in vacuo. The crude residue was purified by reverse phase HPLC (C18 column, acetonitrile-H₂O with 0.1% TFA as eluent) to afford a cis/trans mixture of the title compound (40 mg, 0.083 mmol) as a white solid. ¹H NMR of the cis/trans mixture (400 MHz, CDCl₃) δ 7.46 (s, 0.54H), 7.43 (s, 0.46H), 7.42-7.36 (m, 2H), 7.20-7.15 (m, 2H), 5.11 (m, 1H), 4.35-4.27 (m, 0.46H), 4.10-4.01 (m, 0.54H), 3.06-2.84 (m, 2H), 2.68-2.60 (m, 0.46H), 2.43 (s, 1.38H), 2.40 (s, 1.62H), 2.34-2.25 (m, 0.54H), 1.40 (d, J=6.3 Hz, 1.62H), 1.37 (d, J=6.6 Hz, 1.38H), 1.17 (d, J=7.1 Hz, 1.38H), 1.16 (d, J=7.0 Hz, 1.62H), 1.12 (d, J=7.1 Hz, 1.62H), 1.04 (d, J=7.4 Hz, 1.38H); MS: (ES) m/z calculated for C₂₂H₂₃ClF₄N₆O [M+H]⁺484.1, found 483.9.

Example 28

Synthesis of 1-(1-(4-fluorophenyl)-5-isopropyl-1H-pyrazol-4-yl)-5-methyl-3-(2-methyl-4-(trifluoromethyl)-1H-imidazol-1-yl)pyrrolidin-2-one hydrochloride

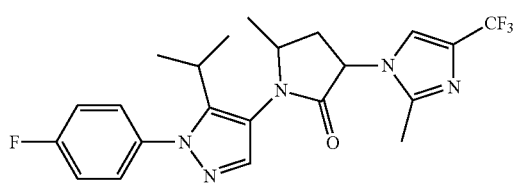 [SMILES: Cc1nc(C(F)(F)F)cn1C1CC(C)N(c2cnn(-c3ccc(F)cc3)c2C(C)C)C1=O]

The titled compound was prepared using the procedure as described for Example 27, substituting 4-chloro-5-methyl-3-(trifluoromethyl)-1H-pyrazole for 2-methyl-4-(trifluoromethyl)-1H-imidazole in step b. ¹H NMR of cis/trans mixture (400 MHz, CD₃OD) δ 8.50 (s, 0.64H), 8.43 (s, 0.36H), 7.64 (s, 1H), 7.52-7.49 (m, 2H), 7.32 (t, J=8.2 Hz, 2H), 5.82-5.76 (m, 1H), 4.26-4.20 (m, 1H), 3.16-2.96 (m, 2H), 2.82-2.79 (m, 1H), 2.48 (m, 1H), 2.29 (m, 1H), 1.37 (m, 2H), 1.19-1.15 (m, 6H); MS: (ES) m/z calculated for C₂₂H₂₃F₄N₅O [M+H]⁺450.2, found 450.0.

Example 29

Synthesis of 1-[1-(4-fluorophenyl)-5-isopropoxy-pyrazol-4-yl]-3-[2-methyl-4-(trifluoromethyl)imidazol-1-yl]pyrrolidin-2-one

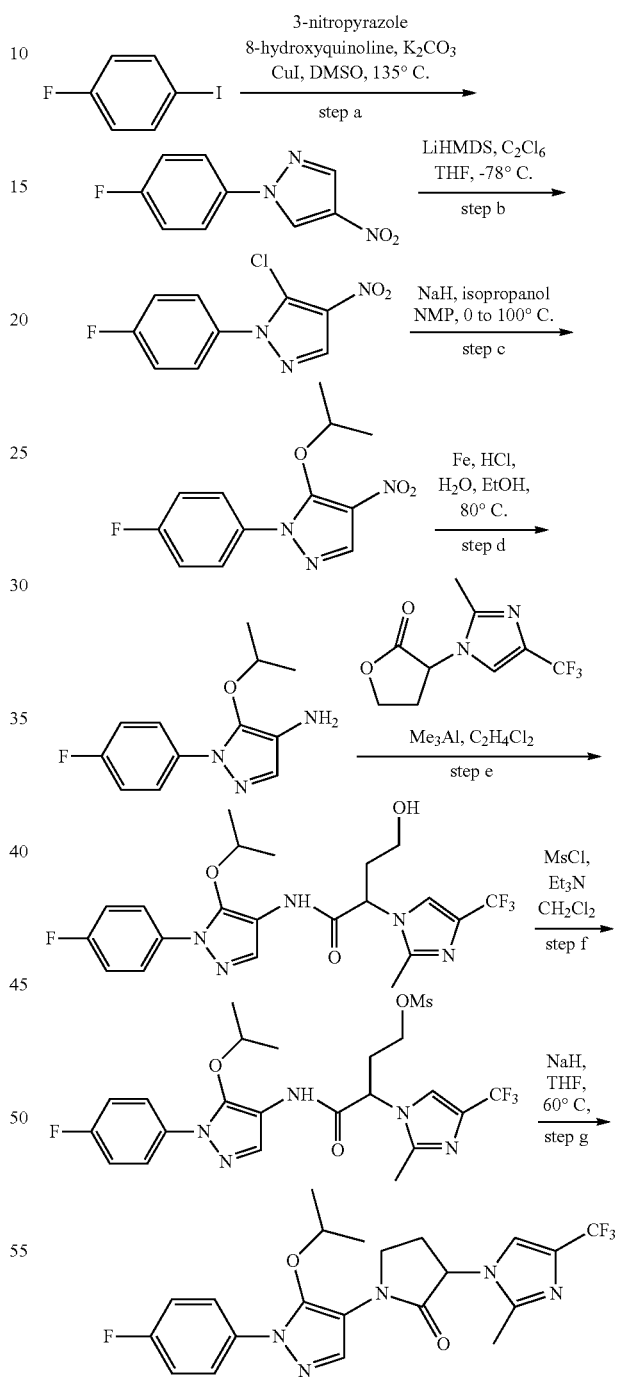

a) A mixture of 4-iodo-fluorobenzene (2.42 g, 11 mmol), 4-nitro-1H-pyrazole (1.00 g, 10 mmol), 8-hyroxyquinoline (0.15 g, 1 mmol), CuI (0.192 g, 1 mmol), and potassium carbonate (2.78 g, 20 mmol) in DMSO (20 mL) was heated at 135° C. overnight. After cooling to room temperature, the reaction mixture was diluted with 30 mL of water and extracted with ethyl acetate. The organic layer was subsequently washed with aqueous saturated sodium bicarbonate, dried (Na$_2$SO$_4$), filtered, and concentrated in vacuo. Purification by flash chromatography (SiO$_2$, 10%-20% EtOAc in hexanes) gave 1.02 g of the desired product (4.9 mmol, 49%).

b) To a solution of 1-(4-fluorophenyl)-4-nitro-pyrazole (1.02 g, 4.9 mmol) in 10 mL of THF was added LiHMDS (1 M in THF, 5.8 mL, 5.8 mmol) at −78° C. under nitrogen. After 30 minutes 1,1,1,2,2,2-hexachloroethane (1.31 g, 5.5 mmol) in 6 mL of THF was added dropwise. The reaction mixture was stirred for an additional 1 hour followed by quenching with 20 mL of aqueous saturated ammonium chloride. Upon warming to room temperature the mixture was extracted with EtOAc. The organic layer was dried (Na$_2$SO$_4$), filtered, and concentrated in vacuo. The resulting crude material was purified by flash chromatography (SiO$_2$, 5%-15% EtOAc in hexanes) to provide 0.61 g of product (2.5 mmol, 52%).

c) To a solution of isopropanol (0.12 g, 2 mmol) in 1 mL of NMP was added NaH (0.085 g, 2 mmol) at 0° C. under nitrogen. After warming to room temperature 5-chloro-1-(4-fluorophenyl)-4-nitro-pyrazole (0.24 g, 1 mmol) was added. The resulting mixture was heated at 100° C. for 3 hours. Upon cooling down to room temperature the reaction was quenched with aqueous saturated sodium bicarbonate and extracted with EtOAc. The organic layer was subsequently dried (Na$_2$SO$_4$), filtered, and concentrated in vacuo. The crude material was used directly in the next step.

d) A mixture of the crude residue from step c, iron powder (0.23 g, 4 mmol), and 100 µL, of aqueous 6 N HCl in 2 mL of EtOH was heated at 80° C. for 20 minutes. Upon cooling to room temperature, the reaction mixture was diluted with 20 mL of aqueous saturated sodium bicarbonate and 40 mL of EtOAc. The resulting suspension was stirred for 10 minutes then filtered through Celite. The organic layer was separated, washed with brine, dried (Na$_2$SO$_4$), filtered, and concentrated in vacuo. The crude material was used directly in the next step.

e) To a mixture of the crude residue from step d (0.042 g, 0.17 mmol) and 2,5-bis[2-methyl-4-(trifluoromethyl)imidazol-1-yl]cyclopentanone (0.053 g, 0.22 mmol) in 1 mL of dichloroethane was added Me$_3$Al (2 N in toluene, 180 µL, 0.36 mmol) at 0° C. After stirring at room temperature for 2 hours the reaction mixture was diluted with 30 mL of water and extracted with EtOAc. The organic layer was subsequently washed with aqueous saturated sodium bicarbonate, dried (Na$_2$SO$_4$), filtered, and concentrated in vacuo. The crude material was used directly in the next step.

f) To a solution of the crude residue from step e and Et$_3$N (0.1 mL) in 1 mL of CH$_2$Cl$_2$ was added MsCl (28 µL, 0.36 mmol). After stirring at room temperature for 2 hours the reaction mixture was diluted with 20 mL of aqueous saturated sodium bicarbonate and 40 mL of EtOAc. The organic layer was subsequently separated, washed with brine, dried (Na$_2$SO$_4$), filtered, and concentrated in vacuo. The crude material was used directly in the next step g) To a solution of the crude residue from step f in 1 mL of THF was added NaH (0.019 g, 0.46 mmol) at 0° C. After 5 minutes at room temperature, the mixture was heated at 60° C. for 2 hours. Upon cooling down to room temperature, the reaction mixture was diluted with 20 mL of aqueous saturated sodium bicarbonate and 40 mL of EtOAc. The organic layer was subsequently separated, washed with brine, dried (Na$_2$SO$_4$), filtered, and concentrated in vacuo. Purification by flash chromatography (SiO$_2$, 60%-100% EtOAc in hexanes) gave the title compound as a white solid (0.026 g, 0.056 mmol, 8.4% for 7 steps). $^1$H NMR (400 MHz, CDCl$_3$) δ 7.81 (s, 1H), 7.70-7.61 (m, 2H), 7.20-7.14 (m, 2H), 4.96 (t, J=9.3 Hz, 1H), 4.15 (p, J=8.0 Hz, 1H), 3.98 (t, J=7.8 Hz, 1H), 3.89 (q, J=7.8 Hz, 1H), 2.93-2.80 (m, 1H), 2.51 (s, 3H), 2.41-2.26 (m, 1H), 1.20 (m, 6H). MS: (ES) m/z calculated for C$_{19}$H$_{20}$F$_4$N$_6$O$_1$ [M+H]$^+$452.1, found 452.3.

Example 30

Synthesis of 1-[1-(4-fluorophenyl)-5-dimethylaminopyrazol-4-yl]-3-[2-methyl-4-(trifluoromethyl)imidazol-1-yl]pyrrolidin-2-one

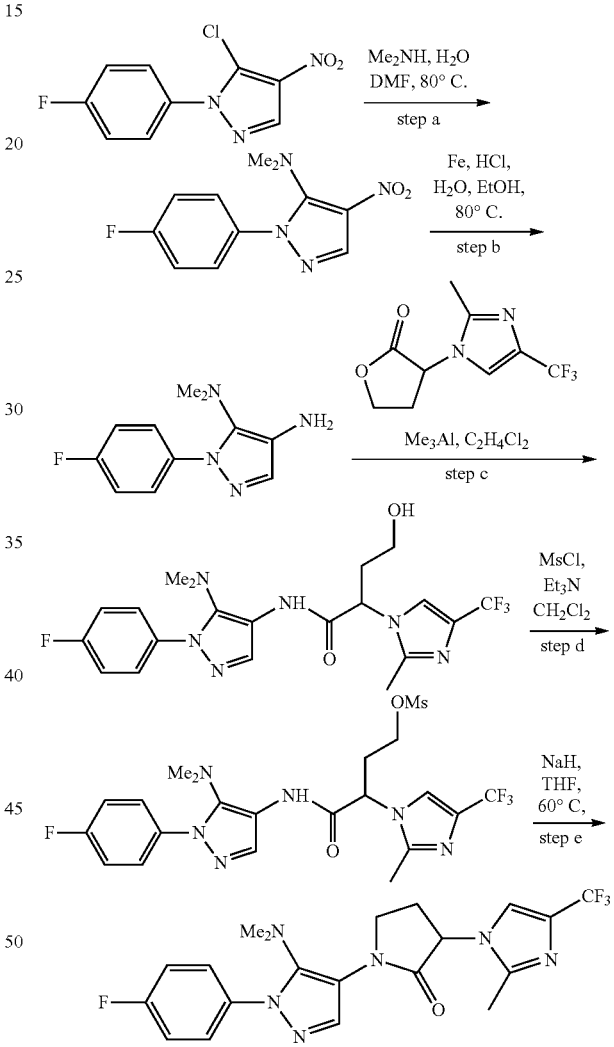

a) A mixture of 5-chloro-1-(4-fluorophenyl)-4-nitro-pyrazole (0.20 g, 0.8 mmol) and dimethylamine (2 M in water, 0.80 mL, 1.6 mmol) in 1 mL of DMF was heated at 80° C. for 2 hours. Upon cooling to room temperature, the reaction mixture was diluted with 20 mL of water, and extracted with EtOAc. The organic layer was subsequently washed with brine, dried (Na$_2$SO$_4$), filtered, and concentrated in vacuo. The crude material was used directly in the next step.

b) A mixture of the crude product from step a, iron powder (0.14 g, 2.5 mmol), and 100 µL of aqueous 6 N HCl in 1 mL of EtOH was heated at 80° C. for 20 minutes. Upon cooling to room temperature, the reaction mixture was diluted with 20 mL of aqueous saturated sodium bicarbonate, and 40 mL of EtOAc. The resulting suspension was stirred for 10 minutes then filtered through Celite. The organic layer was separated, washed with brine, dried (Na₂SO₄), filtered, and concentrated in vacuo. The crude material was used directly in the next step c) To a solution of the crude residue from step b (0.053 g, 0.23 mmol) and 2,5-bis[2-methyl-4-(trifluoromethyl)imidazol-1-yl]cyclopentanone (0.064 g, 0.27 mmol) in 1 mL of dichloroethane was added Me₃Al (2 N in toluene, 130 µL, 0.27 mmol) at 0° C. After stirring at room temperature for 2 hours, the reaction mixture was diluted with 30 mL of aqueous saturated sodium bicarbonate and extracted with EtOAc. The organic layer was subsequently washed with brine, dried (Na₂SO₄), filtered, and concentrated in vacuo. The crude material was used directly in the next step.

d) To a solution of the crude residue from step c and Et₃N in 1 mL of CH₂Cl₂ was added MsCl (36 µL, 0.46 mmol). After stirring at room temperature for 2 hours, the reaction mixture was diluted with 20 mL of aqueous saturated sodium bicarbonate and 40 mL of EtOAc. The organic layer was subsequently separated, washed with brine, dried (Na₂SO₄), filtered, and concentrated in vacuo. The crude material was used directly in the next step e) To a solution of the crude residue from step d in 1 mL of THF was added NaH (0.019 g, 0.46 mmol) at 0° C. After 5 minutes at room temperature, the mixture was heated at 60° C. for 2 hours. Upon cooling down to room temperature, the reaction mixture was diluted with 20 mL of aqueous saturated sodium bicarbonate and 40 mL of EtOAc. The organic layer was subsequently separated, washed with brine, dried (Na₂SO₄), filtered, and concentrated in vacuo. Purification by flash chromatography (SiO₂, 60%-100% EtOAc in hexanes) gave the title compound as a white solid (0.015 g, 0.034 mmol, 15% for 3 steps). ¹H NMR (400 MHz, CDCl₃) δ 7.62-7.58 (m, 2H), 7.53 (s, 1H), 7.23 (s, 1H), 7.18-7.11 (m, 2H), 4.98 (t, J=7.5 Hz, 1H), 4.12 (q, J=7.2 Hz, 1H), 3.94-3.78 (m, 1H), 2.90-2.83 (m, 1H), 2.66 (s, 6H), 2.51 (s, 1H), 2.39-2.33 (m, 1H). MS: (ES) m/z calculated for C₁₉H₂₀F₄N₆O₁ [M+H]⁺437.2, found 437.2.

Example 31

Synthesis of 1-[1-(4-fluorophenyl)-5-isopropylpyrazol-4-yl]-3-[2-methyl-4-(trifluoromethyl)imidazol-1-yl]pyrrolidin-2-one

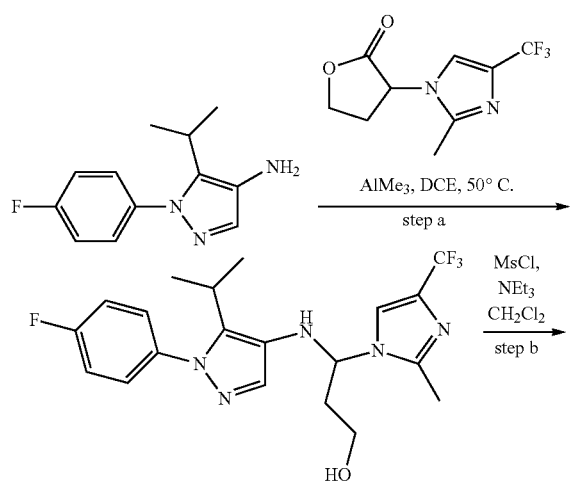

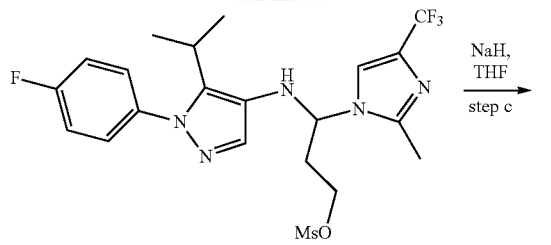

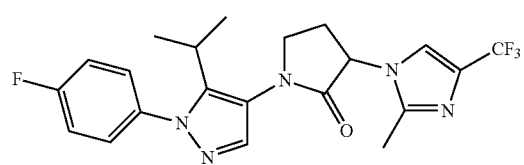

a) A mixture of 1-(4-fluorophenyl)-5-isopropyl-pyrazol-4-amine (0.070 g, 0.32 mmol), 3-[2-methyl-4-(trifluoromethyl)imidazol-1-yl]tetrahydrofuran-2-one (0.070 g, 0.30 mmol) and AlMe₃ (0.50 mL, 1.0 mmol, 2 M/toluene) was heated at 55° C. for 1.5 hrs. The mixture was then cooled to room temperature, diluted with aqueous ammonium hydroxide, and extracted with EtOAc. The organic layer was separated, dried over anhydrous sodium sulfate, concentrated in vacuo, and purified by flash chromatography (SiO₂, 0~20% MeOH/CH₂Cl₂ gradient elution) to give 3-[[1-(4-fluorophenyl)-5-isopropylpyrazol-4-yl]amino]-3-[2-methyl-4-(trifluoromethyl)imidazol-1-yl]propan-1-ol (0.030 g, 24%).

b) A mixture of 3-[[1-(4-fluorophenyl)-5-isopropylpyrazol-4-yl]amino]-3-[2-methyl-4-(trifluoromethyl)imidazol-1-yl]propan-1-ol (0.030 g, 0.070 mmol), methanesulfonyl chloride (0.040 mL, 0.51 mmol) and NEt₃ (0.10 mL, 0.71 mmol) in CH₂Cl₂ (2 mL) was stirred at rt for 10 min. It was then concentrated in vacuo to afford the desired mesylate.

c) A mixture of the above mesylate (~0.070 mmol) was stirred with NaH (0.050 g, 1.25 mmol, 60% in mineral oil) in THF (4 mL) at rt for 10 min. It was then quenched with H₂O (20 mL) and extracted with EtOAc (50 mL). The organic layer was dried over anhydrous sodium sulfate, concentrated in vacuo and purified by reverse phase HPLC (C18 column, acetonitrile-H₂O with 0.1% TFA as eluent) to afford the titled compound (0.022 g, 57%, TFA salt) as a white solid. ¹H NMR (TFA salt) (400 MHz, CDCl₃) δ 7.58 (s, 1H), 7.39 (dd, J=8.4, 4.8 Hz, 2H), 7.28 (s, 1H), 7.20 (dd, J=8.4, 8.4 Hz, 2H), 5.05 (dd, J=10.6, 9.0 Hz, 1H), 3.90 (m, 1H), 3.82 (dd, J=9.0, 9.0 Hz, 1H), 3.01 (heptet, J=7.0 Hz, 1H), 2.90 (m, 1H), 2.60 (s, 3H), 2.41 (m, 1H), 1.222 (d, J=7.2 Hz, 3H), 1.218 (d, J=7.2 Hz, 3H); MS: (ES) m/z calculated for C₂₁H₂₁F₄N₅O (free form) [M+H]⁺436.2, found 436.2.

Example 32

Synthesis of 1-[1-(4-fluorophenyl)-5-isopropylpyrazol-4-yl]-3-[5-methyl-3-(trifluoromethyl)pyrazol-1-yl]pyrrolidin-2-one

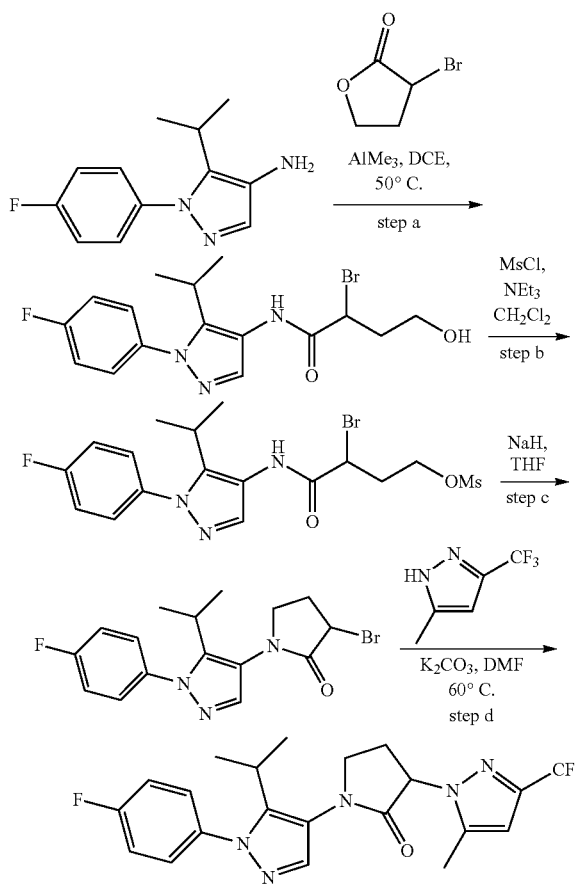

a) A mixture of 1-(4-fluorophenyl)-5-isopropylpyrazol-4-amine (1.0 g, 4.54 mmol), 3-bromotetrahydrofuran-2-one (0.462 mL, 5.0 mmol) and AlMe$_3$ (3.4 mL, 6.8 mmol, 2 M in toluene) in DCE (50 mL) was stirred for 2 hrs at rt followed by 45 min at 50° C. The mixture was then cooled to room temperature, quenched with 1N HCl (50 mL) and extracted with EtOAc (100 mL). The organic layer was separated, dried over anhydrous sodium sulfate, concentrated in vacuo and purified by flash chromatography (SiO$_2$, ~100% EtOAc/CH$_2$Cl$_2$ gradient elution) to give 2-bromo-N-[1-(4-fluorophenyl)-5-isopropylpyrazol-4-yl]-4-hydroxybutanamide (1.38 g, 79%).

b) A mixture of 2-bromo-N-[1-(4-fluorophenyl)-5-isopropyl-pyrazol-4-yl]-4-hydroxy-butanamide (1.38 g, 3.59 mmol), methanesulfonyl chloride (0.36 mL, 4.65 mmol) and NEt$_3$ (0.75 mL, 5.35 mmol) in CH$_2$Cl$_2$ (50 mL) was stirred at 0° C. for 40 min. The mixture was then quenched with water (50 mL) and extracted with EtOAc (100 mL). The organic layer was separated, dried over anhydrous sodium sulfate and concentrated in vacuo to afford the desired mesylate (1.65 g, 99%).

c) A mixture of the above mesylate (0.350 g, 0.75 mmol) was stirred with NaH (0.200 g, 5.0 mmol, 60% in mineral oil) in THF (7 mL) at 50° C. for 30 min. It was then cooled to rt, quenched with saturated aqueous NH$_4$Cl (50 mL) and extracted with EtOAc (50 mL). The organic layer was dried over anhydrous sodium sulfate, concentrated in vacuo and purified by flash chromatography (SiO$_2$, 0-80% EtOAc/CH$_2$Cl$_2$ gradient elution) to give 3-bromo-1-[1-(4-fluorophenyl)-5-isopropylpyrazol-4-yl]pyrrolidin-2-one (0.160 g, 58%).

d) A mixture of 3-bromo-1-[1-(4-fluorophenyl)-5-isopropylpyrazol-4-yl]pyrrolidin-2-one (0.023 g, 0.063 mmol), 5-methyl-3-(trifluoromethyl)-1H-pyrazole (0.040 g, 0.27 mmol) and K$_2$CO$_3$ (0.060 g, 0.43 mmol) in DMF (1 mL) was stirred at 60° C. for 1 hr. It was then cooled to room temperature, quenched with water (30 mL) and extracted with EtOAc (100 mL). The organic layer was separated, dried over anhydrous sodium sulfate, concentrated in vacuo and purified by flash chromatography (SiO$_2$, 0~100% EtOAc/hexanes gradient elution) to give the title compound (0.022 g, 80%). $^1$H NMR (400 MHz, CDCl$_3$) δ 7.52 (s, 1H), 7.37 (dd, J=9.2, 4.8 Hz, 2H), 7.17 (dd, J=8.6, 8.6 Hz, 2H), 6.32 (s, 1H), 5.05 (dd, J=9.2, 5.6 Hz, 1H), 4.07 (m, 1H), 3.80 (m, 1H), 2.84-3.02 (m, 2H), 2.74 (m, 1H), 2.45 (s, 3H), 1.21 (d, J=7.6 Hz, 3H), 1.11 (d, J=6.8 Hz, 3H); MS: (ES) m/z calculated for C$_{21}$H$_{21}$F$_4$N$_5$O [M+H]$^+$ 436.1, found 436.1.

Example 33

Synthesis of 1-[1-(4-fluorophenyl)-5-isopropylpyrazol-4-yl]-3-[3-(1H-imidazol-2-yl)pyrazolo[3,4-b]pyridin-1-yl]pyrrolidin-2-one

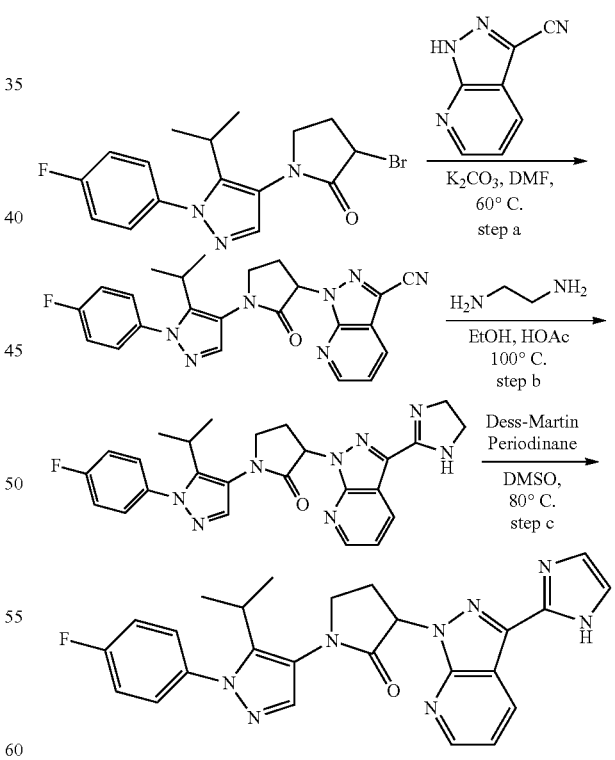

a) A mixture of 3-bromo-1-[1-(4-fluorophenyl)-5-isopropylpyrazol-4-yl]pyrrolidin-2-one (0.080 g, 0.22 mmol), 1H-pyrazolo[3,4-b]pyridine-3-carbonitrile (0.045 g, 0.31 mmol) and K$_2$CO$_3$ (0.070 g, 0.50 mmol) in DMF (2.5 mL) was stirred at 60° C. for 1 hr. It was then cooled to room temperature, quenched with water (30 mL) and extracted with EtOAc (100 mL). The organic layer was separated, dried over anhydrous sodium sulfate, concentrated in vacuo and purified by flash chromatography (SiO$_2$, 0~100% EtOAc/hexanes gradient elution) to give 1-[1-[1-(4-fluorophenyl)-5-isopropyl-pyrazol-4-yl]-2-oxo-pyrrolidin-3-yl]pyrazolo[3,4-b]pyridine-3-carbonitrile (0.085 g, 88%).

b) A mixture of 1-[1-[1-(4-fluorophenyl)-5-isopropyl-pyrazol-4-yl]-2-oxo-pyrrolidin-3-yl]pyrazolo[3,4-b]pyridine-3-carbonitrile (0.082 g, 0.19 mmol) in ethane-1,2-diamine (1 mL), HOAc (0.1 mL) and EtOH (2.5 mL) was stirred at 100° C. for 1 hr. The mixture was then cooled to room temperature, quenched with saturated aqueous NaHCO$_3$ (50 mL) and extracted with EtOAc (100 mL). The organic layer was separated, dried over anhydrous sodium sulfate and concentrated in vacuo to afford 3-[3-(4,5-dihydro-1H-imidazol-2-yl)pyrazolo[3,4-b]pyridin-1-yl]-1-[1-(4-fluorophenyl)-5-isopropylpyrazol-4-yl]pyrrolidin-2-one (0.085 g, 94%).

c) A mixture of 3-[3-(4,5-dihydro-1H-imidazol-2-yl)pyrazolo[3,4-b]pyridin-1-yl]-1-[1-(4-fluorophenyl)-5-isopropylpyrazol-4-yl]pyrrolidin-2-one (0.085 g, 0.18 mmol) and Dess-Martin periodinane (0.153 g, 0.36 mmol) in DMSO (2.5 mL) was stirred at 80° C. for 1 hr. It was then cooled to room temperature, quenched with sat. aq. NaHCO$_3$ (50 mL), and extracted with EtOAc (50 mL). The organic layer was separated, dried over anhydrous sodium sulfate, concentrated in vacuo and purified by flash chromatography (SiO$_2$, ~7% MeOH/EtOAc gradient elution) to give the title compound (0.070 g, 82%). $^1$H NMR (400 MHz, CDCl$_3$) δ 10.42 (s, 1H, br), 8.74 (dd, J=8.4, 1.6 Hz, 1H), 8.54 (dd, J=4.8, 1.6 Hz, 1H), 7.64 (s, 1H), 7.40 (dd, J=6.8, 4.6 Hz, 2H), 7.23 (m, 1H), 7.18 (dd, J=8.6 Hz, 2H), 6.94 (s, 1H, br), 5.94 (dd, J=9.2, 9.2 Hz, 1H), 3.94 (m, 3H), 3.07 (heptet, J=6.8, 1H), 2.75-2.95 (m, 2H), 1.33 (d, J=7.6 Hz, 3H), 1.28 (d, J=7.2 Hz, 3H); MS: (ES) m/z calculated for C$_{25}$H$_{23}$FN$_8$O [M+H]$^+$471.2, found 471.2.

Example 34

Synthesis of 3-[4-chloro-3-(1-hydroxy-1-methylethyl)-5-methyl-pyrazol-1-yl]-1-[1-(4-fluorophenyl)-5-isopropylpyrazol-4-yl]pyrrolidin-2-one and 3-[4-chloro-5-(1-hydroxy-1-methylethyl)-3-methyl-pyrazol-1-yl]-1-[1-(4-fluorophenyl)-5-isopropylpyrazol-4-yl]pyrrolidin-2-one

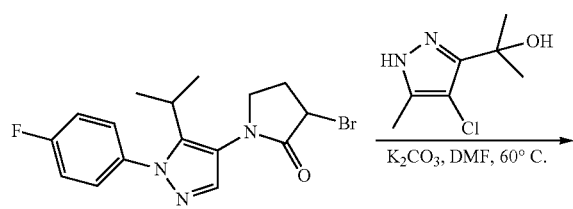

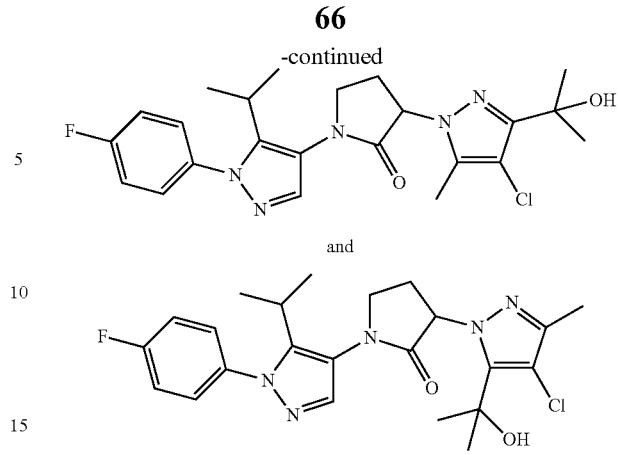

A mixture of 3-bromo-1-[1-(4-fluorophenyl)-5-isopropylpyrazol-4-yl]pyrrolidin-2-one (0.045 g, 0.20 mmol), 2-(4-chloro-5-methyl-1H-pyrazol-3-yl)propan-2-ol (0.070 g, 0.40 mmol) and K$_2$CO$_3$ (0.05 g, 0.40 mmol) in DMF (1.5 mL) was stirred at 60° C. for 1.5 hrs. It was then cooled to room temperature, quenched with water (30 mL) and extracted with EtOAc (50 mL). The organic layer was separated, dried over anhydrous sodium sulfate, concentrated in vacuo and purified by reverse phase HPLC (C18 column, acetonitrile-H$_2$O with 0.1% TFA as eluent) to yield two pure fractions. The first fraction corresponded to 3-[4-Chloro-3-(1-hydroxy-1-methylethyl)-5-methylpyrazol-1-yl]-1-[1-(4-fluorophenyl)-5-isopropylpyrazol-4-yl]pyrrolidin-2-one (0.012 g, 13%). The second fraction corresponded to 3-[4-Chloro-5-(1-hydroxy-1-methylethyl)-3-methylpyrazol-1-yl]-1-[1-(4-fluorophenyl)-5-isopropylpyrazol-4-yl]pyrrolidin-2-one (0.012 g, 13%). $^1$H NMR of 3-[4-Chloro-3-(1-hydroxy-1-methylethyl)-5-methylpyrazol-1-yl]-1-[1-(4-fluorophenyl)-5-isopropylpyrazol-4-yl]pyrrolidin-2-one (400 MHz, CDCl$_3$): δ 7.59 (s, 1H), 7.38 (dd, J=9.0, 4.8 Hz, 2H), 7.19 (dd, J=8.4, 8.4 Hz, 2H), 5.02 (dd, J=9.6, 7.2 Hz, 1H), 4.68 (s, 1H, br), 3.98 (m, 1H), 3.82 (m, 1H), 2.97 (heptet, J=7.0 Hz, 1H), 2.85 (m, 1H), 2.72 (m, 1H), 2.35 (s, 3H), 1.59 (d, J=8.4 Hz, 6H), 1.24 (d, J=7.2 Hz, 3H), 1.16 (d, J=7.2 Hz, 3H); $^1$H NMR of 3-[4-Chloro-5-(1-hydroxy-1-methylethyl)-3-methylpyrazol-1-yl]-1-[1-(4-fluorophenyl)-5-isopropylpyrazol-4-yl]pyrrolidin-2-one (400 MHz, CDCl$_3$) δ 7.54 (s, 1H), 7.36 (dd, J=8.8, 4.4 Hz, 2H), 7.17 (dd, J=8.6, 8.6 Hz, 2H), 6.13 (m, 1H), 4.08 (m, 1H), 3.76 (m, 1H), 3.16 (m, 1H), 2.91 (heptet, J=7.0 Hz, 1H), 2.88 (s, ! H, br), 2.65 (m, 1H), 2.18 (s, 3H), 1.79 (s, 3H), 1.62 (s, 3H), 1.14 (d, J=6.8 Hz, 3H), 1.03 (d, J=7.2 Hz, 3H); MS (equal value for both compounds): (ES) m/z calculated for C$_{23}$H$_{27}$ClFN$_5$O$_2$ [M+H]$^+$460.2, found 460.2.

Example 35

Synthesis of 1-[1-(4-fluorophenyl)-5-isopropylpyrazol-4-yl]-3-[4-(trifluoromethyl)imidazol-1-yl]pyrrolidin-2-one

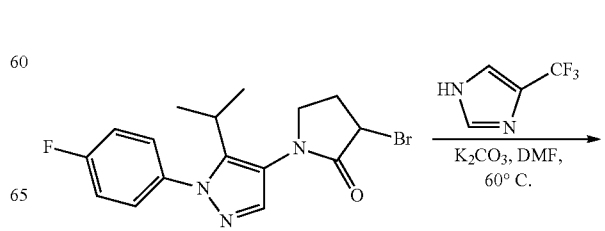

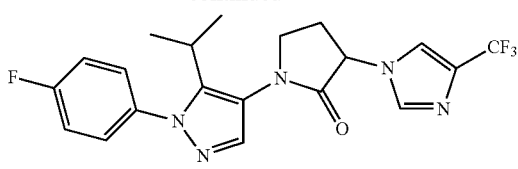
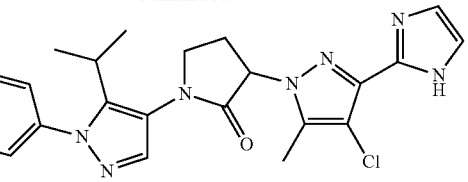

A mixture of 3-bromo-1-[1-(4-fluorophenyl)-5-isopropyl-pyrazol-4-yl]pyrrolidin-2-one (0.020 g, 0.055 mmol), 4-(trifluoromethyl)-1H-imidazole (0.024 g, 0.17 mmol) and K$_2$CO$_3$ (0.030 g, 0.22 mmol) in DMF (0.6 mL) was stirred at 60° C. for 1 hr. The mixture was then cooled to room temperature, quenched with water (30 mL) and extracted with EtOAc (50 mL). The organic layer was separated, dried over anhydrous sodium sulfate, concentrated in vacuo and purified by reverse phase HPLC (C18 column, acetonitrile H$_2$O with 0.1% TFA as eluent) to yield the title compound (0.022 g, TFA salt, 75%); $^1$H NMR (TFA salt) (400 MHz, CDCl$_3$) δ 7.98 (s, 1H), 7.59 (s, 1H), 7.51 (s, 1H), 7.39 (dd, J=8.4, 4.8 Hz, 2H), 7.20 (dd, J=8.6, 8.6 Hz, 2H), 5.06 (dd, J=10.8, 8.8 Hz, 1H), 3.90 (m, 1H), 3.83 (m, 1H), 2.98 (m, 2H), 2.54 (m, 1H), 1.21 (d, J=7.2 Hz, 3H), 1.20 (d, J=7.2 Hz, 3H); MS: (ES) m/z calculated for C$_{20}$H$_{19}$F$_4$N$_5$O (free form) [M+H]$^+$422.1, found 422.1.

Example 36

Synthesis of 3-[4-chloro-3-(1H-imidazol-2-yl)-5-methylpyrazol-1-yl]-1-[1-(4-fluorophenyl)-5-isopropylpyrazol-4-yl]pyrrolidin-2-one

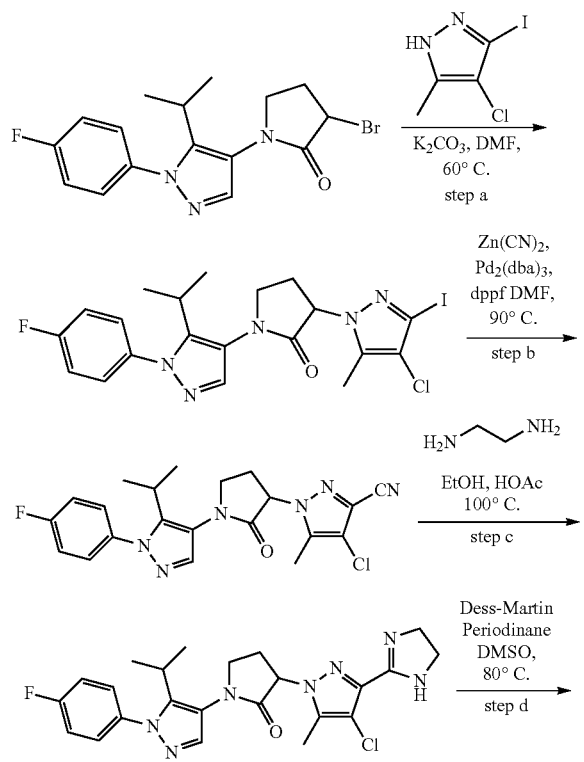

a) A mixture of 3-bromo-1-[1-(4-fluorophenyl)-5-isopropylpyrazol-4-yl]pyrrolidin-2-one (0.055 g, 0.15 mmol), (0.055 g, 0.23 mmol) and K$_2$CO$_3$ (0.042 g, 0.30 mmol) in DMF (1.5 mL) was stirred at 60° C. for 1 hr. The mixture was then cooled to room temperature, quenched with water (30 mL) and extracted with EtOAc (50 mL). The organic layer was separated, dried over anhydrous sodium sulfate, concentrated in vacuo and purified by flash chromatography (SiO$_2$, 0~100% EtOAc/CH$_2$Cl$_2$ gradient elution) to give 3-(4-chloro-3-iodo-5-methylpyrazol-1-yl)-1-[1-(4-fluorophenyl)-5-isopropylpyrazol-4-yl]pyrrolidin-2-one (0.057 g, 72%).

b) A mixture of 3-(4-chloro-3-iodo-5-methylpyrazol-1-yl)-1-[1-(4-fluorophenyl)-5-isopropylpyrazol-4-yl]pyrrolidin-2-one (0.057 g, 0.11 mmol), Zn(CN)$_2$ (0.025 g, 0.21 mmol), Pd$_2$(dba)$_3$ (0.010 g, 0.011 mmol) and dppf (0.009 g, 0.016 mmol) in DMF (2 mL) was heated at 85° C. for 1 h under a N$_2$ atmosphere. The mixture was then cooled to room temperature, quenched with sat. NaHCO$_3$ (30 mL,) and extracted with EtOAc (50 mL). The organic layer was separated, dried over anhydrous sodium sulfate, concentrated in vacuo and purified by flash chromatography (SiO$_2$, 0~100% EtOAc/CH$_2$Cl$_2$ gradient elution) to give 4-chloro-1-[1-[1-(4-fluorophenyl)-5-isopropylpyrazol-4-yl]-2-oxo-pyrrolidin-3-yl]-5-methylpyrazole-3-carbonitrile (0.042 g, 92%).

c) A mixture of 4-chloro-1-[1-[1-(4-fluorophenyl)-5-isopropylpyrazol-4-yl]-2-oxo-pyrrolidin-3-yl]-5-methylpyrazole-3-carbonitrile (0.042 g, 0.10 mmol) in ethane-1,2-diamine (1.5 mL), HOAc (0.23 mL) and EtOH (1.25 mL) was stirred at 100° C. for 2.5 hrs. The mixture was then cooled to room temperature, quenched with sat. aq. NaHCO$_3$ (50 mL), and extracted with EtOAc (100 mL). The organic layer was separated, dried over anhydrous sodium sulfate and concentrated in vacuo to afford 3-[4-chloro-3-(4,5-dihydro-1H-imidazol-2-yl)-5-methylpyrazol-1-yl]-1-[1-(4-fluorophenyl)-5-isopropylpyrazol-4-yl]pyrrolidin-2-one (0.041 g, 87%).

d) A mixture of 3-[4-chloro-3-(4,5-dihydro-1H-imidazol-2-yl)-5-methylpyrazol-1-yl]-1-[1-(4-fluorophenyl)-5-isopropylpyrazol-4-yl]pyrrolidin-2-one (0.041 g, 0.087 mmol) and Dess-Martin periodinane (0.150 g, 0.35 mmol) in DMSO (2.0 mL) was stirred at 80° C. for 1.5 hr. The mixture was then cooled to room temperature, quenched with sat. aq. NaHCO$_3$ (50 mL), and extracted with EtOAc (50 mL). The organic layer was separated, dried over anhydrous sodium sulfate, concentrated in vacuo and purified by reverse phase HPLC (C18 column, acetonitrile H$_2$O with 0.1% TFA as eluent) to yield the title compound (0.025 g, TFA salt, 50%). $^1$H NMR (TFA salt) (400 MHz, CDCl$_3$) δ 7.62 (s, 1H), 7.35 (dd, J=8.4, 4.8 Hz, 2H), 7.16 (m, 4H), 5.15 (dd, J=8.6, 8.6 Hz, 1H), 4.02 (m, 1H), 3.82 (m, 1H), 3.05 (m, 1H), 2.97 (septet, J=7.0 Hz, 1H), 2.35 (s, 3H), 2.70 (m, 1H), 1.18 (d, J=6.8 Hz, 3H), 1.14 (d, J=6.8 Hz, 3H); MS: (ES) m/z calculated for C$_{23}$H$_{23}$ClFN$_7$O (free form) [M+H]$^+$468.1, found 468.1.

Example 37

Synthesis of 3-[4-amino-3-(1H-imidazol-2-yl)pyrazolo[3,4-d]pyrimidin-1-yl]-1-[1-(4-fluorophenyl)-5-isopropylpyrazol-4-yl]pyrrolidin-2-one

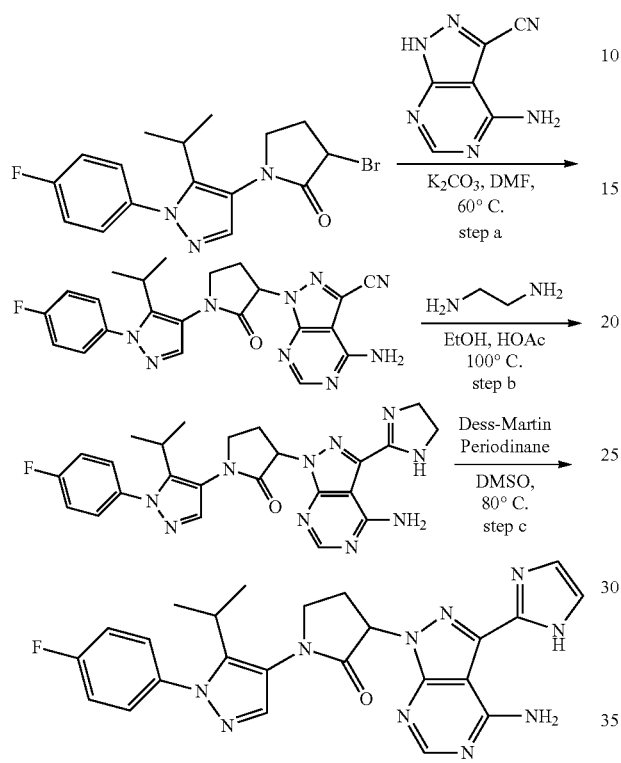

a) A mixture of 3-bromo-1-[1-(4-fluorophenyl)-5-isopropylpyrazol-4-yl]pyrrolidin-2-one (0.055 g, 0.15 mmol), 4-amino-1H-pyrazolo[3,4-d]pyrimidine-3-carbonitrile (0.050 g, 0.31 mmol) and K$_2$CO$_3$ (0.050 g, 0.36 mmol) in DMF (2.0 mL) was stirred at 60° C. for 1 hr. The mixture was then cooled to room temperature, quenched with water (30 mL), and extracted with IPA: CHCl$_3$ (1:2 v/v, 100 mL). The organic layer was separated, dried over anhydrous sodium sulfate, concentrated in vacuo and purified by flash chromatography (SiO$_2$, 0~10% MeOH/EtOAc gradient elution) to give 4-amino-1-[1-[1-(4-fluorophenyl)-5-isopropylpyrazol-4-yl]-2-oxo-pyrrolidin-3-yl]pyrazolo[3,4-d]pyrimidine-3-carbonitrile (0.055 g, 82%).

b) A mixture of 4-amino-1-[1-[1-(4-fluorophenyl)-5-isopropylpyrazol-4-yl]-2-oxo-pyrrolidin-3-yl]pyrazolo[3,4-d]pyrimidine-3-carbonitrile (0.055 g, 0.12 mmol) in ethane-1,2-diamine (1.5 mL), HOAc (0.23 mL), and EtOH (2.0 mL) was stirred at 100° C. for 45 min. The mixture was then cooled to room temperature, quenched with sat. aq. NaHCO$_3$ (50 mL), and extracted with IPA: CHCl$_3$ (1:2 v/v, 100 mL). The organic layer was separated, dried over anhydrous sodium sulfate and concentrated in vacuo to afford 3-[4-amino-3-(4,5-dihydro-1H-imidazol-2-yl)pyrazolo[3,4-d]pyrimidin-1-yl]-1-[1-(4-fluorophenyl)-5-isopropylpyrazol-4-yl]pyrrolidin-2-one (0.057 g, 97%).

c) A mixture of 3-[4-amino-3-(4,5-dihydro-1H-imidazol-2-yl)pyrazolo[3,4-d]pyrimidin-1-yl]-1-[1-(4-fluorophenyl)-5-isopropylpyrazol-4-yl]pyrrolidin-2-one (0.057 g, 0.12 mmol) and Dess-Martin periodinane (0.100 g, 0.23 mmol) in DMSO (3 mL) was stirred at 80° C. for 45 min. The mixture was then cooled to room temperature, quenched with sat. aq. NaHCO$_3$ (50 mL), and extracted with EtOAc (50 mL). The organic layer was separated, dried over anhydrous sodium sulfate, concentrated in vacuo and purified by reverse phase HPLC (C18 column, acetonitrile-H$_2$O with 0.1% TFA as eluent) to yield the title compound (0.035 g, TFA salt, 48%). $^1$H NMR (TFA salt) (400 MHz, CDCl$_3$) δ 11.96 (s, 1H), 11.12 (s, 1H), 8.17 (s, 1H), 7.65 (s, 1H), 7.40 (dd, J=8.8, 4.4 Hz, 2H), 7.20 (dd, J=8.6, 8.6 Hz, 1H), 7.05 (s, 2H, br), 5.74 (dd, J=9.2, 9.2 Hz, 1H) 3.94 (dd, J=8.4, 4.4 Hz, 2H), 3.05 (m, 1H), 3.07 (septet, J=7.0 Hz, 1H), 2.87 (m, 2H), 1.31 (d, J=6.8 Hz, 3H), 1.27 (d, J=6.8 Hz, 3H); MS: (ES) m/z calculated for C$_{24}$H$_{23}$FN$_{10}$O (free form) [M+H]$^+$487.2, found 487.2.

Example 38

Synthesis of 1-[1-(4-fluorophenyl)-5-isopropylpyrazol-4-yl]-3-[3-(trifluoromethyl)pyrazol-1-yl]pyrrolidin-2-one

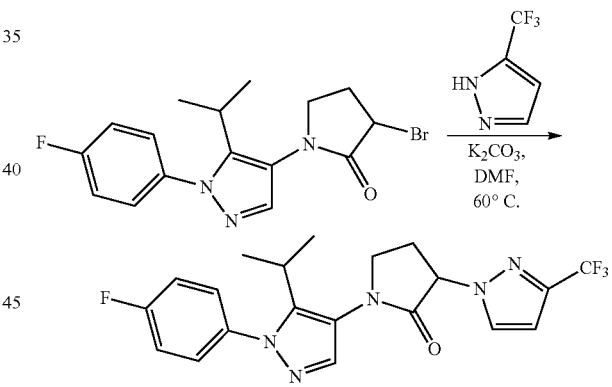

A mixture of 3-bromo-1-[1-(4-fluorophenyl)-5-isopropylpyrazol-4-yl]pyrrolidin-2-one (0.015 g, 0.041 mmol), 5-(trifluoromethyl)-1H-pyrazole (0.030 g, 0.22 mmol) and K$_2$CO$_3$ (0.030 g, 0.22 mmol) in DMF (0.5 mL) was stirred at 60° C. for 40 min. The mixture was then cooled to room temperature, quenched with water (30 mL), extracted with EtOAc (50 mL), and purified by reverse phase HPLC (C18 column, acetonitrile-H$_2$O with 0.1% TFA as eluent) to yield the title compound (0.014 g, 81%). $^1$H NMR (400 MHz, CDCl$_3$) δ 7.70 (d, J=1.6 Hz, 1H), 7.57 (s, 1H), 7.38 (dd, J=8.8, 4.8 Hz, 2H), 7.18 (dd, J=8.4, 8.4 Hz, 2H), 6.58 (d, J=2.4 Hz, 1H), 5.07 (dd, J=8.8, 7.2 Hz, 1H), 4.03 (m, 1H), 3.82 (m, 1H), 2.97 (heptet, J=7.6 Hz, 1H), 2.84 (m, 2H), 1.20 (d, J=7.2 Hz, 3H), 1.12 (d, J=7.2 Hz, 3H); MS: (ES) m/z calculated for C$_{20}$H$_{19}$F$_4$N$_5$O [M+H]$^+$422.1, found 422.1.

Example 39

Synthesis of 3-[4-chloro-5-methyl-3-(trifluoromethyl)pyrazol-1-yl]-1-[1-(4-chlorophenyl)-5-isopropylpyrazol-4-yl]pyrrolidin-2-one

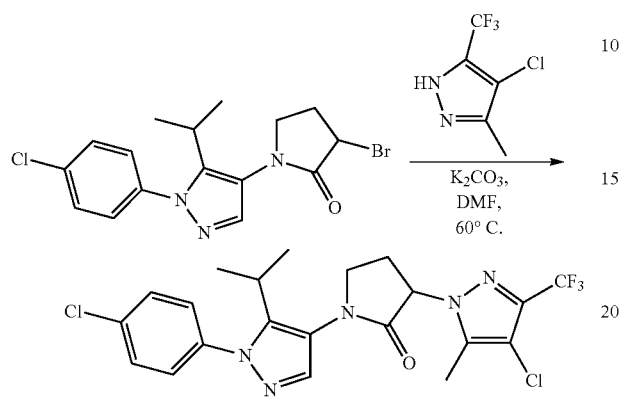

A mixture of 3-bromo-1-[1-(4-chlorophenyl)-5-isopropylpyrazol-4-yl]pyrrolidin-2-one (0.035 g, 0.095 mmol), 4-chloro-3-methyl-5-(trifluoromethyl)-1H-pyrazole (0.050 g, 0.27 mmol) and K$_2$CO$_3$ (0.050 g, 0.36 mmol) in DMF (0.8 mL) was stirred at 60° C. for 40 min. The mixture was then cooled to room temperature, quenched with water (30 mL), extracted with EtOAc (50 mL), and purified by reverse phase HPLC (C18 column, acetonitrile-H$_2$O with 0.1% TFA as eluent) to yield the title compound (0.036 g, 78%). $^1$H NMR (400 MHz, CDCl$_3$) δ 7.57 (s, 1H), 7.47 (m, 2H), 7.34 (m, 2H), 5.05 (dd, J=9.2, 6.0 Hz, 1H), 4.04 (m, 1H), 3.81 (m, 1H), 2.99 (heptet, J=6.8 Hz, 1H), 2.87 (m, 1H), 2.76 (m, 1H), 2.42 (s, 3H), 1.22 (d, J=7.2 Hz, 3H), 1.12 (d, J=7.2 Hz, 3H); MS: (ES) m/z calculated for C$_{21}$H$_{20}$Cl$_2$F$_3$N$_5$O [M+H]$^+$ 486.1, found 486.1.

Example 40

Synthesis of 1-[1-(4-chlorophenyl)-5-isopropylpyrazol-4-yl]-3-[2-methyl-4-(trifluoromethyl)imidazol-1-yl]pyrrolidin-2-one

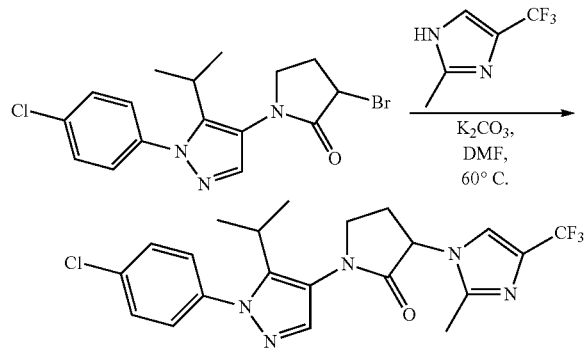

A mixture of 3-bromo-1-[1-(4-chlorophenyl)-5-isopropylpyrazol-4-yl]pyrrolidin-2-one (0.110 g, 0.29 mmol), 2-methyl-4-(trifluoromethyl)-1H-imidazole (0.080 g, 0.53 mmol) and K$_2$CO$_3$ (0.080 g, 0.58 mmol) in DMF (1.8 mL) was stirred at 65° C. for 2 hrs. The mixture was then cooled to room temperature, quenched with water (30 mL), extracted with EtOAc (50 mL), and purified by reverse phase HPLC (C18 column, acetonitrile H$_2$O with 0.1% TFA as eluent) to yield the title compound (0.035 g, TFA salt, 21%). $^1$H NMR (TFA salt) (400 MHz, CDCl$_3$) δ 7.58 (s, 1H), 7.49 (m, 2H), 7.35 (m, 2H), 7.27 (s, 1H), 5.03 (dd, J=10.4, 8.8 Hz, 1H), 3.89 (m, 1H), 3.81 (m, 1H), 3.04 (heptet, J=6.8 Hz, 1H), 2.88 (m, 1H), 2.58 (s, 3H), 2.40 (m, 1H), 1.23 (m, 6H); MS: (ES) m/z calculated for C$_{21}$H$_{21}$ClF$_3$N$_5$O [M+]$^+$452.1, found 452.1.

Example 41

Synthesis of 1-[1-(4-chlorophenyl)-5-isopropylpyrazol-4-yl]-3-[2-ethyl-4-(trifluoromethyl)imidazol-1-yl]pyrrolidin-2-one

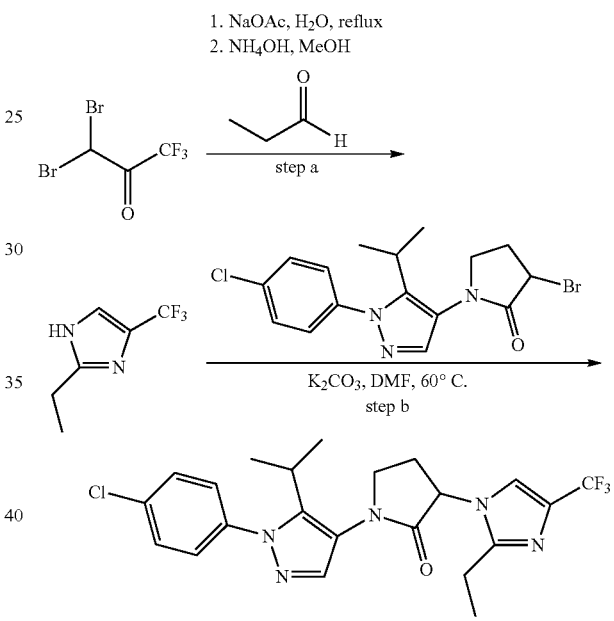

a) A mixture of 3,3-dibromo-1,1,1-trifluoro-propan-2-one (5.40 g, 20 mmol) and sodium acetate trihydrate (5.44 g, 40 mmol) in water (40 mL) was refluxed for 30 min and then allowed to cool to rt. A solution of propanal (1.04 g, 18 mmol) and conc. ammonium hydroxide (1.2 mL) in MeOH (100 mL) was added to the above mixture slowly. The resulting mixture was stirred at rt for 3 days. The mixture was then concentrated in vacuo and extracted with IPA:CHCl$_3$ (1:2 v/v, 200 mL). The organic layer was separated, dried over anhydrous sodium sulfate, concentrated in vacuo, and purified by flash chromatography (SiO$_2$, 0~6% MeOH/EtOAc and 0~0.6% NH$_4$OH gradient elution) to give 2-ethyl-4-(trifluoromethyl)-1H-imidazole (0.070 g, 2.3%).

b) A mixture of 3-bromo-1-[1-(4-chlorophenyl)-5-isopropylpyrazol-4-yl]pyrrolidin-2-one (0.200 g, 0.52 mmol), 2-ethyl-4-(trifluoromethyl)-1H-imidazole (0.060 g, 0.36 mmol) and K$_2$CO$_3$ (0.080 g, 0.58 mmol) in DMF (1.5 mL) was stirred at 65° C. for 1.5 hrs. The mixture was then cooled to room temperature, quenched with water (30 mL), extracted with EtOAc (50 mL), and purified by reverse phase HPLC (C18 column, acetonitrile H$_2$O with 0.1% TFA as eluent) to yield the title compound (0.0022 g, TFA salt, 1.0%). $^1$H NMR (TFA salt) (400 MHz, CDCl$_3$) δ 7.58 (s, 1H), 7.49 (m, 2H), 7.35 (m, 2H), 7.21 (s, 1H), 5.03 (dd, J=10.4, 8.8 Hz, 1H), 3.88 (m, 1H), 3.81 (m, 1H), 3.03 (heptet, J=7.0 Hz, 1H), 2.88 (m, 2H), 2.30 (m, 2H), 1.40 (t, J=7.4 Hz, 3H), 1.23 (m, 6H); MS: (ES) m/z calculated for C$_{22}$H$_{23}$ClF$_3$N$_5$O [M+H]$^+$466.1, found 466.1.

Example 42

Synthesis of (S)-1-(1-(4-chlorophenyl)-5-isopropyl-1H-pyrazol-4-yl)-3-(2-methyl-4-(trifluoromethyl)-1H-imidazol-1-yl)pyrrolidin-2-one and (R)-1-(1-(4-chlorophenyl)-5-isopropyl-1H-pyrazol-4-yl)-3-(2-methyl-4-(trifluoromethyl)-1H-imidazol-1-yl)pyrrolidin-2-one

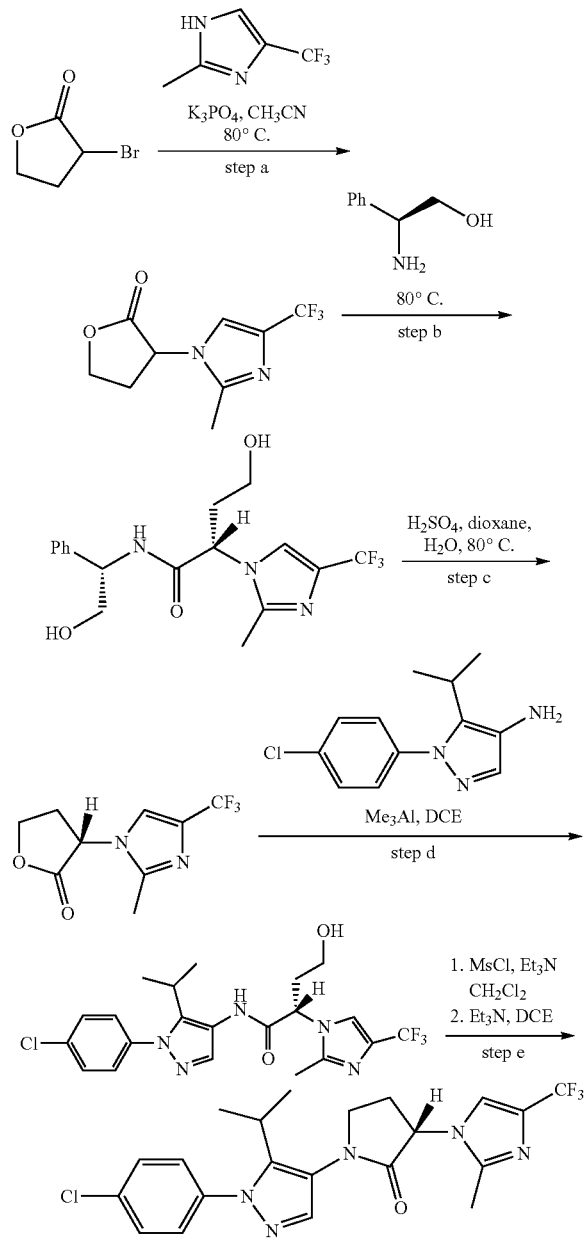

a) To a solution of α-bromo-γ-valerolactone (19.8 g, 120 mmol) and 2-methyl-4-(trifluoromethyl)-1H-imidazole (4.50 g, 30 mmol) in acetonitrile (60 mL) was added K$_3$PO$_4$ (19.1 g, 90 mmol). The slurry was heated to 80° C. for 2 days, then cooled to room temperature, diluted with EtOAc (200 mL), filtered through Celite, and concentrated. The residue was purified by flash chromatography (SiO$_2$, 0-3.5% methanol/CH$_2$Cl$_2$) to give the product as a pasty colorless solid.

b) A mixture of the lactone intermediate (700 mg, 5.1 mmol) from step a and (S)-phenylglycinol (1.09 g, 4.64 mmol) was heated at 80° C. for 18 h, cooled to room temperature, and purified by flash chromatography (SiO$_2$, 0.5-2% methanol/EtOAc) to give two diastereomeric products as colorless foams. The first eluting isomer (310 mg) was obtained in 99:1 diastereomeric ratio CH NMR) and the second eluting isomer (200 mg) in 11:1 diastereomeric ratio ($^1$H NMR). Each diastereomer was carried through steps c and d independently.

c) To a mixture of the product from step b (186 mg, 0.5 mmol) in dioxane (2 mL) was added 6 M H$_2$SO$_4$ (1.25 mL, 7.5 mmol). The resulting slurry was heated at 80° C. for 1 h, cooled to room temperature, and purified by reverse phase HPLC (C18 column, acetonitrile-H$_2$O with 0.1% TFA as eluent). The resulting lactone·TFA salt was neutralized to provide a colorless solid (53 mg, 0.23 mmol) that was used without further purification.

d) A mixture of the lactone product from step c and 1-(4-chlorophenyl)-5-isopropyl-1H-pyrazol-4-amine (50 mg, 0.21 mmol) in 1,2-dichloroethane (1 mL) was treated with AlMe$_3$ (2 M solution in toluene, 210 μL, 0.42 mmol) at room temperature for 30 min. The reaction was quenched with saturated NH$_4$Cl (5 mL) and extracted with EtOAc (3×3 mL). The organic layer was dried on MgSO$_4$, filtered, concentrated, and purified by flash chromatography (SiO$_2$, 0-100% EtOAc/CH$_2$Cl$_2$) to give the desired product (50 mg, 0.1 mmol, 50% yield).

e) The product from step d (50 mg, 0.1 mmol) in dichloromethane (0.5 mL) was treated with Et$_3$N (40 μL, 0.29 mmol) and methanesulfonyl chloride (20 μL, 0.23 mmol) for 30 min at room temperature. The mixture was then diluted with 1,2-dichloroethane (1 mL) and washed with water (1 mL). The organic layer was dried on Na$_2$SO$_4$ and filtered. To the filtrate was added triethylamine (100 μL, 0.7 mmol) and the mixture was stirred at 65° C. for 90 min, concentrated, and purified by reverse phase HPLC (C18 column, acetonitrile-H$_2$O with 0.1% TFA as eluent). The resulting TFA salt was neutralized to provide the titled compound (19 mg, 0.041 mmol) as a white solid. $^1$H NMR (400 MHz, CDCl$_3$) δ 7.55 (s, 1H), 7.48 (d, J=8.6, 2H), 7.36 (d, J=8.6, 2H), 7.22 (d, J=0.8 Hz, 1H), 5.07 (dd, J=10.5, 8.9 Hz, 1H), 3.91-3.77 (m, 2H), 3.05 (hept, J=7.0 Hz, 1H), 2.90-2.82 (m, 1H), 2.52 (s, 3H), 2.42-2.31 (m, 1H), 1.24 (d, J=3.2 Hz, 3H), 1.23 (d, J=3.2 Hz, 3H); MS: (ES) m/z calculated for C$_{21}$H$_{22}$ClF$_3$N$_5$O [M+H]$^+$452.1, found 451.9. The titled compounds were analyzed by chiral normal phase chromatography (Regis Cell cat #784104, 25 cm×4.6 mm, 5 micron; eluent: 0.1% diethylamine/IPA, 0.6 ml/min). The (S)-enantiomer generated from the first-eluting diasteromer from step b had a retention time of 6.8 min (isolated in 8:1 er). The (R)-enantiomer generated from the second-eluting diasteromer from step b had a retention time of 7.3 min (isolated in 78:1 er).

Example 43

Synthesis of (3S)-1-[1-(4-chlorophenyl)-5-isopropyl-triazol-4-yl]-3-[2-methyl-4-(trifluoromethyl)imidazol-1-yl]pyrrolidin-2-one and (3R)-1-[1-(4-chlorophenyl)-5-isopropyl-triazol-4-yl]-3-[2-methyl-4-(trifluoromethyl)imidazol-1-yl]pyrrolidin-2-one

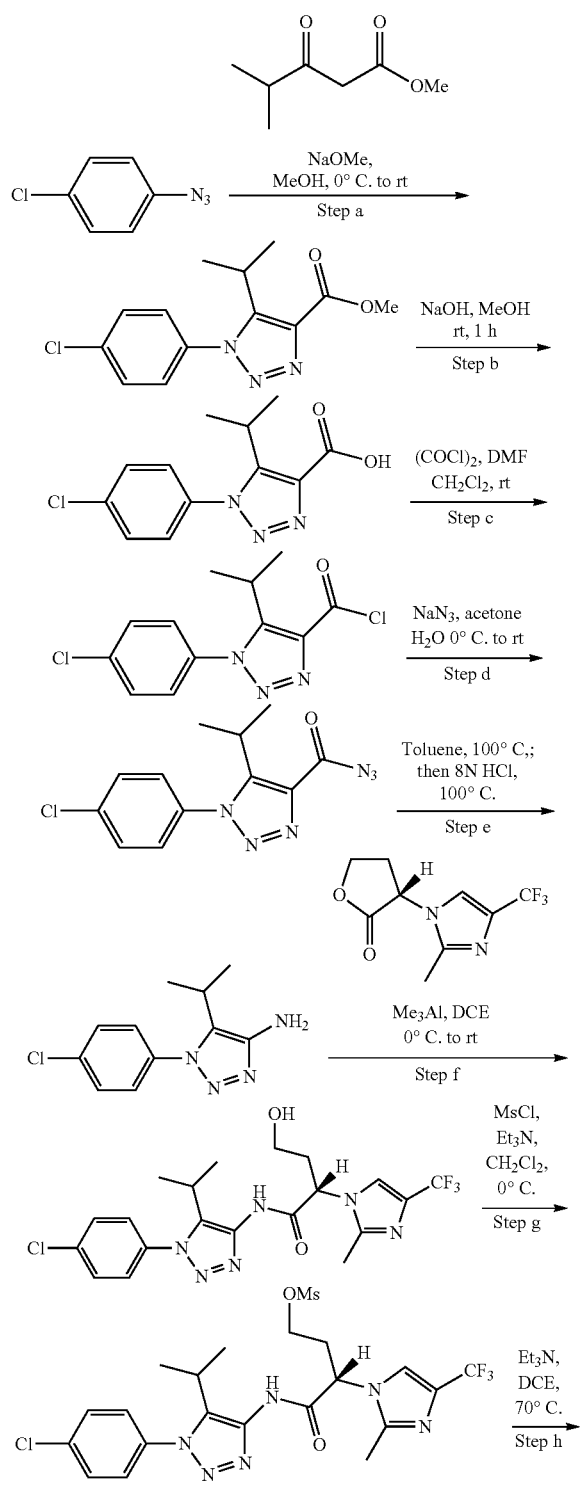

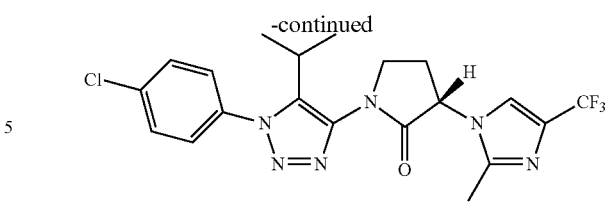

a) To a cooled (0° C.) solution of methyl 4-methyl-3-oxopentanoate (1.72 g, 12 mmol) in MeOH (10 mL) under $N_2$ atmosphere was added NaOMe (2.6 g of the 25 wt % solution in MeOH, 12 mmol) and 1-azido-4-chloro-benzene (0.5 M in MTBE, 20 mL, 10 mmol). The mixture was stirred at room temperature overnight, and MTBE was removed in vacuo to give the crude ester.

b) To the crude ester was added MeOH (5 mL) and 5 N NaOH (5 mL) at room temperature and the resulting reaction mixture was stirred for an hour. After removing MeOH in vacuo, the aqueous residue was cooled in an ice-bath and 12 N aqueous HCl was slowly added until pH 2 at which point a yellow solid was formed. The yellow solid was then collected by filtration and dissolved in EtOAc (50 mL). EtOAc was then slowly removed in vacuo and towards the end, a white free flowing solid started to form. At this point, it was diluted with $Et_2O$ (100 mL) to further precipitate the white crystalline solid which was collected by filtration to afford 1-(4-chlorophenyl)-5-isopropyl-triazole-4-carboxylic acid (830 mg, 3.13 mmol, 31% yield).

c) To a cooled (0° C.) solution of 1-(4-chlorophenyl)-5-isopropyl-triazole-4-carboxylic acid (830 mg, 3.13 mmol) in dichloromethane (3 mL) was added DMF (50 μL) followed by oxalyl chloride (546 μL, 6.26 mmol) dropwise. After 5 min, the ice bath was removed and the mixture was stirred at room temperature for 1 h. $CH_2Cl_2$ was removed in vacuo to give 1-(4-chlorophenyl)-5-isopropyl-triazole-4-carbonyl chloride as a white solid which was used in the next step without further purification.

d) Sodium azide (610 mg in 2.5 mL of $H_2O$, 9.39 mmol) was added to a cooled (0° C.) solution of 1-(4-chlorophenyl)-5-isopropyl-triazole-4-carbonyl chloride in acetone (7.5 mL). The resulting mixture was stirred at room temperature for 30 min, diluted with $CH_2Cl_2$ (100 mL), washed with water (50 mL) and brine (50 mL), dried ($MgSO_4$), and concentrated in vacuo to give the crude 1-(4-chlorophenyl)-5-isopropyl-triazole-4-carbonyl azide (777 mg) which was used in the next step without further purification.

e) A solution of 1-(4-chlorophenyl)-5-isopropyl-triazole-4-carbonyl azide (777 mg, 2.67 mmol) in toluene (12 mL) was stirred at 100° C. for 1.5 h. Aqueous HCl (8 M, 2.5 mL) was then added and the mixture was stirred at 100° C. for 1 h, cooled to room temperature, and diluted with EtOAc (75 mL). Saturated aqueous $NaHCO_3$ solution was then slowly added until pH 8. The organic layer was dried ($MgSO_4$), concentrated in vacuo, and treated with $Et_2O$ (50 mL) to crash out the unwanted 'urea byproduct' which was removed by filtration. The filtrate was concentrated in vacuo to afford 1-(4-chlorophenyl)-5-isopropyl-tiazol-4-amine (497 mg) which was used in the next step without further purification.

f) To a solution of (3S)-3-[2-Methyl-4-(trifluoromethyl)imidazol-1-yl]tetrahydrofuran-2-one (460 mg, 2.1 mmol) and 1-(4-chlorophenyl)-5-isopropyl-tiazol-4-amine (497 mg, 2.1 mmol) in 1,2-dichloroethane (15 mL) at 0° C. was added $Me_3Al$ (2 M in toluene, 1.6 mL, 3.15 mmol). The mixture was then stirred at room temperature overnight, re-cooled to 0° C., quenched with 2 N HCl (3 mL), and neutralized with saturated aqueous $NaHCO_3$ (25 mL).

EtOAc (100 mL) was added and the mixture was gently stirred. The organic layer was collected and washed with brine (50 mL), dried (MgSO₄), and concentrated in vacuo. The obtained crude was purified by automated flash chromatography (SiO₂, 25% MeOH in CH₂Cl₂) to give (2S)—N-[1-(4-chlorophenyl)-5-isopropyl-triazol-4-yl]-4-hydroxy-2-[2-methyl-4-(trifluoromethyl)imidazol-1-yl]butanamide (274 mg, 28% yield).

g) To a cooled (0° C.) solution of (2S)—N-[1-(4-chlorophenyl)-5-isopropyl-triazol-4-yl]-4-hydroxy-2-[2-methyl-4-(trifluoromethyl)imidazol-1-yl]butanamide (274 mg, 0.583 mmol) in dichloromethane (5 mL) was added Et₃N (162 µL, 1.17 mmol) followed by MSCl (60 µL, 0.728 mmol) dropwise. The resulting solution was stirred at <10° C. for 30 min, then diluted with CH₂Cl₂ (50 mL), washed with saturated aqueous NH₄Cl solution (30 mL), dried (MgSO₄), filtered, and concentrated in vacuo to obtain 350 mg of crude [(3S)-4-[[1-(4-chlorophenyl)-5-isopropyl-triazol-4-yl]amino]-3-[2-methyl-4-(trifluoromethyl)imidazol-1-yl]-4-oxo-butyl]methanesulfonate as a yellow foam which was used in the next step without any further purification.

h) [(3S)-4-[[1-(4-chlorophenyl)-5-isopropyl-triaz 4-yl]amino]-3-[2-methyl-4-(trifluoromethyl)imidazol-1-yl]-4-oxo-butyl] methanesulfonate (350 mg, 0.607 mmol) in 1,2-dichloroethane (7 mL) was treated with Et₃N (500 µL, 3.6 mmol) at 70° C. for 3 h. After cooling to room temperature the mixture was directly purified by flash chromatography (SiO₂, EtOAc in CH₂Cl₂) and then by preparative reverse phase HPLC (C18 column, acetonitrile-H₂O with 0.1% TFA as eluent) to obtain (3S)-1-[1-(4-chlorophenyl)-5-isopropyl-triazol-4-yl]-3-[2-methyl-4-(trifluoromethyl)imidazol-1-yl]pyrrolidin-2-one as a white powder as TFA salt (135 mg, 49% yield). ¹H NMR (400 MHz, Methanol-d₄) δ 7.71 (s, 1H), 7.67 (d, 2H, J=8 Hz), 7.55 (d, 2H, J=8 Hz), 5.51 (t, J=19, 9 Hz, 1H), 4.11-3.90 (m, 2H), 3.18-3.02 (m, 1H), 2.92 (dddd, J=12.7, 8.6, 6.7, 1.5 Hz, 1H), 2.74-2.59 (m, 1H), 2.50 (s, 3H), 1.21 (ddd, J=7.0, 2.1, 0.6 Hz, 6H); MS: (ES) m/z calculated for C₂₂H₂₃ClF₃N₅O [M+H]+453.9, found 453.1. The titled compound and its enantiomer were analyzed by chiral normal phase chromatography. Regis Pirkle Covalent (R,R) Whelk-O1 (Catalog 1-786201-300), 25 cm×4.6 mm, 5 micron; eluent: 100% isopropanol, 0.6 mL/min, 13.2 min (R)-isomer and 15.7 min (S)-isomer. The R-enantiomer was prepared in a similar fashion.

Example 44

Synthesis of 1-[1-(4-chlorophenyl)-5-cyclobutyl-pyrazol-4-yl]-3-[2-methyl-4-(trifluoromethyl)imidazol-1-yl]pyrrolidin-2-one

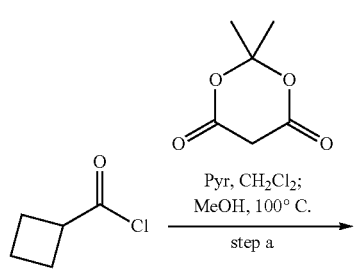

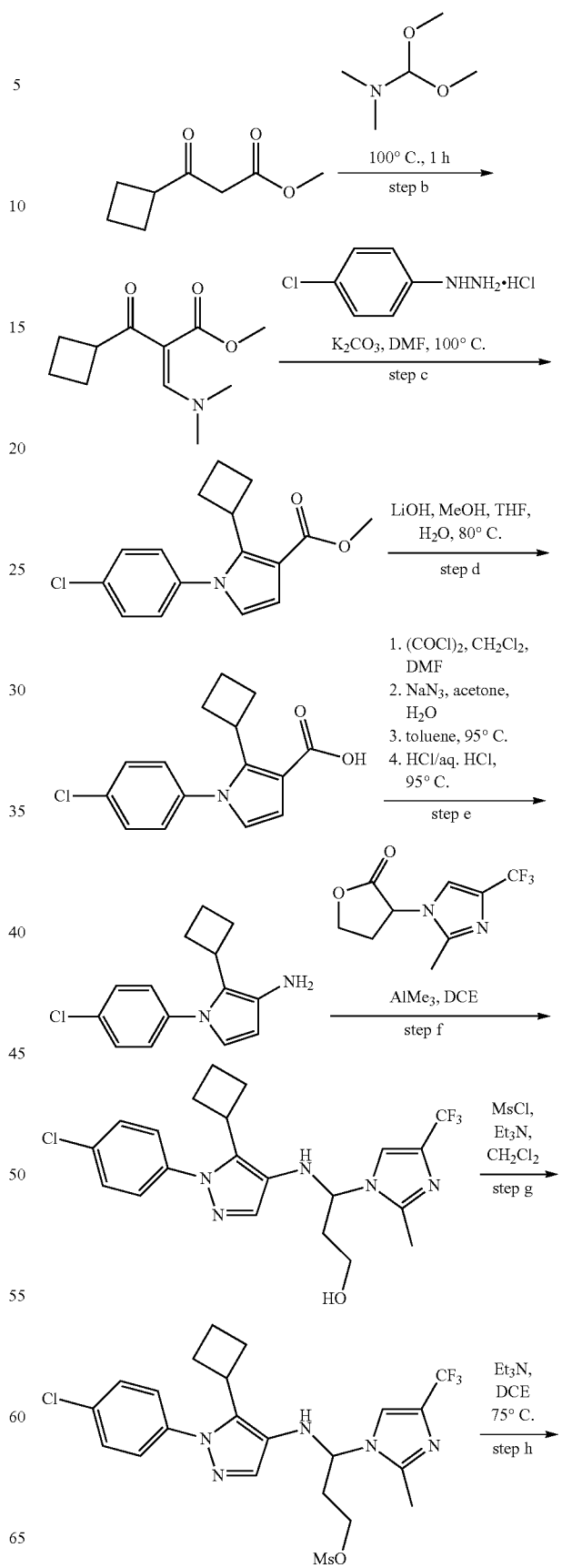

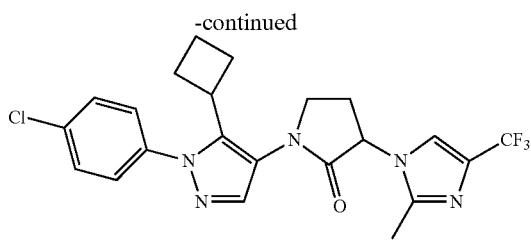

a) Pyridine (20.46 mL, 253 mmol) was added to a solution of cyclobutanecarboxylic acid chloride (10.0 g, 84.3 mmol) and isopropylidene malonate (12.16 g, 84.3 mmol) in CH$_2$Cl$_2$ (100 mL) at 0° C. and the mixture was stirred at room temperature for 1.5 h. Methanol (100 mL) was then added and the resulting mixture was stirred at reflux for 3 h, cooled to room temperature, and partitioned between aqueous HCl (1 M, 200 mL) and EtOAc (500 mL). The organic layer was separated, dried over anhydrous sodium sulfate, concentrated in vacuo, and purified by flash chromatography (SiO$_2$, 0-20% EtOAc/hexanes gradient elution) to give methyl 3-cyclobutyl-3-oxo-propanoate (11.6 g, 88% yield).

b) A mixture of methyl 3-cyclobutyl-3-oxo-propanoate (5.8 g, 37.2 mmol) and N,N-dimethylformamide dimethyl acetal (25 g, 210 mmol) was stirred at 100° C. for 1 h. After cooling to room temperature, the mixture was concentrated in vacuo to give an oily residue that was directly carried to the next step.

c) A mixture of the intermediate (~37.2 mmol) obtained in step b, 4-chlorophenylhydrazine hydrochloride (6.67 g, 37.2 mmol) and K$_2$CO$_3$ (10.3 g, 74.4 mmol) in DMF (50 mL) was stirred at 100° C. for 1 h. After cooling to room temperature the mixture was diluted with aqueous HCl (200 mL) and extracted with EtOAc (500 mL). The organic layer was separated, dried over anhydrous sodium sulfate, concentrated in vacuo, and purified by flash chromatography (SiO$_2$, 0-10% EtOAc/CH$_2$Cl$_2$ gradient elution) to give methyl 1-(4-chlorophenyl)-5-cyclobutyl-pyrazole-4-carboxylate (8.3 g, 76% yield).

d) A mixture of methyl 1-(4-chlorophenyl)-5-cyclobutyl-pyrazole-4-carboxylate (8.3 g, 28.5 mmol) and lithium hydroxide monohydrate (3.6 g, 85.6 mmol) in MeOH (25 mL), THF (25 mL) and H$_2$O (12 mL) was stirred at 80° C. for 1 h. After cooling to room temperature the mixture was acidified with 1 M aqueous HCl and extracted with EtOAc (400 mL). The organic layer was separated, dried over anhydrous sodium sulfate, and concentrated in vacuo to yield 1-(4-chlorophenyl)-5-cyclobutyl-pyrazole-4-carboxylic acid (6.92 g, 87% yield).

e) To a mixture of 1-(4-chlorophenyl)-5-cyclobutyl-pyrazole-4-carboxylic acid (4.0 g, 14.4 mmol) in CH$_2$Cl$_2$ (100 mL) was added oxalyl chloride (3.78 mL, 43.4 mmol) and DMF (0.06 mL). After 2 h at room temperature, the reaction mixture was concentrated in vacuo, re-dissolved in 40 mL of acetone, and added to a 0° C. solution of NaN$_3$ (3.75 g, 57.8 mmol) in H$_2$O (40 mL). Brine (150 mL) and EtOAc (350 mL) were then added. The organic layer was separated, dried over anhydrous sodium sulfate, and concentrated in vacuo. The residue was stirred in 100 mL of toluene at 95° C. for 1 h, cooled to room temperature, and then treated with 150 mL of 6 M aqueous HCl at 110° C. for 1 h. After cooling to room temperature, the mixture was basified with dilute NH$_4$OH and extracted with EtOAc (500 mL). The organic layer was separated, dried over anhydrous sodium sulfate, concentrated in vacuo, and purified by flash chromatography (SiO$_2$, 0-100% EtOAc/CH$_2$Cl$_2$ gradient elution) to yield 1-(4-chlorophenyl)-5-cylocbutyl-pyrazol-4-amine (2.9 g, 81% yield).

f) A mixture of 1-(4-chlorophenyl)-5-cylocbutyl-pyrazol-4-amine (0.080 g, 0.32 mmol) and 3-[2-methyl-4-(trifluoromethyl)imidazol-1-yl]tetrahydrofuran-2-one (0.080 g, 0.34 mmol) in 1,2-dichloroethane (2 mL) was treated with Me$_3$Al (0.32 mL, 0.64 mmol, 2 M/toluene) at room temperature for 1.5 h. The reaction mixture was then quenched with saturated aqueous NaHCO$_3$ solution and extracted with EtOAc (100 mL). The organic layer was separated, dried over anhydrous sodium sulfate, and concentrated in vacuo to obtain the desired alcohol intermediate.

g) A 0° C. solution of the alcohol intermediate (~0.32 mmol) obtained in step f and Et$_3$N (0.067 mL, 0.48 mmol) in CH$_2$Cl$_2$ (1.5 mL) was treated with methanesulfonyl chloride (0.027 mL, 0.35 mmol) for 10 min. The mixture was then basified with saturated aqueous NaHCO$_3$ solution and extracted with EtOAc (500 mL). The organic layer was separated, dried over anhydrous sodium sulfate and concentrated in vacuo to afford the desired mesylate.

h) A mixture of the mesylate (~0.032 mmol) obtained in step g and Et$_3$N (0.15 mL, 1.07 mmol in 1,2-dichloroethane (3 mL) was stirred at 75° C. for 3 h. After cooling to room temperature the reaction mixture was directly purified by flash chromatography (SiO$_2$, 0-100% EtOAc/CH$_2$Cl$_2$), followed by reverse phase HPLC (C18 column, acetonitrile-H$_2$O with 0.1% TFA as eluent) to afford the titled compound (0.060 g, 40% yield, free form). $^1$H NMR (400 MHz, CDCl$_3$) δ 7.57 (s, 1H), 7.43 (m, 2H), 7.36 (m, 2H), 7.23 (d, J=1.2 Hz, 1H), 4.95 (dd, J=9.2, 8.4 Hz, 1H), 3.86 (m, 2H), 3.71 (m, 1H), 2.84 (m, 1H), 2.50 (s, 3H), 2.36 (m, 1H), 1.99 (m, 6H); MS: (ES) m/z calculated for C$_{22}$H$_{21}$ClF$_3$N$_5$O [M+H]$^+$ 464.1, found 464.1.

Example 45

Synthesis of (3S)-1-[1-(4-chloro-3-methoxy-phenyl)-5-isopropyl-pyrazol-4-yl]-3-[2-methyl-4-(trifluoromethyl)imidazol-1-yl]pyrrolidin-2-one

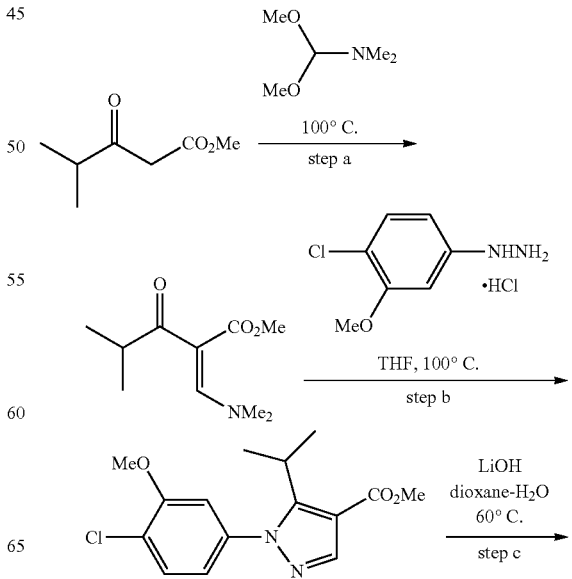

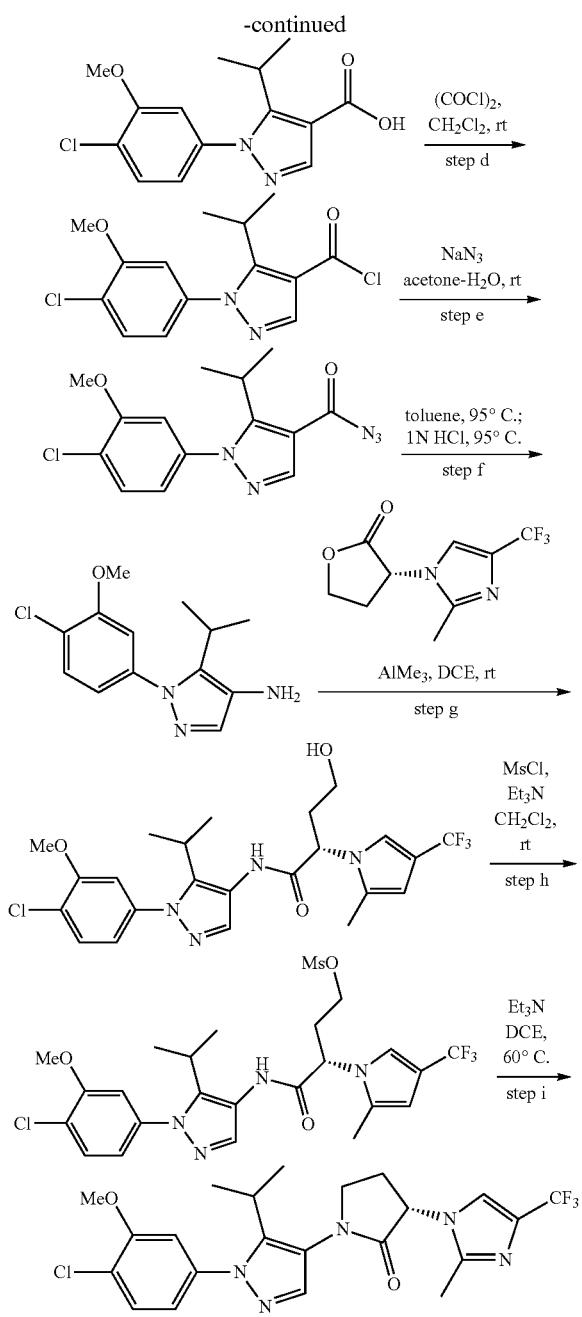

a) A mixture of methyl 4-methyl-3-oxo-pentanoate (1.98 g, 13.7 mmol) and N,N-dimethylformamide dimethyl acetal (1.95 g, 16.4 mmol) was stireed at 100° C. for 1 d. After cooling to room temperature, the reaction mixture was concentrated in vacuo to remove volatiles and the crude material carried out directly to the next step.

b) A solution of 4-chloro-3-methoxyphenylhydrazine hydrochloride (3.0 g, 14.4 mmol) and methyl (2Z)-2-(dimethylaminomethylene)-4-methyl-3-oxo-pentanoate (assumed 13.7 mmol) from step a in DMF (15 mL) was stirred at 100° C. for 8 h. After cooling to room temperature, the mixture was treated with ice (10 g) and stirred for 5 h. The mixture was filtered and washed with water (15 mL). The solid was collected, dried on high vacuum pump, and carried directly to the next step.

c) A biphasic solution of methyl 1-(4-chloro-3-methoxy-phenyl)-5-isopropyl-pyrazole-4-carboxylate from step b (assumed 13.7 mmol) and lithium hydroxide monohydrate (1.2 g, 22.6 mmol) in tetrahydrofuran (20 mL) and water (16 mL) was heated at 60° C. with stirring for 1.5 h. After cooling, the mixture was evaporated and diluted with 1 N HCl and extracted with EtOAc (2×60 mL). The organic layer was dried over MgSO₄, filtered, and concentrated in vacuo. The crude brown solid was triturated with a mixture of chloroform and hexane (1:4) to afford the product (2.83 g, 9.60 mmol, 70% yield) as a white solid.

d) To a solution of methyl 1-(4-chloro-3-methoxy-phenyl)-5-isopropyl-pyrazole-4-carboxylic acid (0.8 g, 2.71 mmol) from step c in dichloromethane (8.0 mL) was added oxalyl choride (0.27 mL) and 5 drops of DMF. The mixture was stirred for 3 h and concentrated in vacuo. The crude material was dried under high vacuum for several hours before it was used in the next step.

e) To a solution of methyl 1-(4-chloro-3-methoxy-phenyl)-5-isopropyl-pyrazole-4-carbonyl chloride (assumed 2.71 mmol) from step d in acetone (7 mL) was rapidly added a solution of sodium azide (0.50 g, 7.7 mmol) in water (3 mL). The mixture was stirred vigorously for 1 h at room temperature. Dichloromethane (12 mL) was added in and the layers were separated. The organic layer was washed with brine, dried over sodium sulfate, concentrated, and used without further purification.

f) A solution of the acyl azide intermediate (assumed 2.71 mmol) from step e in toluene (20 mL) was heated at 95° C. for 30 min before 1 N HCl (5 mL) was added and the biphasic mixture was heated at 95° C. overnight. After cooling, the mixture was treated with sodium hydroxide solution (2 N) and extracted with chloroform (2×20 mL). The combined organic layers were dried over MgSO₄, filtered, and concentrated in vacuo. Purification of the crude material by flash chromatography (SiO₂, 5% MeOH/CH₂Cl₂) afforded the product (504 mg, 1.90 mmol, 70% yield) as a light brown solid.

g) Trimethylaluminum (0.16 mL, 2 M in toluene, 0.32 mmol) was slowly added under nitrogen to a solution of the 1-(4-chloro-3-methoxy-phenyl)-5-isopropyl-pyrazol-4-amine (57 mg, 0.21 mmol) and (3R)-3-[2-methyl-4-(trifluoromethyl)imidazol-1-yl]tetrahydrofuran-2-one (50 mg, 0.21 mmol) in 1,2-dichloroethane (2 mL) at room temperature. The mixture was allowed to stir for 30 min. The reaction was carefully quenched by adding a few drops of 1 N HCl. After bubbling subsided, the thick mixture was diluted with more 1 N HCl and extracted with CH₂Cl₂ (2×20 mL). The combined organic extracts were dried over MgSO₄, filtered, and concentrated in vacuo. The crude material was carried to the next step without further purification.

h) To a solution of the crude alcohol intermediate (assumed 0.21 mmol) from step g and triethylamine (0.10 mL, 0.63 mmol) in dichloromethane (3 mL) was slowly added methanesulfonyl chloride (0.025 mL, 0.32 mmol). The reaction mixture was allowed to stir at room temperature for 15 min before it was diluted with dichloromethane and washed with water. The organic layer was separated, dried over MgSO₄, filtered, and concentrated in vacuo. The crude material was carried to the next step without further purification.

i) To the crude mesylate intermediate from step h (assumed 0.21 mmol) in 1,2-dichloroethane (2 mL) was added triethylamine (0.059 mL, 0.42 mmol). After stirring at 60° C. for 2 h, the reaction was quenched by the addition of saturated aqueous sodium bicarbonate and extracted with CH₂Cl₂ (2×20 mL). The organic layers were combined, dried over MgSO₄, filtered, and concentrated in vacuo. The crude residue was purified by reverse phase HPLC (C18 column, acetonitrile-$H_2O$ with 0.1% TFA as eluent) to afford the titled compound (20 mg, 0.042 mmol, 20% yield over three steps) as a white solid. $^1$H NMR (400 MHz, $CDCl_3$) δ 7.63 (d, J=0.6 Hz, 1H), 7.49 (d, J=8.3 Hz, 1H), 7.29 (s, 1H), 7.02-6.90 (m, 2H), 5.06 (dd, J=9.1, 6.0 Hz, 1H), 3.98-3.79 (m, 5H), 3.08 (dt, J=14.1, 7.4 Hz, 1H), 2.93 (dt, J=14.3, 7.5 Hz, 1H), 2.63 (s, 3H), 2.47-2.35 (m, 1H), 1.25 (dd, J=7.1, 2.7 Hz, 6H); MS: (ES) m/z calculated for $C_{22}H_{23}ClF_3N_5O_2$ [M+H]$^+$482.1, found 481.9.

Example 46

This example illustrates the evaluation of the biological activity associated with compounds of interest of the invention.

Materials and Methods

A. Cells

1. CCR1 Expressing Cells a) THP-1 Cells

THP-1 cells were obtained from ATCC (TIB-202) and cultured as a suspension in RPMI-1640 medium supplemented with 2 mM L-glutamine, 1.5 g/L sodium bicarbonate, 4.5 g/L glucose, 10 mM HEPES, 1 mM sodium pyruvate, 0.05% 2-mercaptoethanol and 10% FBS. Cells were grown under 5% $CO_2$/95% air, 100% humidity at 37° C. and subcultured twice weekly at 1:5 (cells were cultured at a density range of $2\times10^5$ to $2\times10^6$ cells/mL) and harvested at $1\times10^6$ cells/mL. THP-1 cells express CCR1 and can be used in CCR1 binding and functional assays.

2. Chemotaxis Assays

Chemotaxis assays were performed using 5 μm pore polycarbonate, polyvinylpyrrolidone-coated filters in 96-well chemotaxis chambers (Neuroprobe; Gaithersburg, Md.) using chemotaxis buffer (Hank's balanced salt solution (HBSS) and 1% FBS). CCR1 chemokine ligands (i.e., MIP-1α, CCL15/Leukotactin; R&D Systems; Minneapolis, Minn.) are use to evaluate compound mediated inhibition of CCR1 mediated migration. Other chemokines (i.e., SDF-1α; R&D Systems; Minneapolis, Minn.) are used as specificity controls. The lower chamber was loaded with 29 μl of chemokine (i.e., 0.1 nM CCL15/Leukotactin) and varying amounts of compound; the top chamber contained 100,000 THP-1 or monocyte cells in 20 μl. The chambers were incubated 1-2 hours at 37° C., and the number of cells in the lower chamber quantified either by direct cell counts in five high powered fields per well or by the CyQuant assay (Molecular Probes), a fluorescent dye method that measures nucleic acid content and microscopic observation.

B. Identification of Inhibitors of CCR1

One of the primary functions of chemokines is their ability to mediate the migration of chemokine receptor-expressing cells, such as white blood cells. To confirm that a compound of interest inhibited not only CCR1 specific binding and signaling (at least as determined by calcium mobilization assays), but also CCR1 mediated migration, a chemotaxis assay was employed. THP-1 myelomonocytic leukemia cells, which resemble monocytes, as wells as freshly isolated monocytes, were used as targets for chemoattraction by CCR1 chemokine ligands (i.e., MIP-1α, CCL15/leukotactin). Cells were placed in the top compartment of a microwell migration chamber, while MIP-1α (or other potent CCR1 chemokine ligand) and increasing concentrations of a compound of interest was loaded in the lower chamber. In the absence of inhibitor, cells will migrate to the lower chamber in response to the chemokine agonist; if a compound inhibited CCR1 function, then the majority of cells will remain in the upper chamber. To ascertain a compound of interest's affinity for CCR1 as well as to confirm its ability to inhibit CCR1 mediated cell migration, inhibitory activity was titered over a $1\times10^{-10}$ to $1\times10^{-4}$ M range of compound concentrations in this chemotaxis assay. In this assay, the amount of compound was varied; while cell number and chemokine agonist concentrations were held constant. After the chemotaxis chambers were incubated 1-2 hours at 37° C., the responding cells in the lower chamber were quantified by labeling with the CyQuant assay (Molecular Probes), a fluorescent dye method that measures nucleic acid content, and by measuring with a Spectrafluor Plus (Tecan). The computer program Prism from GraphPad, Inc. (San Diego, Calif.) was used to calculate $IC_{50}$ values. $IC_{50}$ values are those compound concentrations required to inhibit the number of cells responding to a CCR1 agonist by 50%.

1. In Vivo Efficacy a) Rabbit Model of Destructive Joint Inflammation

A rabbit LPS study was conducted essentially as described in Podolin, et al. *J. Immunol.* 169(11):6435-6444 (2002). Female New Zealand rabbits (approximately 2 kilograms) were treated intra-articularly in both knees with LPS (10 ng). The compound of interest, for example 1.016, (formulated in 1% methocel) or vehicle (1% methocel) was dosed orally at a 5 ml/kg dose volume at two times (2 hours before the intra-articular LP S injection and 4 hours after the intra-articular LP S injection). Sixteen hours after the LP S injection, knees were lavaged and cells counts were performed. Beneficial effects of treatment were determined by reduction in the number of inflammatory cells recruited to the inflamed synovial fluid of the knee joints. Treatment with the compound of interest resulted in a significant reduction in recruited inflammatory cells.

b) Evaluation of a Compound of Interest in a Rat Model of Collagen Induced Arthritis A 17 day developing type II collagen arthritis study is conducted to evaluate the effects of a compound of interest on arthritis induced clinical ankle swelling. Rat collagen arthritis is an experimental model of polyarthritis that has been widely used for preclinical testing of numerous anti-arthritic agents (see Trentham, et al., *J. Exp. Med.* 146(3): 857-868 (1977), Bendele, et al., *Toxicologic Pathol.* 27:134-142 (1999), Bendele, et al., *Arthritis Rheum.* 42:498-506 (1999)). The hallmarks of this model are reliable onset and progression of robust, easily measurable polyarticular inflammation, marked cartilage destruction in association with pannus formation and mild to moderate bone resorption and periosteal bone proliferation.

Female Lewis rats (approximately 0.2 kilograms) are anesthetized with isoflurane and injected with Freund's Incomplete Adjuvant containing 2 mg/mL bovine type II collagen at the base of the tail and two sites on the back on days 0 and 6 of this 17 day study. A compound of interest is dosed daily in a sub-cutaneous manner from day 0 till day 17 at a efficacious dose. Caliper measurements of the ankle joint diameter are taken, and reduced joint swelling is taken as a measure of efficacy.

Murine Model of Dermatological Disease

Compounds of the invention can be assessed in the murine model of dermal delayed type hypersensitivity induced by oxazolone. Briefly, 8-10 week old BALB/c mice are sensitized topically with a 1% solution of oxazolone dissolved in ethanol on their shaved abdomens on day 0. On day 6 post sensitization mice are dosed orally with either vehicle or increasing doses of a compound of the invention immediately prior to and 4 hours following a topical challenge with a 0.5% solution of oxazolone in ethanol on the right ear. The following day (day 7), ear thicknesses are measured using caliper measurements. Animals treated with compound have significantly reduced ear swelling compared to vehicle treated controls indicating a compound mediated decrease in oxazolone induced dermal hypersensitivity.

Murine Asthma Model

Compounds of the invention can be assessed in the murine model of allergic asthma. Asthma is induced in 8-10 week old BALB/c mice by sensitizing mice with OVA in Alum adjuvant on days 0 and 10. On day 20 mice are challenged with OVA in PBS intranasally to elicit airway inflammation. Groups of mice are either treated with vehicle, or increasing doses of a compound of the invention starting on day 20 and lasting until day 23. Animals are analyzed at day 23 after the intranasal OVA challenge for cellular infiltrates in bronchoalveolar lavage (BAL). A significant reduction in BAL leukocyte numbers relative to vehicle treated mice indicates the compound is effective in this model.

Murine Model of Systemic Lupus Erythematosus

This example describes a procedure to evaluate efficacy of CCR1 antagonists for treatment of Systemic Lupus Erythematosus (SLE). Female NZB/W FI mice spontaneously develop an SLE-like pathology commencing at 6 months of age that is characterized by proteinuria, serum autoantibodies, glomerulonephritis, and eventually death. Three series of NZB/W FI mouse groups comprising 20 mice per group are tested for efficacy of CCR1 antagonist as follows: One series of mice additionally receives phosphate buffered saline (PBS) and Tween 0.5% i.p. soon after weaning, and thereafter at varying dosing schedules. A second series consists of groups of mice receiving different doses of the CCR1 antagonist given either intra-peritoneally, intra-venously, sub-cutaneously, intramuscularly, orally, or via any other mode of administration soon after weaning, and thereafter at varying dosing schedules. A third series of mice, serving as positive control, consists of groups treated with anti-IL10 antibodies given soon after weaning, and thereafter at varying dosing schedules. Disease development is monitored in terms of eventual mortality, kidney histology, serum autoantibody levels, and proteinuria.

Murine Model of Cancer

This example describes a procedure to evaluate efficacy of CCR1 antagonists for treatment of malignancy. Normal mouse strains can be transplanted with a variety of well-characterized mouse tumor lines, including a mouse thymoma EL4 which has been transfected with OVA to allow easy evaluation of tumor specific antigen responses following vaccination with OVA. Three series of mouse groups from any of these tumor models are tested for CCR1 antagonist efficacy as follows: One series of mice additionally receives PBS and Tween 0.5% i.p. soon after tumor transplant, and thereafter at varying dosing schedules. A second series consists of groups of mice receiving different doses of the CCR1 antagonist given either intra-peritoneally, intra-venously, sub-cutaneously, intramuscularly, orally, or via any other mode of administration soon after tumor transplant, and thereafter at varying dosing schedules. A third series of mice, serving as positive control, consists of groups treated with either anti-IL4 antibodies, anti-IFNg antibodies, IL4, or TNF, given i.p. soon after tumor transplant, and thereafter at varying dosing schedules. Efficacy is monitored via tumor growth versus regression. In the case of the OVA-transfected EL4 thymoma model, cytolytic OVA-specific responses can be measured by stimulating draining lymph node cells with OVA in vitro, and measuring antigen-specific cytotoxicity at 72 hours.

Murine Model of Psoriasis

This example describes procedures to evaluate the efficacy of CCR1 antagonists in psoriasis. A rodent model of psoriasis can be obtained by intra-venously transferring a population of purified T cells (designated CD45Rbhi T cells) obtained from the spleens of BALB/c mice into immunodeficient recipient CB.17 scid/scid mice. Mice develop signs of redness, swelling, and skin lesions resembling those of human psoriasis in their ear, feet and tail by 8 weeks after transfer. Three series of mouse groups, comprising 10-15 CB.17 scid/scid mice per group, are injected with purified CD45Rbhi T cells. One series of mice additionally receives phosphate buffered saline (PBS) and Tween 0.5% i.p. at the initial cell transfer, and at different dosing schedules thereafter. A second series consists of groups of mice receiving different doses of the CCR1 antagonist given either intra-peritoneally, intra-venously, sub-cutaneously, intra-muscularly, orally, or via any other mode of administration at the initial cell transfer, and at different dosing schedules thereafter. A third series of mice, serving as positive control, consists of groups treated with antibodies to either IL-12, IL-4, IFNg, or TNF, or with cytokine IL-10 at the initial cell transfer, and at different dosing schedules thereafter. Animals are monitored for development of psoriatic-like lesions for 3 months after cell transfer.

Murine Model of Inflammatory Bowel Diseases

The MDR1a-knockout mice, which lack the P-glycoprotein gene, spontaneously develop colitis under specific pathogen-free condition. The pathology in these animals has been characterized as Th1-type T cell-mediated inflammation similar to ulcerative colitis in humans. Disease normally begins to develop at around 8-10 weeks after birth. However the ages at which disease emerges and the ultimate penetrance level often vary considerably among different animal facilities. In a study using the MDR1a-knockout mice, a CCR1 antagonist can be evaluated prophylacticly or therapeutically depending on time of administration. Female mice (n=34) are dosed with a compound of interest as appropriate to the compound eg daily in a sub-cutaneous manner at a efficacious dose. The study is evaluated for IBD associated growth retardation and scoring of anal discharge and irritation. A compound which reduces anal discharge and irritation or inhibits IBD associated growth retardation indicates efficacy of compound in this indication.

Murine Model of Solid Tumors

The mouse RENCA tumor model accurately mimics the progression of human adult renal cell carcinoma specifically with reference to spontaneous metastasis to lungs and serves as a model for solid tumors. Balb/c 6-8 week old female mice are inoculated with approximately 5e5 RENCA cells (mouse renal adenocarcinoma; ATCC cat #CRL-2947) under the kidney capsule and kidney tumor growth is observed over 22 days, with lung metastasis observed as early as day 15. Animals are dosed with either vehicle or a compound of the invention eg daily subcutaneously, from the time of tumor implantation to monitor effects on primary growth, or at a later time (eg day 7) to monitor the compound effect on metastasis. Primary tumor areas are measured twice a week using mechanical calipers. Tumor volumes are calculated by the formula $v=pab2/6$, where a is the longest diameter and b is the next longest diameter perpendicular to a. A reduction in tumor volume or incidence of metastasis indicates efficacy of compound in this indication.

Murine Model of Inflammation

A method of inducing peritoneal inflammation by the introduction of 3% thioglycolate into the peritoneum is well know in the art. Following the introduction of thioglycolate, a rapid influx of immune cells to the site, primarily CCR1 bearing neutrophils, results in local inflammation at 24 hours. A peritoneal exudate can be sampled, and the cell number and composition can be assessed to determine the anti-inflammatory properties of a compound of interest administered before, during or after the thioglycolate induction. When employed in this assay, compound 1.042 of the invention resulted in a dramatic decrease in total cell and neutrophil number demonstrating both efficacy and biological coverage of the target receptor.

In Table 2 (below), structures and activity are provided for representative compounds described herein. Activity is provided as follows for the chemotaxis assay as described above: +, 20 µM>$IC_{50}$>100 nM; ++, $IC_{50}$≤100 nM.

TABLE 2

| Structure | Avg Mig IC50 (nM) | Compound number |
|---|---|---|
| 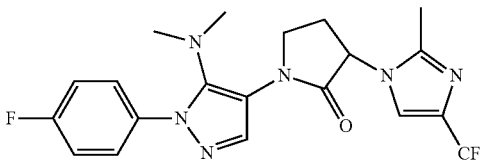 | + | 1.001 |
| 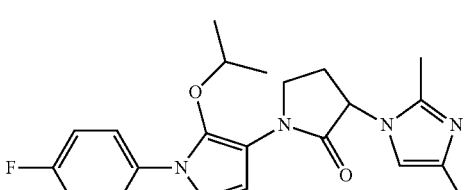 | ++ | 1.002 |
| 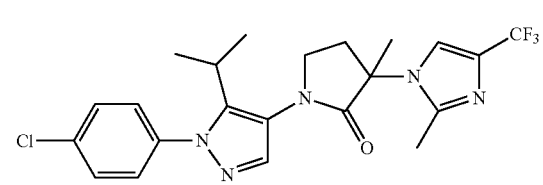 [SMILES: Cc1nc(C(F)(F)F)cn1C1(C)CCN(c2cnn(-c3ccc(Cl)cc3)c2C(C)C)C1=O] | + | 1.003 |
| 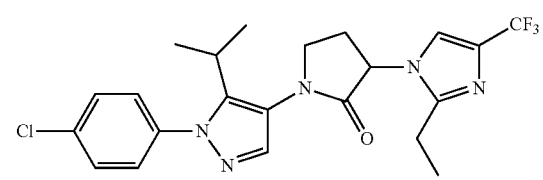 [SMILES: CCc1nc(C(F)(F)F)cn1C1CCN(c2cnn(-c3ccc(Cl)cc3)c2C(C)C)C1=O] | ++ | 1.004 |
| 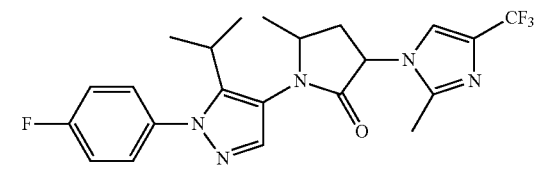 [SMILES: Cc1nc(C(F)(F)F)cn1C1CC(C)N(c2cnn(-c3ccc(F)cc3)c2C(C)C)C1=O] | + | 1.005 |
| 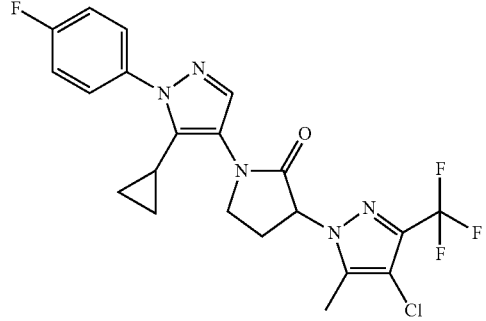 [SMILES: Cc1c(Cl)c(C(F)(F)F)nn1C1CCN(c2cnn(-c3ccc(F)cc3)c2C2CC2)C1=O] | ++ | 1.006 |

TABLE 2-continued

| Structure | Avg Mig IC50 (nM) | Compound number |
|---|---|---|
| (structure) | + | 1.007 |
| (structure) | ++ | 1.008 |
| (structure) | ++ | 1.009 |
| (structure) | ++ | 1.010 |
| (structure) | ++ | 1.011 |
| (structure) | + | 1.012 |

TABLE 2-continued
| | Avg Mig IC50 (nM) Compound number |
|---|---|
|  | + 1.013 |
|  | + 1.014 |
| 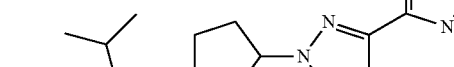 | + 1.015 |
| 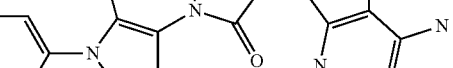 | + 1.016 |
|  | + 1.017 |
| 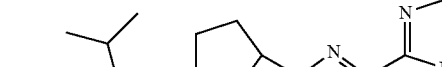 | + 1.018 |
| 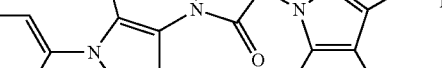 | + 1.019 |

TABLE 2-continued

| Structure | Avg Mig IC50 (nM) | Compound number |
|---|---|---|
| | + | 1.020 |
| | + | 1.021 |
| | ++ | 1.022 |
| | + | 1.023 |
| | + | 1.024 |
| | ++ | 1.025 |

TABLE 2-continued

| | Avg Mig IC50 (nM) Compound number |
|---|---|
| [structure] | + 1.026 |
| [structure] | + 1.027 |
| [structure] | ++ 1.028 |
| [structure] | + 1.029 |
| [structure] | + 1.030 |

TABLE 2-continued
| | Avg Mig IC50 (nM) Compound number |
|---|---|
| 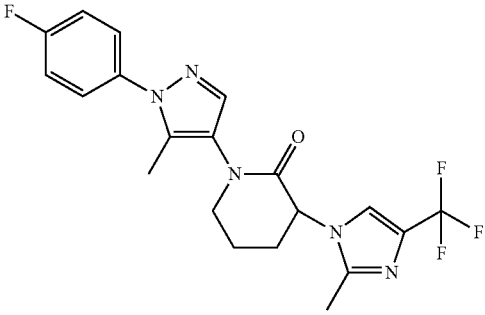 [SMILES: Cc1nc(C(F)(F)F)cn1C1CCCN(c2cnn(-c3ccc(F)cc3)c2C)C1=O] | + 1.031 |
| 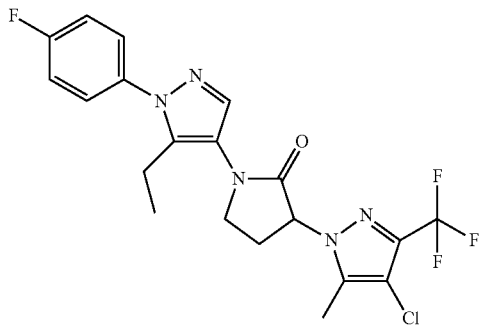 [SMILES: CCc1c(N2CCC(n3nc(C(F)(F)F)c(Cl)c3C)C2=O)cnn1-c1ccc(F)cc1] | ++ 1.032 |
| 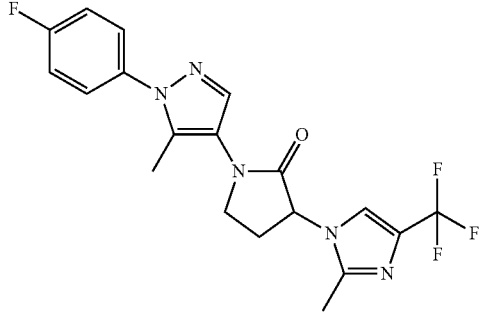 [SMILES: Cc1nc(C(F)(F)F)cn1C1CCN(c2cnn(-c3ccc(F)cc3)c2C)C1=O] | + 1.033 |
| 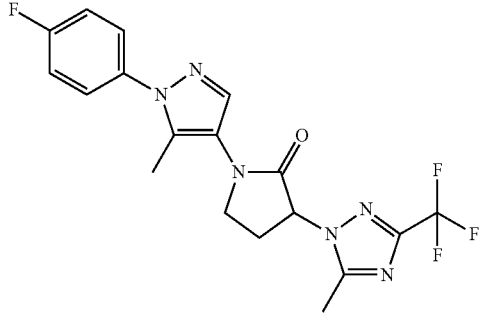 [SMILES: Cc1c(N2CCC(n3nc(C(F)(F)F)nc3C)C2=O)cnn1-c1ccc(F)cc1] | + 1.034 |

TABLE 2-continued

| Structure | Compound number | Avg Mig IC50 (nM) |
|---|---|---|
| (structure) | 1.035 | + |
| (structure) | 1.036 | + |
| (structure) | 1.037 | + |
| (structure) | 1.038 | + |

TABLE 2-continued
| | Avg Mig IC50 (nM) Compound number |
|---|---|
| 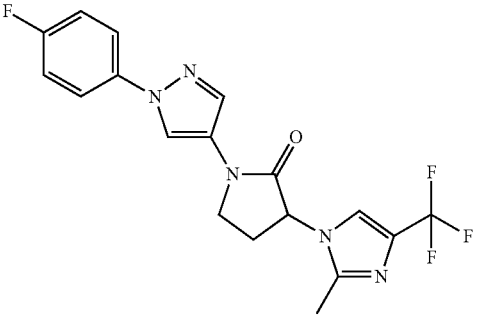 [SMILES: Cc1nc(C(F)(F)F)cn1C1CCN(c2cnn(-c3ccc(F)cc3)c2)C1=O] | + 1.039 |
| 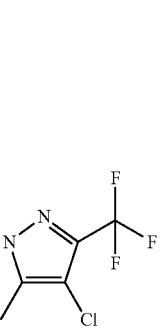 | + 1.040 |
| 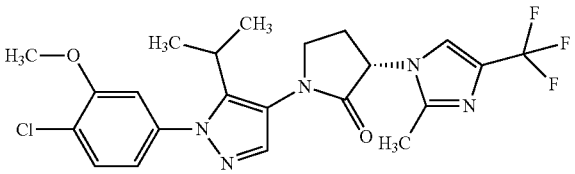 [SMILES: COc1cc(-n2ncc(N3CC[C@H](n4cc(C(F)(F)F)nc4C)C3=O)c2C(C)C)ccc1Cl] | + 1.041 |
| 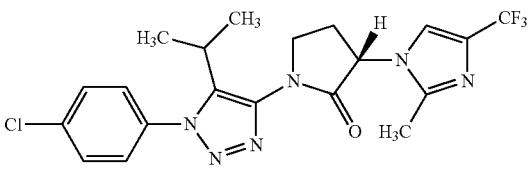 [SMILES: Cc1nc(C(F)(F)F)cn1[C@H]1CCN(c2nnn(-c3ccc(Cl)cc3)c2C(C)C)C1=O] | ++ 1.042 |
| 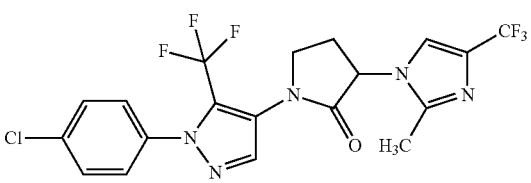 [SMILES: Cc1nc(C(F)(F)F)cn1C1CCN(c2cnn(-c3ccc(Cl)cc3)c2C(F)(F)F)C1=O] | + 1.043 |
| 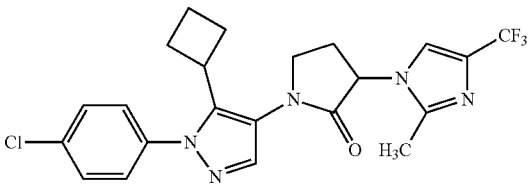 [SMILES: Cc1nc(C(F)(F)F)cn1C1CCN(c2cnn(-c3ccc(Cl)cc3)c2C2CCC2)C1=O] | ++ 1.044 |
| 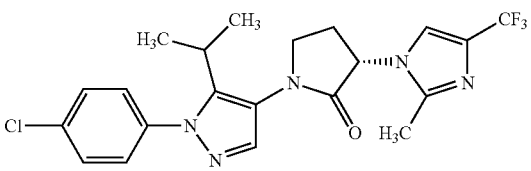 [SMILES: Cc1nc(C(F)(F)F)cn1[C@H]1CCN(c2cnn(-c3ccc(Cl)cc3)c2C(C)C)C1=O] | ++ 1.045 |

What is claimed is:

1. A pharmaceutical composition comprising a compound represented by the structure:

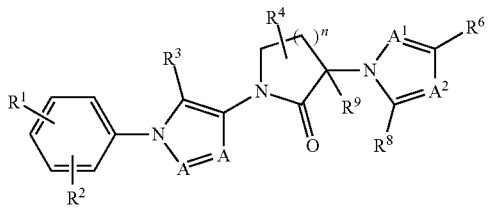

wherein n is 1, 2 or 3;
each A is independently selected from the group consisting of N and CH;
$A^1$ is N or $C(R^5)$;
$A^2$ is N or $C(R^7)$;
$R^1$ and $R^2$ are each independently selected from the group consisting of H, halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, $-OR^a$, $-CO_2R^a$, $-SO_2R^a$, $-NR^aR^b$, $-CONR^aR^b$, and 3-, 4-, 5- or 6-membered heterocycloalkane wherein the heteroatoms present as ring vertices of the heterocycloalkane ring are selected from N, O and S, and wherein the alkyl, cycloalkyl, and hetereocycloalkane portions of $R^1$ and $R^2$ are optionally further substituted with 1-3 $R^a$;
$R^3$ is a member selected from the group consisting of H, halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, $-OR^a$, $-CO_2R^a$, $-NR^aR^b$, $-CONR^aR^b$, aryl, 5- or 6-membered heteroaryl, and 3-, 4-, 5- or 6-membered heterocycloalkane wherein the heteroatoms present as ring vertices of the heteroaryl and heterocycloalkane rings are selected from N, O and S, and wherein the alkyl, cycloalkyl, aryl, heteroaryl and hetereocycloalkane portions of $R^3$ are optionally further substituted with 1-3 $R^a$;
$R^4$ is a member selected from the group consisting of H, $-OR^a$, and $C_{1-8}$ alkyl optionally substituted with $-OR^a$;
$R^5$, $R^6$, $R^7$ and $R^8$ are each independently selected from the group consisting of H, halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, $-OR^a$, $-CO_2R^a$, $-NR^aR^b$, $-CONR^aR^b$, aryl, 5- or 6-membered heteroaryl, and 3-, 4-, 5- or 6-membered heterocycloalkane wherein the heteroatoms present as ring vertices of the heteroaryl and heterocycloalkane rings are selected from N, O and S, and wherein the alkyl, cycloalkyl, aryl, heteroaryl and hetereocycloalkane portions of $R^5$, $R^6$, $R^7$ and $R^8$ are optionally further substituted with 1-3 $R^a$; and optionally, adjacent members of $R^5$, $R^6$, $R^7$ and $R^8$ are connected to form an additional 5- or 6-membered ring which is saturated, unsaturated or aromatic having ring vertices selected from C, O, N and S;
each $R^a$ and $R^b$ is independently selected from the group consisting of hydrogen, hydroxyl, halogen, cyano, $C_{1-8}$ alkyl, $C_{1-8}$ alkoxy, $C_{1-8}$ haloalkyl, $C_{3-6}$ cycloalkyl, $C_{3-6}$ cycloalkylalkyl, amino, $C_{1-8}$ alkylamino, di $C_{1-8}$ alkylamino, carboxamide, carboxy $C_{1-4}$ alkyl ester, carboxylic acid, and $-SO_2-C_{1-8}$ alkyl;
or a pharmaceutically acceptable salt, solvate, hydrate, N-oxide or rotamer thereof;
and a pharmaceutically acceptable excipient or carrier.

2. The pharmaceutical composition of claim 1, where $R^8$ is other than H.

3. The pharmaceutical composition of claim 1, wherein each $R^1$ and $R^2$ is independently selected from the group consisting of H, halogen, CN, $C_{1-8}$ alkyl, $C_{1-8}$ haloalkyl, $-CO_2R^a$ and $-SO_2R^a$.

4. The pharmaceutical composition of claim 1, wherein n is 1.

5. The pharmaceutical composition of claim 1, wherein the ring portion having N, $A^1$ and $A^2$ as ring vertices is selected from the group consisting of:

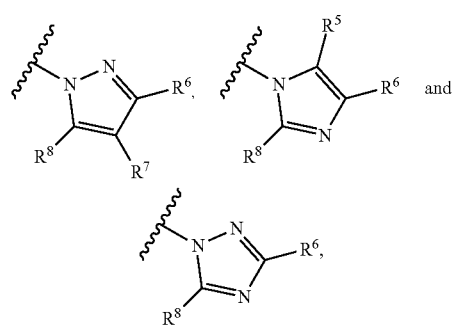

wherein the wavy line indicates the point of attachment to the remainder of the compound.

6. The pharmaceutical composition of claim 1, wherein the ring portion having N, $A^1$ and $A^2$ as ring vertices is selected from the group consisting of:

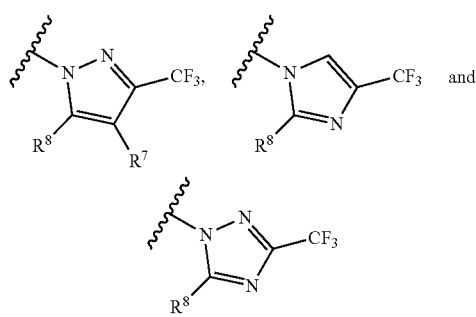

wherein
$R^1$ and $R^2$ are each independently selected from the group consisting of H, halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, $-OR^a$, $-CO_2R^a$, $-SO_2R^a$, $-NR^aR^b$, $-CONR^aR^b$, and 3-, 4-, 5- or 6-membered heterocycloalkane wherein the heteroatoms present as ring vertices of the heterocycloalkane ring are selected from N, O and S, and wherein the alkyl, cycloalkyl, and hetereocycloalkane portions of $R^1$ and $R^2$ are optionally further substituted with 1-3 $R^a$; and
$R^7$ is H or Cl, and $R^8$ is $C_{1-8}$ alkyl optionally substituted with 1 or 2 $R^a$; and
wherein the wavy line indicates the point of attachment to the remainder of the compound.

7. The pharmaceutical composition of claim 4, wherein the compound is represented by the structure:

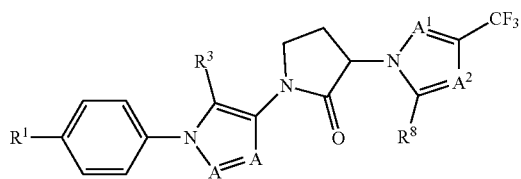

wherein R¹ is Cl or F.

8. The pharmaceutical composition of claim 4, wherein the compound is represented by the structure:

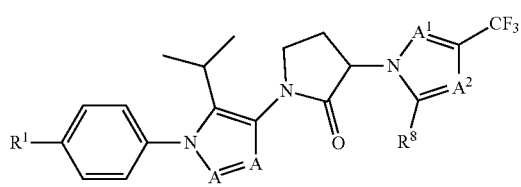

wherein R¹ is Cl or F.

9. The pharmaceutical composition of claim 4, wherein the compound is represented by the structure:

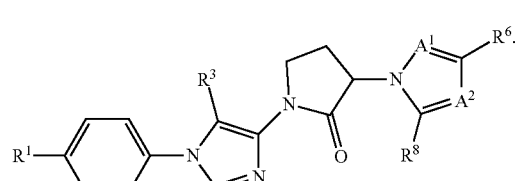

10. The pharmaceutical composition of claim 4, wherein the compound is represented by the structure:

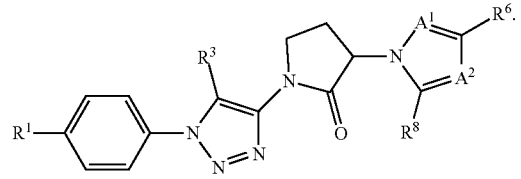

11. The pharmaceutical composition of claim 1, wherein R³ is selected from the group consisting of H, $C_{1-8}$ alkyl, $C_{3-8}$ cycloalkyl and $C_{2-8}$ alkenyl.

12. A method of treating asthma, psoriasis, rheumatoid arthritis, multiple myeloma, osteoporosis, or leukemia comprising administering to a subject in need thereof a therapeutically effective amount of the pharmaceutical composition of claim 1.

13. The pharmaceutical composition of claim 1, wherein the compound is represented by the structure selected from the group consisting of:

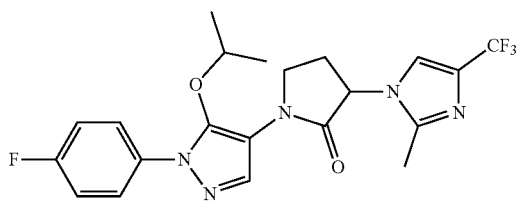
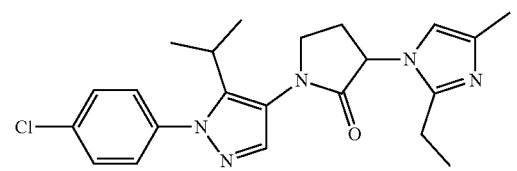
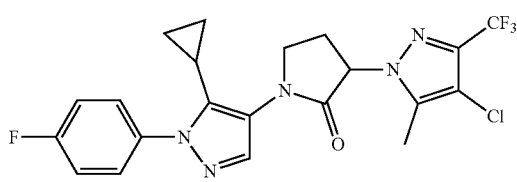
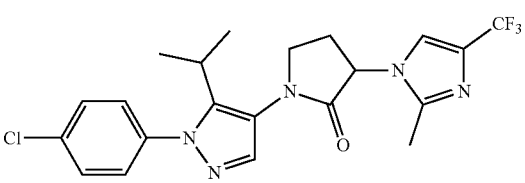
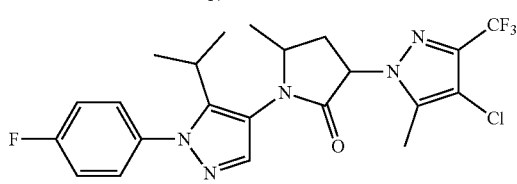
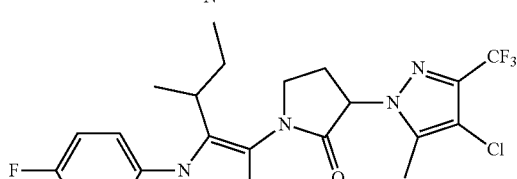
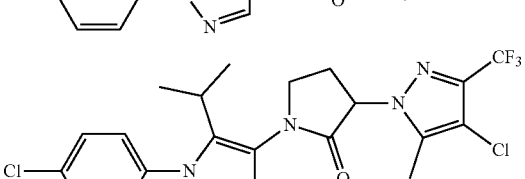
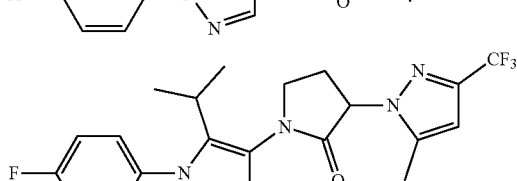
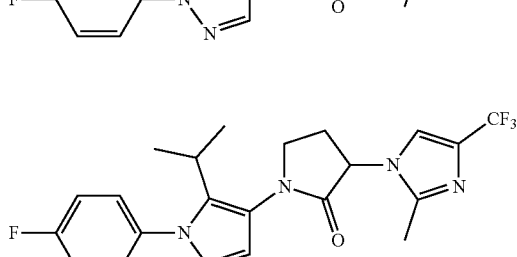

-continued

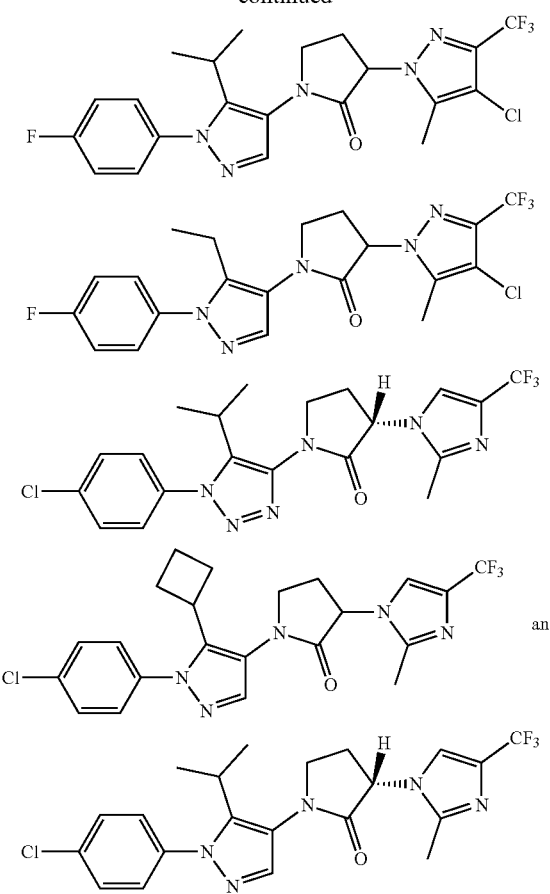

or a pharmaceutically acceptable salt thereof.

14. The pharmaceutical composition of claim 1, wherein the compound is represented by the structure selected from the group consisting of:

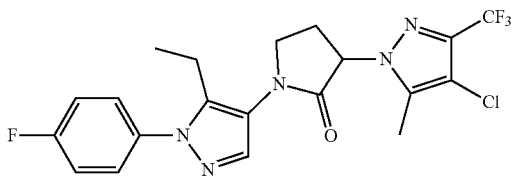

-continued

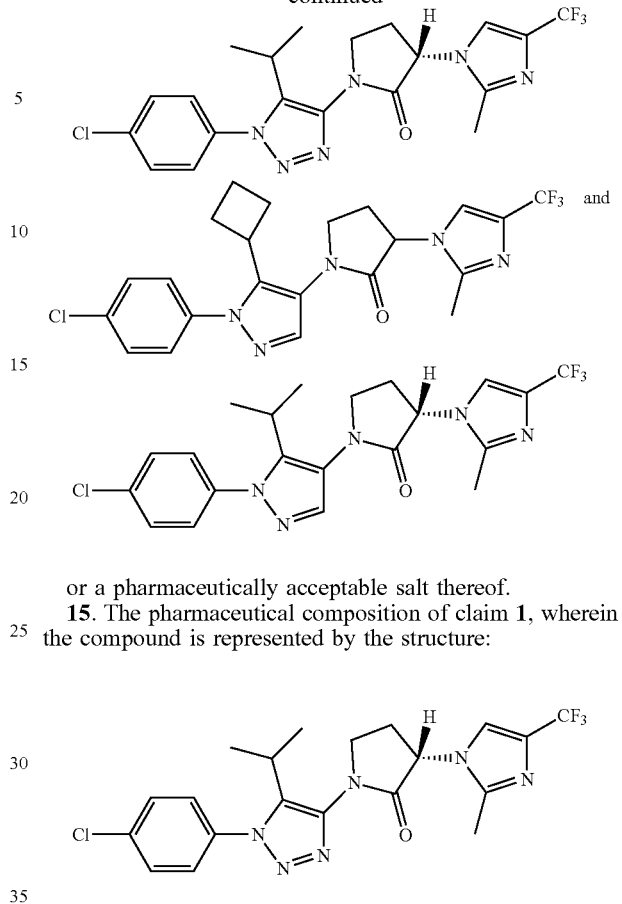

or a pharmaceutically acceptable salt thereof.

15. The pharmaceutical composition of claim 1, wherein the compound is represented by the structure:

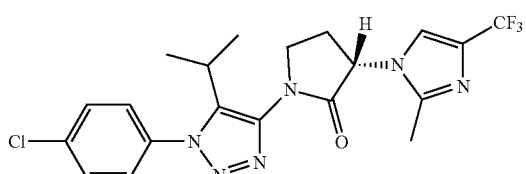

or a pharmaceutically acceptable salt thereof.

16. The pharmaceutical composition of claim 1, wherein the compound is represented by the structure:

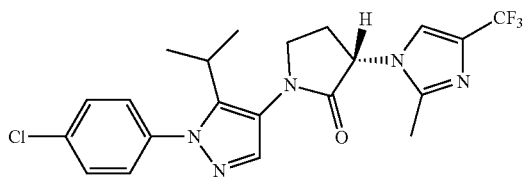 [SMILES: Cc1nc(C(F)(F)F)cn1[C@H]1CCN(c2cnn(-c3ccc(Cl)cc3)c2C(C)C)C1=O]

or a pharmaceutically acceptable salt thereof.

* * * * *